United States Patent
Claremon et al.

(10) Patent No.: US 9,481,674 B1
(45) Date of Patent: Nov. 1, 2016

(54) DIHYDROPYRROLOPYRIDINE INHIBITORS OF ROR-GAMMA

(71) Applicant: Vitae Pharmaceuticals, Inc., Fort Washington, PA (US)

(72) Inventors: David A. Claremon, Maple Grove, PA (US); Jing Yuan, Lansdale, PA (US); Wei Zhao, North Potomac, MD (US); Yajun Zheng, Hockessin, DE (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 0 days.

(21) Appl. No.: 15/178,796

(22) Filed: Jun. 10, 2016

(51) Int. Cl.
*C07D 471/04* (2006.01)

(52) U.S. Cl.
CPC .................. *C07D 471/04* (2013.01)

(58) Field of Classification Search
CPC .................................... C07D 471/04
See application file for complete search history.

(56) References Cited

U.S. PATENT DOCUMENTS

| | | | |
|---|---|---|---|
| 5,238,950 A | 8/1993 | Clader et al. | |
| 5,272,158 A | 12/1993 | Hartman et al. | |
| 5,326,760 A | 7/1994 | McElroy et al. | |
| 5,364,869 A | 11/1994 | De | |
| 5,389,631 A | 2/1995 | Claremon et al. | |
| 5,571,774 A | 11/1996 | Hamprecht et al. | |
| 5,719,144 A | 2/1998 | Hartman et al. | |
| 5,770,590 A | 6/1998 | Natsugari et al. | |
| 5,786,352 A | 7/1998 | Natsugari et al. | |
| 6,103,659 A | 8/2000 | Pasenok et al. | |
| 6,177,443 B1 | 1/2001 | Madsen et al. | |
| 6,417,207 B1 | 7/2002 | Garvey et al. | |
| 6,444,617 B1 | 9/2002 | Takaishi et al. | |
| 6,489,315 B1 | 12/2002 | Natsugari et al. | |
| 6,512,117 B1 | 1/2003 | Harclerode et al. | |
| 6,770,666 B2 | 8/2004 | Hashimoto et al. | |
| 7,112,600 B1 | 9/2006 | Hashimoto et al. | |
| 7,115,752 B2 | 10/2006 | Lesieur et al. | |
| 7,183,318 B2 | 2/2007 | Lesieur et al. | |
| 7,244,730 B2 | 7/2007 | Suzuki et al. | |
| 7,732,616 B2 | 6/2010 | Marlow et al. | |
| 7,750,021 B2 | 7/2010 | Mi et al. | |
| 8,389,739 B1 | 3/2013 | Thacher et al. | |
| 8,415,351 B2 | 4/2013 | Wagner et al. | |
| 9,266,886 B2 | 2/2016 | Lotesta et al. | |
| 2002/0132817 A1 | 9/2002 | Natsugari et al. | |
| 2003/0050320 A1 | 3/2003 | Hashimoto et al. | |
| 2004/0002424 A1 | 1/2004 | Minn et al. | |
| 2004/0038973 A1 | 2/2004 | Nahra et al. | |
| 2005/0004204 A1 | 1/2005 | Suzuki et al. | |
| 2005/0020593 A1 | 1/2005 | Mailliet et al. | |
| 2005/0234065 A1 | 10/2005 | Hulin et al. | |
| 2006/0135557 A1 | 6/2006 | Nan et al. | |
| 2007/0032497 A1 | 2/2007 | Hashimoto et al. | |
| 2007/0112038 A1 | 5/2007 | Marlow et al. | |
| 2007/0258887 A1 | 11/2007 | Tamagnan et al. | |
| 2008/0277622 A1 | 11/2008 | Deshpande et al. | |
| 2008/0287462 A1 | 11/2008 | Chessari et al. | |
| 2009/0036423 A1 | 2/2009 | Pan et al. | |
| 2009/0076275 A1 | 3/2009 | Bolin et al. | |
| 2009/0233945 A9 | 9/2009 | Chessari et al. | |
| 2009/0258871 A1 | 10/2009 | Jitsuoka et al. | |
| 2009/0270405 A1 | 10/2009 | Cook, II et al. | |
| 2010/0099684 A1 | 4/2010 | Cook, II et al. | |
| 2011/0070193 A1 | 3/2011 | Wagner et al. | |
| 2011/0189167 A1 | 8/2011 | Flynn et al. | |
| 2011/0313003 A1 | 12/2011 | Shi et al. | |
| 2012/0077840 A1 | 3/2012 | Turner et al. | |
| 2012/0115903 A1 | 5/2012 | Frank et al. | |
| 2012/0245163 A1 | 9/2012 | Gomtsyan et al. | |
| 2012/0322837 A1 | 12/2012 | Maeba et al. | |
| 2013/0143870 A1 | 6/2013 | Grauert et al. | |
| 2013/0150347 A1 | 6/2013 | Rudolf et al. | |
| 2014/0163001 A1 | 6/2014 | Yamamoto et al. | |
| 2014/0228409 A1 | 8/2014 | Yamamoto et al. | |

FOREIGN PATENT DOCUMENTS

| CA | 2031684 A1 | 6/1991 |
|---|---|---|
| CA | 2134192 A1 | 5/1995 |

(Continued)

OTHER PUBLICATIONS

Maddur et al., "Biology, Pathogenesis of Automimmune and Inflammatory Diseases, and Therapeutic Strategies", The American Journal of Pathology, 181(1):8-18 (2012).

(Continued)

*Primary Examiner* — James D Anderson
(74) *Attorney, Agent, or Firm* — McCarter & English, LLP; Steven G. Davis; Michael J. DeGrazia

(57) ABSTRACT

Provided are novel compounds of Formula (I):

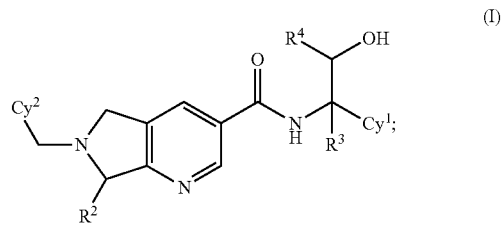

pharmaceutically acceptable salts thereof, and pharmaceutical compositions thereof, which are useful in the treatment of diseases and disorders mediated by RORγ. Also provided are pharmaceutical compositions comprising the novel compounds of Formula (I) and methods for their use in treating one or more inflammatory, metabolic, autoimmune and other diseases or disorders.

6 Claims, 1 Drawing Sheet

(56) References Cited

FOREIGN PATENT DOCUMENTS

| | | |
|---|---|---|
| CA | 2352612 A1 | 6/2000 |
| CA | 2524027 A1 | 12/2004 |
| CN | 1424770 A | 6/2003 |
| CN | 1869036 A | 11/2006 |
| CN | 101225070 A | 7/2008 |
| CN | 101455661 A | 6/2009 |
| CN | 102180780 A | 9/2011 |
| DE | 4343922 A1 | 6/1995 |
| DE | 4446396 A1 | 7/1995 |
| EP | 254951 A2 | 2/1988 |
| EP | 321368 A1 | 6/1989 |
| EP | 468187 A2 | 1/1992 |
| EP | 520277 A2 | 12/1992 |
| EP | 520573 A1 | 12/1992 |
| EP | 540334 A1 | 5/1993 |
| EP | 655439 A2 | 5/1995 |
| EP | 733632 A1 | 9/1996 |
| EP | 1178048 A1 | 2/2002 |
| FR | 2725946 A1 | 4/1996 |
| FR | 2926554 A1 | 7/2009 |
| GB | 2276384 A | 9/1994 |
| JP | H06236056 A | 8/1994 |
| JP | H1143489 A | 2/1999 |
| JP | 2000007661 A | 1/2000 |
| JP | 2003171380 A | 6/2003 |
| JP | 2003531894 A | 10/2003 |
| JP | 2004203791 A | 7/2004 |
| WO | 90/09787 A1 | 9/1990 |
| WO | 94/00119 A1 | 1/1994 |
| WO | 94/24712 A1 | 10/1994 |
| WO | 95/11680 A1 | 5/1995 |
| WO | 95/17397 A1 | 6/1995 |
| WO | 96/26187 A1 | 8/1996 |
| WO | 97/32832 A1 | 9/1997 |
| WO | 98/40385 A1 | 9/1998 |
| WO | 98/42666 A1 | 10/1998 |
| WO | 99/47132 A2 | 9/1999 |
| WO | 99/58495 A1 | 11/1999 |
| WO | 99/58496 A1 | 11/1999 |
| WO | 00/32192 A1 | 6/2000 |
| WO | 00/67754 A1 | 11/2000 |
| WO | 01/05790 A1 | 1/2001 |
| WO | 01/47883 A1 | 7/2001 |
| WO | 01/51128 A1 | 7/2001 |
| WO | 01/83445 A1 | 11/2001 |
| WO | 01/85722 A1 | 11/2001 |
| WO | 02/24650 A2 | 3/2002 |
| WO | 02/38107 A2 | 5/2002 |
| WO | 02/81443 A1 | 10/2002 |
| WO | 02/081447 A1 | 10/2002 |
| WO | 02/081463 A1 | 10/2002 |
| WO | 02/085855 A1 | 10/2002 |
| WO | 03/008421 A1 | 1/2003 |
| WO | 03/029252 A1 | 4/2003 |
| WO | 03/029254 A1 | 4/2003 |
| WO | 03/070710 A1 | 8/2003 |
| WO | 03/076440 A1 | 9/2003 |
| WO | 03/104216 A1 | 12/2003 |
| WO | 2004/014365 A1 | 2/2004 |
| WO | 2004/042029 A2 | 5/2004 |
| WO | 2004/065351 A1 | 8/2004 |
| WO | 2004/089897 A1 | 10/2004 |
| WO | 2004/103309 A2 | 12/2004 |
| WO | 2004/108133 A2 | 12/2004 |
| WO | 2004/111010 A1 | 12/2004 |
| WO | 2004/113330 A1 | 12/2004 |
| WO | 2005/005392 A1 | 1/2005 |
| WO | 2005/011601 A2 | 2/2005 |
| WO | 2005/023806 A2 | 3/2005 |
| WO | 2005/025504 A2 | 3/2005 |
| WO | 2005/028480 A2 | 3/2005 |
| WO | 2005/039564 A1 | 5/2005 |
| WO | 2005/051301 A2 | 6/2005 |
| WO | 2005/060958 A1 | 7/2005 |
| WO | 2005/063296 A2 | 7/2005 |
| WO | 2005/100334 A1 | 10/2005 |
| WO | 2006/032631 A1 | 3/2006 |
| WO | 2006/062981 A2 | 6/2006 |
| WO | 2006/065842 A2 | 6/2006 |
| WO | 2006/074428 A2 | 7/2006 |
| WO | 2006/082001 A1 | 8/2006 |
| WO | 2006/092731 A1 | 9/2006 |
| WO | 2006/109085 A1 | 10/2006 |
| WO | 2007/007054 A1 | 1/2007 |
| WO | 2007/036733 A1 | 4/2007 |
| WO | 2007/036734 A1 | 4/2007 |
| WO | 2007/050124 A1 | 5/2007 |
| WO | 2007/084451 A1 | 7/2007 |
| WO | 2007/084455 A1 | 7/2007 |
| WO | 2007/097931 A2 | 8/2007 |
| WO | 2007/101224 A2 | 9/2007 |
| WO | 2007/107545 A1 | 9/2007 |
| WO | 2007/109596 A2 | 9/2007 |
| WO | 2007/131982 A2 | 11/2007 |
| WO | 2008/013963 A2 | 1/2008 |
| WO | 2008/044027 A2 | 4/2008 |
| WO | 2008/044029 A1 | 4/2008 |
| WO | 2008/044041 A1 | 4/2008 |
| WO | 2008/044045 A1 | 4/2008 |
| WO | 2008/044054 A2 | 4/2008 |
| WO | 2008/048991 A2 | 4/2008 |
| WO | 2008/073865 A2 | 6/2008 |
| WO | 2008/083070 A1 | 7/2008 |
| WO | 2008/086161 A1 | 7/2008 |
| WO | 2008/132155 A2 | 11/2008 |
| WO | 2008/135524 A2 | 11/2008 |
| WO | 2008/135526 A1 | 11/2008 |
| WO | 2008/149163 A2 | 12/2008 |
| WO | 2009/004496 A2 | 1/2009 |
| WO | 2009/013299 A2 | 1/2009 |
| WO | 2009/026248 A2 | 2/2009 |
| WO | 2009/050228 A2 | 4/2009 |
| WO | 2009/052319 A1 | 4/2009 |
| WO | 2009/052320 A1 | 4/2009 |
| WO | 2009/068463 A2 | 6/2009 |
| WO | 2009/073788 A1 | 6/2009 |
| WO | 2009/097972 A1 | 8/2009 |
| WO | 2009/112445 A1 | 9/2009 |
| WO | 2009/112678 A2 | 9/2009 |
| WO | 2009/112826 A1 | 9/2009 |
| WO | 2009/112839 A1 | 9/2009 |
| WO | 2009/124755 A1 | 10/2009 |
| WO | 2009/131926 A1 | 10/2009 |
| WO | 2009/144450 A1 | 12/2009 |
| WO | 2010/003022 A1 | 1/2010 |
| WO | 2010/021878 A1 | 2/2010 |
| WO | 2010/033350 A1 | 3/2010 |
| WO | 2010/056194 A1 | 5/2010 |
| WO | 2010/056195 A1 | 5/2010 |
| WO | 2010/077680 A2 | 7/2010 |
| WO | 2010/086311 A1 | 8/2010 |
| WO | 2011/078143 A1 | 6/2011 |
| WO | 2011/090473 A1 | 7/2011 |
| WO | 2011/094545 A2 | 8/2011 |
| WO | 2011/107248 A1 | 9/2011 |
| WO | 2011/140936 A1 | 11/2011 |
| WO | 2011/146358 A1 | 11/2011 |
| WO | 2011/159297 A1 | 12/2011 |
| WO | 2012/019015 A2 | 2/2012 |
| WO | 2012/027965 A1 | 3/2012 |
| WO | 2012/028100 A1 | 3/2012 |
| WO | 2012/031197 A1 | 3/2012 |
| WO | 2012/043505 A1 | 4/2012 |
| WO | 2012/062462 A1 | 5/2012 |
| WO | 2012/064744 A2 | 5/2012 |
| WO | 2012/100732 A1 | 8/2012 |
| WO | 2012/100734 A1 | 8/2012 |
| WO | 2012/106995 A1 | 8/2012 |
| WO | 2012/125521 A1 | 9/2012 |
| WO | 2012/136296 A1 | 10/2012 |
| WO | 2012/139775 A1 | 10/2012 |
| WO | 2013/000994 A1 | 1/2013 |
| WO | 2013/019621 A1 | 2/2013 |

(56) References Cited

FOREIGN PATENT DOCUMENTS

| | | |
|---|---|---|
| WO | 2013/019626 A1 | 2/2013 |
| WO | 2013/019635 A1 | 2/2013 |
| WO | 2013/019653 A1 | 2/2013 |
| WO | 2013/019682 A1 | 2/2013 |
| WO | 2013/029338 A1 | 3/2013 |
| WO | 2013/045431 A1 | 4/2013 |
| WO | 2013/064231 A1 | 5/2013 |
| WO | 2013/067036 A1 | 5/2013 |
| WO | 2013/079223 A1 | 6/2013 |
| WO | 2013/083741 A1 | 6/2013 |
| WO | 2013/087739 A1 | 6/2013 |
| WO | 2013/092460 A1 | 6/2013 |
| WO | 2013/092939 A1 | 6/2013 |
| WO | 2013/092941 A1 | 6/2013 |
| WO | 2013/096496 A2 | 6/2013 |
| WO | 2013/100027 A1 | 7/2013 |
| WO | 2013/159095 A1 | 10/2013 |
| WO | 2013/160418 A1 | 10/2013 |
| WO | 2013/160419 A1 | 10/2013 |
| WO | 2013/166013 A1 | 11/2013 |
| WO | 2013/169588 A1 | 11/2013 |
| WO | 2013/169704 A2 | 11/2013 |
| WO | 2013/169864 A2 | 11/2013 |
| WO | 2013/171729 A2 | 11/2013 |
| WO | 2013/178362 A1 | 12/2013 |
| WO | 2014/008214 A1 | 1/2014 |
| WO | 2014/009447 A1 | 1/2014 |
| WO | 2014/026327 A1 | 2/2014 |
| WO | 2014/026328 A1 | 2/2014 |
| WO | 2014/026329 A1 | 2/2014 |
| WO | 2014/026330 A1 | 2/2014 |
| WO | 2014/028589 A2 | 2/2014 |
| WO | 2014/028591 A2 | 2/2014 |
| WO | 2014/028597 A2 | 2/2014 |
| WO | 2014/028600 A2 | 2/2014 |
| WO | 2014/028669 A1 | 2/2014 |
| WO | 2014/062938 A1 | 4/2014 |
| WO | 2014/086894 A1 | 6/2014 |
| WO | 2015/116904 A1 | 8/2015 |

OTHER PUBLICATIONS

Marcoux, et al., "Annulation of Ketones with Vinamidinium Hexafluorophosphate Salts: An Efficient Preparation of Trisubstituted Pyridines," Organic Letters, 2000, vol. 2, No. 15, 2339-2341.

Schlecker, et al., "Regioselective Metalation of Pyridinylcarbamates and Pyridinecarboxamides with (2,2,6,6-Tetramethylpiperidino)magnesium Chloride," J. Org. Chem., 1995, 60, 8414-8416.

Schlecker, et al., "Regioselective Monometalation of 2,5-Pyridinedicarboxamides with (2,2,6,6-Tetramethylpiperidino) magnesium Chloride (TMPMgCI)," Liebigs Annalen, 1995, vol. 8, pp. 1441-1446.

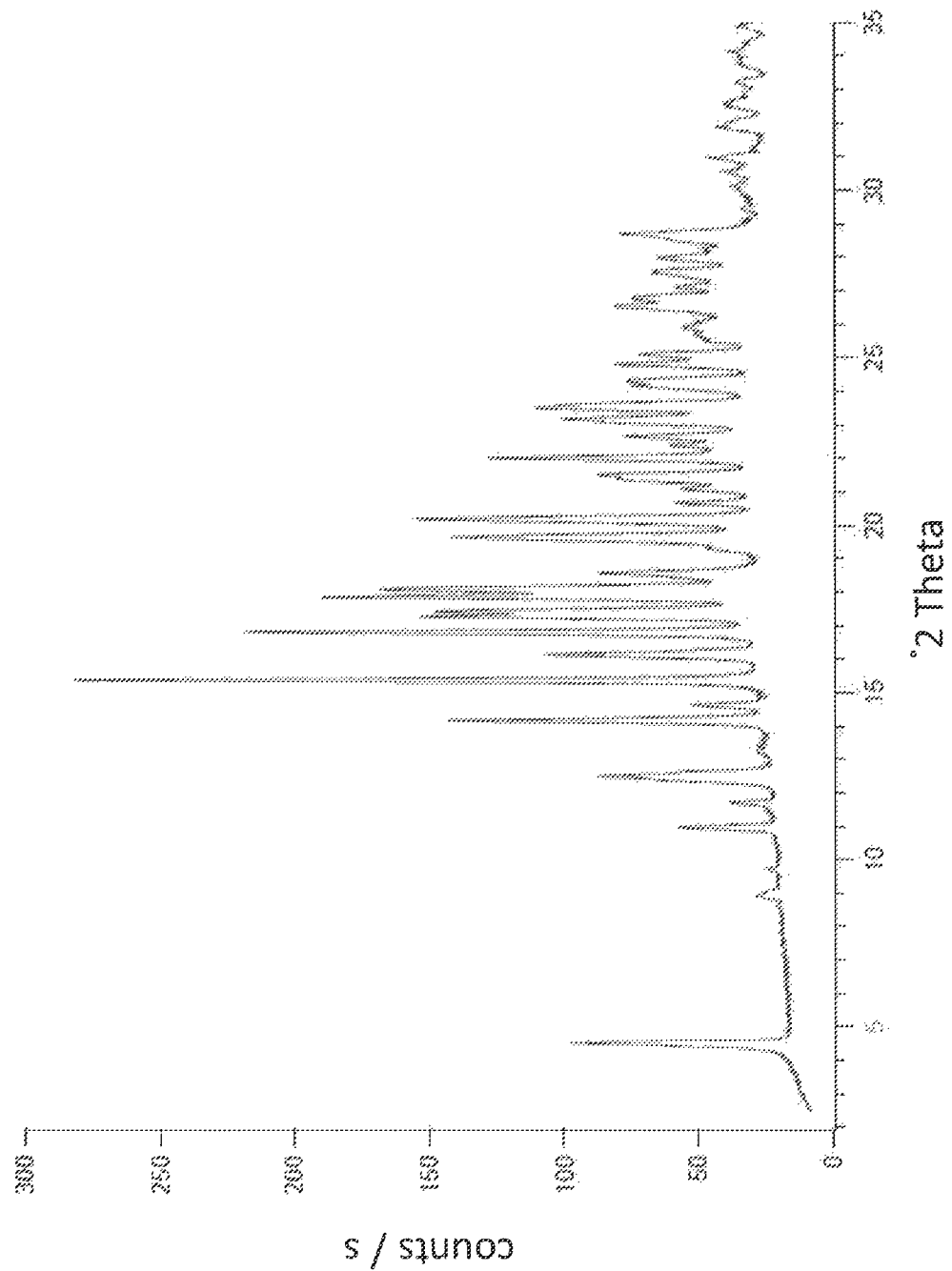

DIHYDROPYRROLOPYRIDINE INHIBITORS OF ROR-GAMMA

RELATED APPLICATIONS

This application is a continuation of International Application No. PCT/US2015/055420, filed Oct. 14, 2015, which claims the benefit of the filing date of U.S. Provisional Application No. 62/063,912, filed Oct. 14, 2014 and U.S. Provisional Application No. 62/074,406, filed Nov. 3, 2014. The entire contents of the aforementioned applications are incorporated herein by reference.

TECHNICAL FIELD OF THE INVENTION

The present invention is directed to novel retinoic acid receptor-related orphan receptor gamma ("ROR$_\gamma$" or "ROR-gamma") inhibitors, processes for their preparation, pharmaceutical compositions containing these inhibitors, and their use in the treatment of inflammatory, metabolic, autoimmune and other diseases mediated by ROR$_\gamma$.

BACKGROUND OF THE INVENTION

Retinoic acid receptor-related orphan receptors (RORs) are a subfamily of transcription factors in the steroid hormone nuclear receptor superfamily (Jetten & Joo (2006) Adv. Dev. Biol. 2006, 16, 313-355). The ROR family consists of ROR alpha (ROR$\alpha$), ROR beta (ROR$\beta$) and ROR gamma (ROR$_\gamma$), each encoded by a separate gene (in human: RORA, RORB and RORC, respectively; in mouse: rora, rorb and rorc, respectively). RORs contain four principal domains shared by the majority of nuclear receptors: an N-terminal domain, a highly conserved DNA-binding domain (DBD) consisting of two zinc finger motifs, a hinge domain, and a ligand binding domain (LBD). Each ROR gene generates several isoforms, differing only in their N-terminal domains. ROR$_\gamma$ has two isoforms: ROR$_\gamma$ 1 and ROR$_\gamma$ 2 (also known as ROR$_\gamma$ t). ROR$_\gamma$ refers to ROR$_\gamma$ 1 and/or ROR$_\gamma$ t. ROR$_\gamma$ 1 is expressed in a variety of tissues including thymus, muscle, kidney and liver, but ROR$_\gamma$ t is exclusively expressed in the cells of the immune system, has a critical role in thymopoiesis and the development of several secondary lymphoid tissues, and is a key regulator of Th17 cell differentiation (Jetten, 2009, Nucl. Recept. Signal., 7:e003, doi:10.1621/nrs.07003, Epub 2009 Apr. 3).

Th17 cells are a subset of T helper cells which preferentially produce the pro-inflammatory cytokines IL-17A, IL-17F, IL-21 and IL-22. Th17 cells and their effector molecules, such as IL-17, IL-21, IL-22, GM-CSF and CCL20, are associated with the pathogenesis of several autoimmune and inflammatory diseases, such as rheumatoid arthritis, systemic lupus erythematosus, multiple sclerosis, psoriasis, inflammatory bowel disease, allergy and asthma (Maddur et al., 2012, Am. J. Pathol., 181:8-18). Recent findings support a role for IL17 and Th17 cells in the pathogenesis of acne (Thiboutot et al., 2014, J. Invest. Dermatol., 134(2):307-10, doi: 10.1038/jid.2013.400; Agak et al., 2014, J. Invest. Dermatol., 134(2):366-73, doi: 10.1038/jid.2013.334, Epub 2013 Aug. 7). Th17 cells are also potent inducers of inflammation associated with endometriosis, a chronic inflammatory disease (Hirata et al., 2010, Endocrinol., 151:5468-5476; Hirata et al., 2011, Fertil Steril., July; 96(1):113-7, doi: 10.1016/j.fertnstert.2011.04.060, Epub 2011 May 20). Additionally, Th17 cells have a key role in the mouse autoimmune models of experimental autoimmune encephalomyelitis (EAE), collagen-induced arthritis (CIA) and adjuvant-induced arthritis (AIA) (Bedoya et al., 2013, Clin. Dev. Immunol., 2013: 986789. Epub 2013 Dec. 26. Th17 cells are activated during inflammatory and autoimmune disease processes and are responsible for recruiting other inflammatory cell types, particularly neutrophils, to mediate pathology in target tissues (Miossec & Kolls, 2012, Nature Rev., 11:763-776; Korn et al., 2009, Annu. Rev. Immunol., 27:485-517). Aberrant Th17 cell function has been implicated in a variety of autoimmune diseases, including multiple sclerosis and rheumatoid arthritis. Autoimmune disease is believed to arise from the disruption of the equilibrium between effector and regulatory T cells (Solt et al., 2012, ACS Chem. Biol., 7:1515-1519, Epub 2012 Jul. 9). The importance of ROR$_\gamma$ t to Th17 cell differentiation and the pathogenic role of Th17 cells is evidenced by the fact that ROR$_\gamma$ t-deficient mice have very few Th17 cells and have a reduction in severity of EAE (Ivanov et al., 2006, Cell, 126:1121-1133).

Circadian rhythms are daily cycles of behavioral and physiological changes that are regulated by endogenous circadian clocks. A number of studies have established links between nuclear receptor (including ROR$_\gamma$) function and expression, the circadian regulatory circuitry, and the regulation of various physiological processes (Jetten (2009) op. cit.).

Obstructive sleep apnea syndrome (OSAS) is a chronic inflammatory disease regulated by T lymphocytes. OSAS patients have a significant increase in peripheral Th17 cell frequency, IL-17 and ROR$_\gamma$ t levels (Ye et al., 2012, Mediators Inflamm., 815308, doi: 10.1155/2012/815308, Epub 2012 Dec. 31).

A number of studies have provided evidence of a role of RORs in cancer. Mice deficient in the expression of ROR$_\gamma$ exhibit a high incidence of thymic lymphomas that metastasize frequently to liver and spleen. High expression of Th17-associated genes (including ROR$_\gamma$) and high levels of Th17 cells in the tumor microenvironment has been shown to correlate with a poor prognosis in various cancers, including lung, gastric, breast and colon cancer (Tosolini et al., 2011, Cancer Res., 71:1263-1271, doi: 10.1158/0008-5472.CAN-10-2907, Epub 2011 Feb. 8; Su et al., 2014, Immunol. Res., 58:118-124, doi: 10.1007/s12026-013-8483-y, Epub 2014 Jan. 9; Carmi et al., 2011, J. Immunol., 186:3462-3471, doi: 10.4049/jimmunol.1002901, Epub 2011 Feb. 7; Chen et al., 2013, Histopathology, 63:225-233, doi: 10.1111/his.12156, Epub 2013 Jun. 6).

ROR$_\gamma$ has also been identified to have a regulatory role in lipid/glucose homeostasis, and has been implicated in metabolic syndrome, obesity (Meissburger et al., 2011, EMBO Mol. Med., 3:637-651), hepatosteatosis, insulin resistance and diabetes.

Further support for the role of ROR$_\gamma$ in the pathogenesis of inflammatory, metabolic, circadian effect, cancer, and autoimmune diseases and disorders can be found in the following references: Chang et al., 2012, J. Exp. Pharmacol., 4:141-148; Jetten et al., 2013, Frontiers Endocrinol., 4:1-8; Huh & Littman, 2012, Eur. J. Immunol., 42:2232-2237; Martinez et al., 2008, Ann. N.Y. Acad. Sci., 1143:188-211; Pantelyushin et al., 2012, J. Clin. Invest., 122:2252-2256; Jetten & Ueda, 2002, Cell Death Differen., 9:1167-1171; Solt et al., 2010, Curr. Opin. Lipidol., 21:204-211.

In light of the role that ROR$_\gamma$ plays in disease pathogenesis, inhibition of ROR$_\gamma$ activity and Th17 cell differentiation and activity, including IL17 production, will be of significant therapeutic benefit. It is therefore desirable to prepare compounds that inhibit ROR$_\gamma$ activity and hence have utility in the treatment of inflammatory, autoimmune, metabolic, circadian effect, cancer, and other diseases mediated by ROR$_\gamma$, such as e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, systemic lupus erythematosus, scleroderma, psoriasis, psoriatic arthritis, steroid resistant asthma and rheumatoid arthritis.

SUMMARY OF THE INVENTION

It has now been found that compounds described herein, and pharmaceutically acceptable compositions thereof, are effective inhibitors of ROR$_\gamma$ (see e.g., Table 2). Such compounds include those of Formula (I):

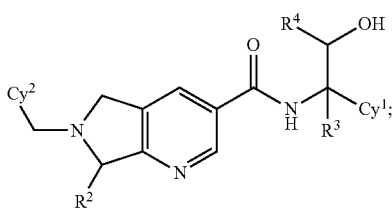

(I)

or a pharmaceutically acceptable salt thereof, wherein each of $R^2$, $R^3$, $R^4$, $Cy^1$, and $Cy^2$ are as defined and described herein.

The provided compounds, and pharmaceutically acceptable compositions thereof, are inverse agonists or antagonists of ROR$_\gamma$ and are useful for treating a variety of diseases, disorders or conditions. Such diseases, disorders, or conditions include those described herein.

The provided compounds can be used alone (i.e., as a monotherapy) or in combination with one or more other therapeutic agent effective for treating any of the indications described herein.

Compounds provided herein possess the technical advantage of having therapeutic relevance in cell-free competition assays, cell-based transcriptional assays, whole blood assays, and hERG potassium channel assays, e.g., see Tables 2 and 3 below.

BRIEF DESCRIPTION OF THE FIGURES

FIG. 1 depicts the powder X-ray diffractogram of (S)-7-ethyl-N—((R)-1-(4-(ethylsulfonyl)phenyl)-2-hydroxyethyl)-6-((trans-4-(trifluoromethyl)cyclohexyl)methyl)-6,7-dihydro-5H-pyrrolo[3,4-b]pyridine-3-carboxamide mesylate.

DETAILED DESCRIPTION OF CERTAIN EMBODIMENTS

1. General Description of Compounds of the Invention

In certain embodiments, the present invention provides a compound of Formula (I):

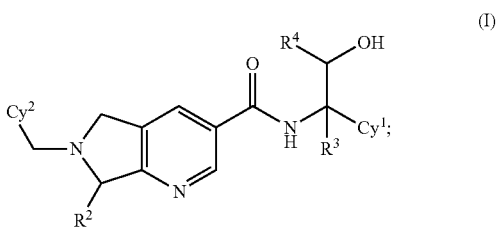

(I)

or a pharmaceutically acceptable salt thereof, wherein:
$R^2$ is $(C_1-C_3)$alkyl, hydroxy$(C_1-C_3)$alkyl, halo$(C_1-C_3)$alkyl, benzyl, $(C_1-C_3)$alkoxy$(C_1-C_3)$alkyl, tetrahydropyranyl, or —CH$_2$-tetrahydropyranyl;
$R^3$ and $R^4$ are each independently hydrogen or methyl;
$Cy^1$ is phenyl or pyridyl, each substituted with $(C_1-C_3)$alkylsulfonyl; and
$Cy^2$ is hydrogen, halo$(C_1-C_3)$alkyl, cyclohexyl, or tetrahydropyranyl, wherein the cyclohexyl and tetrahydropyranyl are each optionally substituted with one or more groups selected from halo$(C_1-C_3)$alkyl and $C_1-C_3$(alkoxy).

2. Compounds and Definitions

The terms "halo" and "halogen" as used herein refer to an atom selected from fluorine (fluoro, —F), chlorine (chloro, —Cl), bromine (bromo, —Br), and iodine (iodo, —I).

The term "alkyl", used alone or as a part of a larger moiety such as e.g., "haloalkyl", means a saturated monovalent straight or branched hydrocarbon radical having, unless otherwise specified, 1-6 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like. "Monovalent" means attached to the rest of the molecule at one point.

The term "haloalkyl" or "halocycloalkyl" include mono, poly, and perhaloalkyl groups where the halogens are independently selected from fluorine, chlorine, iodine, and bromine.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity, i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. When a disclosed compound is named or depicted by structure without indicating a particular geometric isomer form, it is to be understood that the name or structure encompasses one geometric isomer free of other geometric isomers, mixtures of geometric isomers, or all geometric isomers.

The compounds of the invention may be prepared as individual enantiomers by either enantio-specific synthesis or resolved from an enantiomerically enriched mixture. Conventional resolution techniques include forming the salt of a free base of each isomer of an enantiomeric pair using an optically active acid (followed by fractional crystallization and regeneration of the free base), forming the salt of the acid form of each enantiomer of an enantiomeric pair using an optically active amine (followed by fractional crystallization and regeneration of the free acid), forming an ester or amide of each of the enantiomers of an enantiomeric pair using an optically pure acid, amine or alcohol (followed by chromatographic separation and removal of the chiral auxiliary), or resolving an enantiomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses one stereoisomer free of other diastereomers, mixtures of stereoisomers, and mixtures of stereoisomers in which one or more diastereomers is enriched relative to the other diastereomer(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

3. Description of Exemplary Compounds

In a first embodiment, the present invention provides a compound of Formula (I),

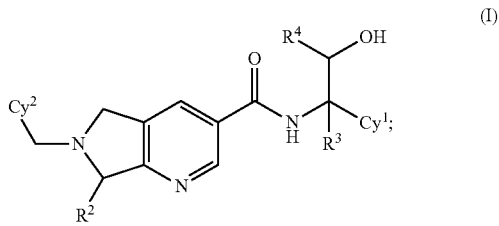

or a pharmaceutically acceptable salt thereof, wherein the variables are as described above.

In a second embodiment, the compound of Formula (I) is of Formula (II):

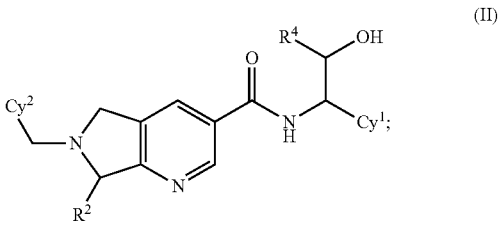

or a pharmaceutically acceptable salt thereof, wherein the variables in structural Formula (II) are as described for Formula (I).

In a third embodiment, the compound of Formula (I) is of Formula (III):

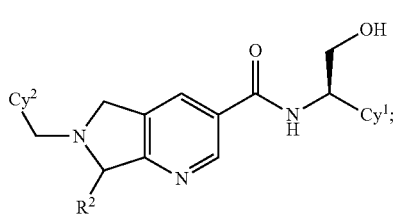
(III)

or a pharmaceutically acceptable salt thereof, wherein the variables in structural Formula (III) are as described for Formula (I).

In a fourth embodiment, the compound of Formula (I) is of Formula (IV):

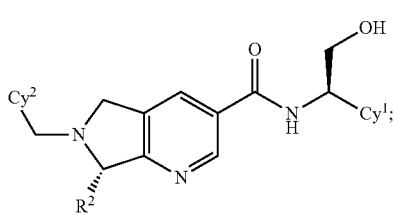
(IV)

or a pharmaceutically acceptable salt thereof, wherein the variables in structural Formula (IV) are as described for Formula (I).

In a fifth embodiment, $Cy^2$ in Formulas (I) to (IV) is cyclohexyl or tetrahydropyranyl, each of which are optionally substituted with one or more groups selected from halo($C_1$-$C_3$)alkyl and $C_1$-$C_3$(alkoxy).

In a sixth embodiment, the compound of Formula (I) is of Formula (V):

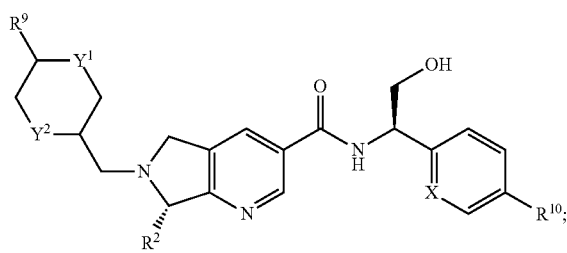
(V)

or a pharmaceutically acceptable salt thereof, wherein X is CH or N, $Y^1$ is O and $Y^2$ is $CH_2$, $Y^1$ is $CH_2$ and $Y^2$ is O, or $Y^1$ and $Y^2$ are each $CH_2$; $R^9$ is halo($C_1$-$C_3$)alkyl; and $R^{10}$ is ($C_1$-$C_3$)alkylsulfonyl, wherein the remaining variables are as described for Formula (I) or the fifth embodiment.

In a seventh embodiment, the compound of Formula (I) is of Formula (VI):

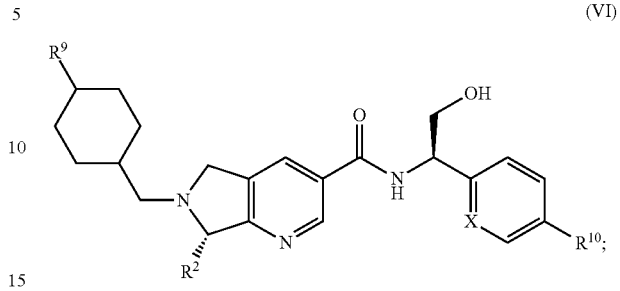
(VI)

or a pharmaceutically acceptable salt thereof, wherein the variables in structural Formula (VI) are as described for Formula (I), or the fifth or sixth embodiment.

In an eighth embodiment, the compound of Formula (I) is of Formula (VII):

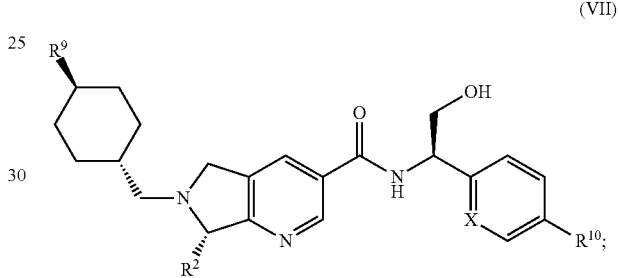
(VII)

or a pharmaceutically acceptable salt thereof, wherein the variables in structural Formula (VII) are as described for Formula (I), or the fifth or sixth embodiment.

In a ninth embodiment, $R^2$ in Formulas (I) to (VII) is methyl, ethyl, benzyl, or isopropyl, wherein the remainder of the variables are as described in Formula (I), or the fifth or sixth embodiment. Alternatively, $R^2$ in Formulas (I) to (VII) is ethyl or isopropyl, wherein the remainder of the variables are as described in Formula (I), or the fifth or sixth embodiment.

In a tenth embodiment, $R^9$ in Formulas (V) and (VII) is $CF_3$ and $R^{10}$ is $SO_2Et$ or $SO_2Me$, wherein the remainder of the variables are as described in Formula (I), or the fifth, sixth, or ninth embodiment.

Specific examples of compounds of the invention are provided in the EXEMPLIFICATION. Pharmaceutically acceptable salts as well as the neutral forms of these compounds are included in the invention.

In certain embodiments, the present invention provides any one of the compounds in the foregoing examples, or a pharmaceutically acceptable salt thereof.

In certain embodiments, the present invention provides a method of treating a patient (e.g., a human) with a disorder mediated by RORγ comprising the step of administering to the patient an effective amount of the compound with any compound described herein, or a pharmaceutically acceptable salt or composition thereof.

4. Uses, Formulation and Administration

Pharmaceutically Acceptable Compositions

According to another embodiment, the present invention provides a method of treating a subject (e.g., a human) with a disorder mediated by RORγ using a composition comprising a compound of the invention and a pharmaceutically acceptable carrier, adjuvant, or vehicle. In certain embodiments, the amount of compound of the invention in a provided composition is such that it is effective as an inverse agonist or antagonist to RORγ in a biological sample or in a subject. In certain embodiments, a provided composition is formulated for administration to a subject in need of such composition. In some embodiments, a provided composition is formulated for oral administration to a subject.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for the inhibition of ROR$\gamma$. Thus, in some embodiments, the present invention provides a method of treating inflammatory, metabolic and autoimmune diseases or disorders mediated by ROR$\gamma$, comprising administering a provided compound or composition. More particularly, the compounds and compositions described herein act as inverse agonists or antagonists of ROR$\gamma$.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

Diseases and conditions treatable according to the methods of the invention include, but are not limited to, inflammatory, metabolic and autoimmune diseases or disorders mediated by ROR$\gamma$. These diseases and conditions include, for example, asthma, chronic obstructive pulmonary disease (COPD), bronchitis, allergic rhinitis, atopic dermatitis, contact dermatitis, acne, urticaria, hives, angioedema, cystic fibrosis, allograft rejection, multiple sclerosis, Balo's concentric (circular) sclerosis, Balo disease, leukoencephalitis periaxialis concentrica, encephalitis periaxialis concentrica, scleroderma, limited scleroderma, CREST syndrome, arthritis, rheumatoid arthritis, juvenile rheumatoid arthritis, reactive arthritis, Reiter's syndrome, osteoarthritis, ankylosing spondylitis, systemic lupus erythematosus (SLE), psoriasis, plaque psoriasis, guttate psoriasis, inverse psoriasis, pustular psoriasis, erythrodermic psoriasis, psoriatic epidermal hyperplasia, epidermal hyperplasia, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, psoriatic arthritis (PsA), steroid resistant asthma, Graves' disease, scleritis, endometriosis, obstructive sleep apnea syndrome (OSAS), Behç et's disease, dermatomyositis, polymyositis, graft versus host disease, chronic graft versus host disease, acute graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, celiac sprue, neuromyelitis, juvenile idiopathic arthritis, systemic sclerosis, myocardial infarction, pulmonary hypertension, osteoarthritis, cutaneous leishmaniasis, sinonasal polyposis, cancer, including but not limited to lung cancer, gastric cancer, breast cancer and colon cancer, thrombocytopenic purpura, idiopathic thrombocytopenic purpura (ITP), immune thrombocytopenic purpura, cartilage inflammation, bone degradation, vasculitis, acute disseminated encephalomyelitis (ADEM), acute necrotizing hemorrhagic leukoencephalitis, Addison's disease, agammaglobulinemia, alopecia areata, amyloidosis, anti-glomerular basement membrane (GBM) nephritis, anti-tubular basement membrane (TBM) nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticaria, axonal and neuronal neuropathies, bullous pemphigoid, cardiomyopathy, Castleman disease, Chagas disease, chronic inflammatory demyelinating polyneuropathy (CIDP), chronic recurrent multifocal ostomyelitis (CRMO), Churg-Strauss syndrome, cicatricial pemphigoid, benign mucosal pemphigoid, Cogan's syndrome, cold agglutinin disease, congenital heart block, coxsackie myocarditis, essential mixed cryoglobulinemia, demyelinating neuropathies, dermatitis herpetiformis, Devic's disease, neuromyelitis optica, discoid lupus, Dressler's syndrome, eosinophilic esophagitis, eosinophilic fascitis, erythema nodosum, experimental allergic encephalomyelitis, Evans syndrome, fibrosing alveolitis, giant cell arteritis, temporal arteritis, giant cell myocarditis, glomerulonephritis, Goodpasture's syndrome, granulomatosis with polyangiitis (GPA), Wegener's granulomatosis, Hashimoto's encephalitis, Hashimoto's thyroiditis, hemolytic anemia, Henoch-Schonlein purpura, herpes gestationis, hypogammaglobulinemia, IgA nephropathy, IgG4-related sclerosing disease, immunoregulatory lipoproteins, inclusion body myositis, interstitial cystitis, juvenile myositis, Kawasaki syndrome, Lambert-Eaton syndrome, leukocytoclastic vasculitis, lichen planus, lichen sclerosus, ligneous conjunctivitis, linear IgA disease (LAD), chronic Lyme disease, Meniere's disease, microscopic polyangiitis, mixed connective tissue disease (MCTD), Mooren's ulcer, Mucha-Habermann disease, myositis, narcolepsy, neuromyelitis optica, Devic's syndrome, neutropenia, ocular cicatricial pemphigoid, optic neuritis, palindromic rheumatism, pediatric autoimmune neuropsychiatric disorders associated with streptococcus (PANDAS), paraneoplastic cerebellar degeneration, paroxysmal nocturnal hemoglobinuria (PNH), Parry-Romberg syndrome, Parsonnage-Turner syndrome, pars planitis, peripheral uveitis, pemphigus, peripheral neuropathy, perivenous encephalomyelitis, pernicious anemia, POEMS syndrome, polyarteritis nodosa, type I autoimmune polyglandular syndrome, type II autoimmune polyglandular syndrome, type III autoimmune polyglandular syndrome, polymyalgia rheumatic, postmyocardial infarction syndrome, postpericardiotomy syndrome, progesterone dermatitis, primary biliary cirrhosis, primary sclerosing cholangitis, idiopathic pulmonary fibrosis, pyoderma gangrenosum, pure red cell aplasia, Raynaud's phenomenon, reflex sympathetic dystrophy, relapsing polychondritis, restless legs syndrome, retroperitoneal fibrosis, rheumatic fever, rheumatoid arthritis, sarcoidosis, Schmidt syndrome, sperm autoimmunity, stiff person syndrome, subacute bacterial endocarditis (SBE), Susac's syndrome, sympathetic ophthalmia, Takayasu's arteritis, temporal arteritis, giant cell arteritistesticular autoimmunity, Tolosa-Hunt syndrome, transverse myelitis, undifferentiated connective tissue disease (UCTD), vesiculobullous dermatosis, and vitiligo.

Also included are diseases or disorders which are implicated by the regulation of the circadian rhythm of individuals and include, e.g., major depression, seasonal affective disorder, post-traumatic stress disorder (PTSD), bipolar disorder, autism, epilepsy, Alzheimer's and other central nervous system (CNS) disorders associated with altered sleep and/or circadian rhythms.

In one embodiment, a human patient is treated with a compound of the invention and a pharmaceutically acceptable carrier, adjuvant, or vehicle, wherein said compound is present in an amount to treat or ameliorate one or more of the diseases and conditions recited above. In another embodiment, the diseases and conditions treated or ameliorated by a compound of the invention include, i.e., asthma, COPD, bronchitis, allergic rhinitis, atopic dermatitis, contact dermatitis, acne, urticaria, cystic fibrosis, allograft rejection, multiple sclerosis, scleroderma, arthritis, rheumatoid arthritis, juvenile rheumatoid arthritis, osteoarthritis, ankylosing spondylitis, SLE, psoriasis, Hashimoto's disease, pancreatitis, autoimmune diabetes, type I diabetes, autoimmune ocular disease, ulcerative colitis, Crohn's disease, regional enteritis, IBD, IBS, Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, PsA, steroid resistant asthma, Graves' disease, scleritis, major depression, seasonal affective disorder, PTSD, bipolar disorder, autism, epilepsy, Alzheimer's, CNS disorders associated with altered sleep and/or circadian rhythms, endometriosis, OSAS, Behç et's disease, dermatomyositis, polymyocitis, graft versus host disease, primary biliary cirrhosis, liver fibrosis, NAFLD, sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer. In an alternative embodiment, the diseases and conditions treated or ameliorated by a compound of the invention include, e.g., asthma, atopic dermatitis, acne, Crohn's disease, regional enteritis, ulcerative colitis, Sjögren's syndrome, uveitis, Behç et's disease, dermatomyositis, multiple sclerosis, ankylosing spondylitis, SLE, scleroderma, psoriasis, PsA, steroid resistant asthma and rheumatoid arthritis in the patient.

The invention further relates to a combination therapy for treating or ameliorating a disease or a disorder described herein. In some embodiments, the combination therapy comprises administering at least one compound of the invention in combination with one or more agents for treating or ameliorating inflammatory, metabolic and autoimmune diseases or disorders mediated by RORγ. In some embodiments, the combination therapy comprises administering at least one compound of the invention in combination with one or more agents for treating or ameliorating a disease or a disorder described herein. In some embodiments, the combination therapy comprises administering at least one compound of the invention in combination with one or more agents for the treatment of diseases including asthma, atopic dermatitis, acne, Crohn's disease, regional enteritis, ulcerative colitis, Sjögren's syndrome, uveitis, Behç et's disease, dermatomyositis, multiple sclerosis, ankylosing spondylitis, SLE, scleroderma, psoriasis, PsA, steroid resistant asthma and rheumatoid arthritis.

The compounds according to the invention may also be used in combination with immunotherapies for the treatment of a disease or disorder disclosed herein.

Combination therapy includes, e.g., co-administration of a compound of the invention and one or more other agents, sequential administration of a compound of the invention and one or more other agents, administration of a composition containing a compound of the invention and one or more other agents, or simultaneous administration of separate compositions containing a compound of the invention and one or more other agents.

The invention further provides a method of treating a subject, such as a human, suffering from one of the above-mentioned disorders or diseases.

The invention further relates to the use of provided compounds for the production of pharmaceutical compositions which are employed for the treatment and/or prophylaxis and/or amelioration of the diseases and disorders mentioned herein.

Compounds or compositions described herein may be administered using any amount and any route of administration effective for treating or lessening the severity of one or more of the diseases and conditions described herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

The amount of both, a provided compound and additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent.

The amount of additional therapeutic agent present in the compositions of this disclosure will be no more than the amount that would normally be administered in a composition comprising that therapeutic agent as the only active agent.

Exemplification

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Description of Synthesis

The compounds of the present invention can be readily prepared according to the following reaction schemes and examples, or modifications thereof, using readily available starting materials, reagents and conventional synthesis procedures. Many of the reactions can also be carried out under microwave (MW) conditions or using conventional heating or utilizing other technologies such as solid phase reagents/scavengers or flow chemistry. In these reactions, it is also possible to make use of variants which are themselves known to those of ordinary skill in the art, but are not mentioned in greater detail. Furthermore, other methods for preparing compounds of the invention will be readily apparent to a person of ordinary skill in the art in light of the following reaction schemes and examples. In cases where synthetic intermediates and final products contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. In the discussion below variables have the meanings indicated above unless otherwise indicated. The abbreviations used in these experimental details are listed below and additional ones should be known to a person skilled in the art of synthesis. In addition, one can refer to the following references for suitable methods of synthesis as described in March, Advanced Organic Chemistry, 3rd edition, John Wiley & Sons, 1985, Greene and Wuts, Protective Groups in Organic Synthesis, $2^{nd}$ edition, John Wiley & Sons, 1991, and Richard Larock, Comprehensive Organic Transformations, $4^{th}$ edition, VCH publishers Inc., 1989.

Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

Where NMR data are presented, spectra were obtained on a Varian 400 (400 MHz) or 300 (300 MHz) and are reported as ppm downfield from tetramethylsilane with number of proton, multiplicities and coupling constants indicated parenthetically along with reference to deuterated solvent.

The invention is illustrated by way of the following examples, in which the following abbreviations may be employed.

| Abbreviation | Meaning |
|---|---|
| ACN, MeCN, $CH_3CN$ | acetonitrile |
| AIBN | azobisisobutyronitrile |
| aq | aqueous |
| Boc | tert-butoxycarbonyl or t-butoxycarbonyl |
| brine | saturated aqueous NaCl |
| Cbz | benzyloxy carbonyl |
| Cpd | compound |
| DCM or $CH_2Cl_2$ | methylene chloride |
| DIEA | diisopropyl ethyl amine |
| DMF | dimethyl formamide |
| DMS/$Me_2S$ | dimethyl sulfide |
| DMSO | dimethyl sulfoxide |
| EDCI | 1-(3-dimethylaminopropyl)-3-ethylcarbodiiimide hydrochloride |
| EtI | ethyl iodide |
| Et | ethyl |
| $Et_2O$ | ethyl ether |
| $Et_3SiH$ | triethylsilane |

| Abbreviation | Meaning |
| --- | --- |
| Et$_3$N | triethylamine |
| EtOAc, EA, AcOEt | ethyl acetate |
| EtOH | ethanol |
| h, hr | hour(s) |
| HATU | O-(7-azabenzotriazol-1-yl)-N,N,N',N'-tetramethyluronium-hexafluorophosphate |
| HBTU | O-benzotriazole-1-yl-/N,N,N',N'-tetramethyluronium-hexafluorophosphate |
| HCl | hydrochloric acid |
| H$_2$O$_2$ | hydrogen peroxide |
| HPLC | high performance liquid chromatography |
| i-BuOCOCl | iso-butoxycarbonyl chloride |
| ICl | iodochloride |
| K$_3$PO$_4$ | tripotassium phosphate |
| LC-MS | liquid chromatography-mass spectrometry |
| LDA | lithium diisopropylamide |
| MCPBA, m-CPBA | meta-chloroperoxybenzoic acid |
| MeOH | methanol |
| MeI | methyl iodide |
| Me | methyl |
| mg | milligram |
| min | minute(s) |
| mL | milliliters |
| mmol | millimoles |
| mp, m.p. | melting point |
| MS | mass spectrometry |
| MW, uwave | microwave |
| NBS | N-bromosuccinimide |
| n-BuLi | n-butyllithium |
| NMM | N-methyl-morpholine |
| NMP | N-methyl-pyrrolidin-2-one |
| OTf | trifluoromethanesulfonate |
| OTs | tosylate |
| PdCl$_2$dppf | [1,1-bis(diphenylphosphino)ferrocene]dichloropalladium(ii) |
| Pd$_2$(dba)$_3$ | tris(dibenzylideneacetone)dipalladium(0) |
| PE | petroleum ether |
| rt | room temperature |
| sat. | saturated |
| SFC | supercritical fluid chromatography |
| t-BuOK | potassium tert butoxide |
| t-BuLi | tert butyl lithium |
| t-BuOOH | tert butyl peroxide |
| TBAF | tetrabutylammonium fluoride |
| TFA | trifluoroacetic acid |
| THF | tetrahydrofuran |
| TLC | thin layer chromatography |
| Ti(OEt)$_4$ | titanium tetra ethoxide |

Compounds according to Formula (I), can be prepared by reacting an intermediate compound of Formula (500) with an alkyl or benzyl halide, according to reaction Scheme 1, a reaction that is performed in a polar aprotic solvent, such as, for example, acetonitrile, in the presence of a suitable base, such as, for example, N,N-diisopropylethylamine or potassium carbonate. Alternatively, the final compounds according to Formula (I), can be prepared by reacting an intermediate compound of Formula (500) with an aldehyde, according to reaction Scheme 1, following art-known reductive amination procedure, in the typical solvent, such as, for example, dichloroethane, dichloromethane, or methanol; in the presence of suitable reducing reagent, such as sodium cyanoborohydride or sodium triacetoxyborohydride. In reaction Scheme 1, all variables are defined as in Formula (I) and G$^1$ is a leaving group, such as for example, bromide, chloride, mesylate (methanesulfonate), tosylate (p-toluenesulfonate), trifluorormethanesulfonate (triflate), or iodide.

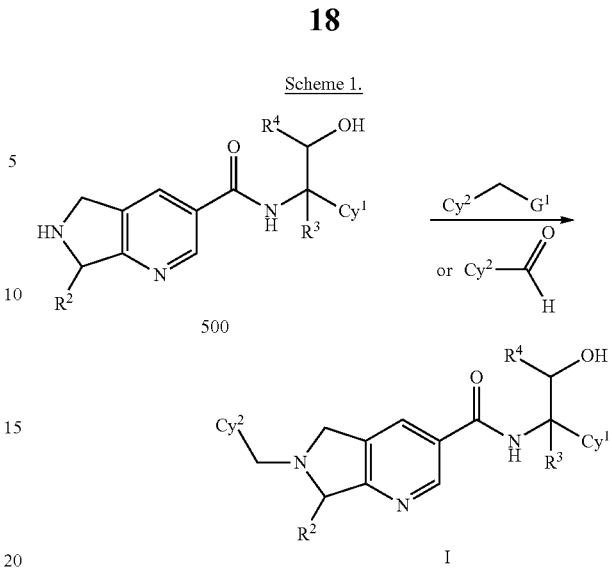

Intermediate compound of Formula (500) can be can be prepared by deprotecting an intermediate compound of Formula (501), wherein Pg is a suitable nitrogen protecting group (Greene and Wuts, Protective Groups in Organic Synthesis, 2$^{nd}$ edition, John Wiley & Sons, 1991), e.g., Pg=tert-butylcarbamate, removed with trifluoroacetic acid according to Scheme 2. In reaction Scheme 2, all variables are defined as in Formula (I).

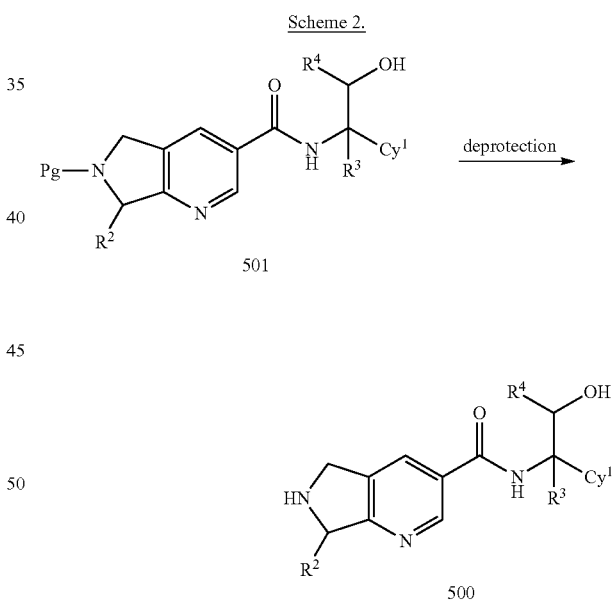

Intermediate compound of Formula (501) can be prepared from a carboxylic acid (502) and an amine (503), according to Scheme 3. The reaction is conveniently carried out in the presence of an activating reagent, for example, N-(3-Dimethylaminopropyl)-N'-ethylcarbodiimide hydrochloride (EDCI) or O-(7-azabenzotriazol-1-yl)-N,N,N',N'-tetramethyluronium hexafluorophosphate (HATU), in an organic solvent, for example, N,N-dimethylformamide or dichloromethane, optionally in the presence of a base, e.g., N,N-diisopropylethylamine or triethylamine, at a temperature, for example in the range from 0 to 60° C.

Scheme 3.

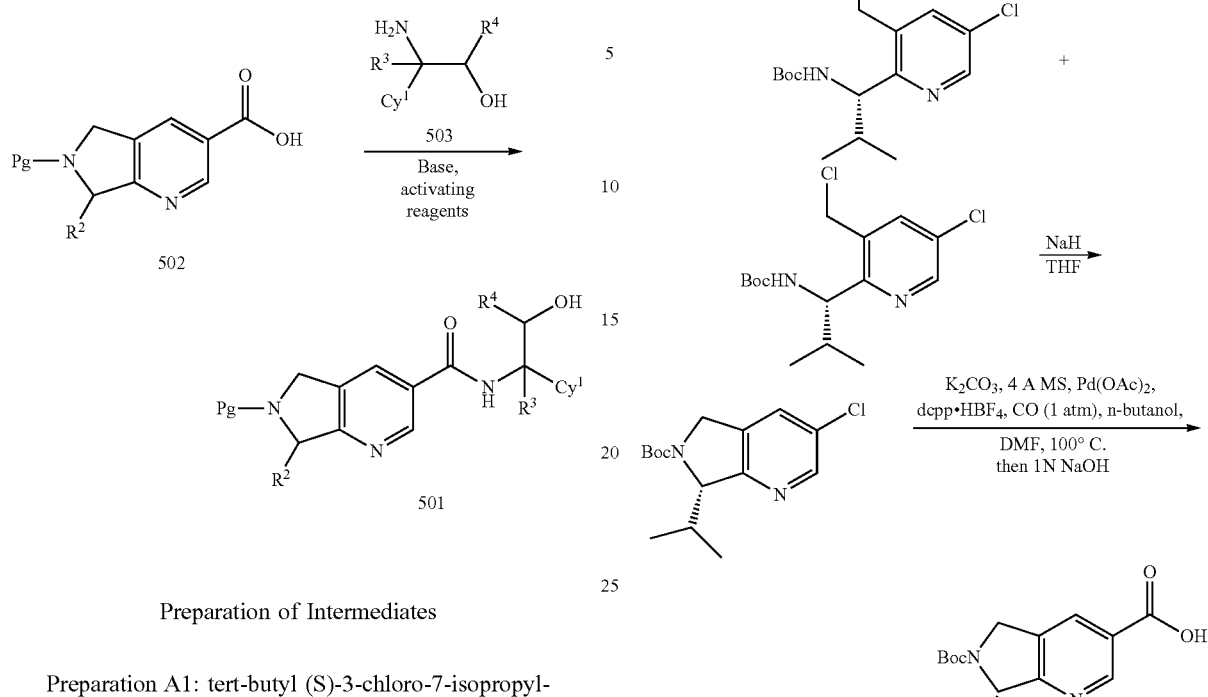

Preparation of Intermediates

Preparation A1: tert-butyl (S)-3-chloro-7-isopropyl-5,7-dihydro-6H-pyrrolo[3,4-b]pyridine-6-carboxylate

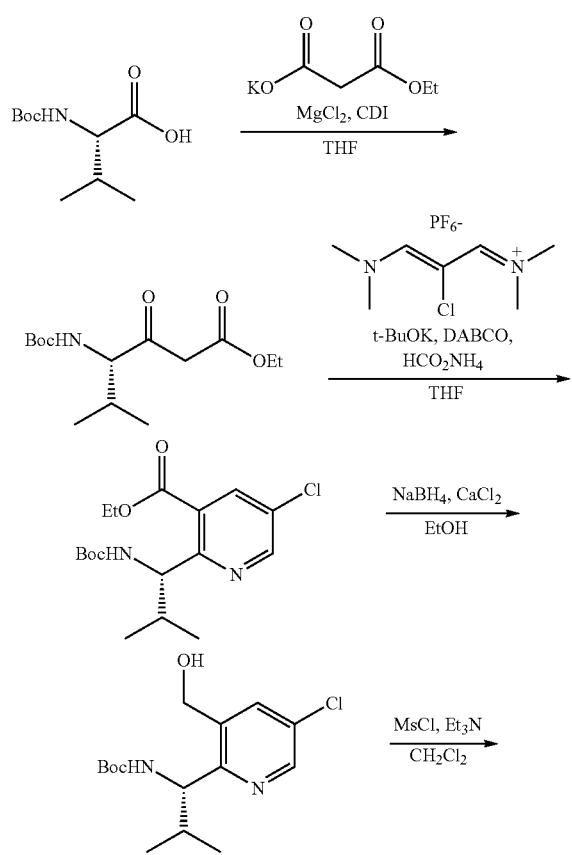

Step 1: ethyl (S)-4-((tert-butoxycarbonyl)amino)-5-methyl-3-oxohexanoate

To a stirred solution of Boc-Val-OH (3.11 g, 14.3 mmol) in THF (40 mL) at rt was added 1,1'-carbonyldiimidazole (3.48 g, 21.5 mmol). The mixture was stirred at rt for 1 h, then magnesium chloride (1.36 g, 14.3 mmol) and ethyl potassium malonate (2.44 g, 14.3 mmol) were added successively. The mixture was then heated to 50° C. and stirred for 15 h. The mixture was cooled to rt and quenched with 1 N HCl (100 mL). The aqueous phase was extracted with EtOAc (3×100 mL), then the combined organic layer was washed with brine (50 mL). The organic layer was dried over anhydrous MgSO$_4$, filtered and concentrated under reduced pressure. The residue was purified by silica gel chromatography (eluting with 5% EtOAc in hexanes) to afford ethyl (S)-4-((tert-butoxycarbonyl)amino)-5-methyl-3-oxohexanoate (3.53 g, 86% yield) as a yellow oil. LC-MS $t_R$=0.91 min in 1 min chromatography, MS (ESI) m/z 288.3 [M+H]$^+$. $^1$H NMR (CDCl$_3$, 400 MHz): δ 5.08 (d, J=8.4 Hz, 1H), 4.33 (dd, J=4.4 Hz, 8.8 Hz, 1H), 4.20 (q, J=7.2 Hz, 2H), 3.54 (s, 2H), 2.27-2.17 (m, 1H), 1.44 (s, 9H), 1.27 (t, J=7.2 Hz, 3H), 1.01 (d, J=6.8 Hz, 3H), 0.82 (d, J=6.8 Hz, 3H).

Step 2: (S)-2-(1-((tert-butoxycarbonyl)amino)-2-methylpropyl)-5-chloronicotinate To a mixture of ethyl (S)-4-((tert-butoxycarbonyl)amino)-5-methyl-3-oxohexanoate (9.68 g, 33.7 mmol) from above in THF (100 mL) at 0° C. was added potassium tert-butoxide (3.78 g, 35.4 mmol). The mixture was warmed to rt and stirred for 45 min, at which point 1,4-diazabicyclo[2.2.2]

octane (3.78 g, 33.7 mmol) and 2-chloro-1,3-bis(dimethylamino)trimethinium hexaflurophosphate (15.5 g, 50.5 mmol) were added successively. The mixture was heated to 45° C. and stirred for 3 h, at which point ammonium acetate (5.19 g, 67.4 mmol) was added. The mixture was then heated to reflux and stirred for 15 h. It was then cooled to rt and concentrated under reduced pressure. The residue was dry-loaded onto a silica gel column and purified (eluting with 5% EtOAc in hexanes, gradient to 15%) to yield 6.09 g of ethyl (S)-2-(1-((tert-butoxycarbonyl)amino)-2-methylpropyl)-5-chloronicotinate (51%). LC-MS $t_R$=1.14 min in 1 min chromatography, MS (ESI) m/z 357.3 [M+H]$^+$. $^1$H NMR (CDCl$_3$, 400 MHz): δ 8.61 (d, J=2.4 Hz, 1H), 8.18 (d, J=2.8 Hz, 1H), 5.71 (d, J=9.6 Hz, 1H), 5.62 (dd, J=5.2 Hz, 9.6 Hz, 1H), 4.42 (q, J=7.2 Hz, 2H), 2.08-2.00 (m, 1H), 1.42 (s, 9H), 1.42 (t, J=7.2 Hz, 3H), 0.93 (d, J=6.4 Hz, 3H), 0.83 (d, J=6.4 Hz, 3H).

Step 3: tert-butyl (S)-(1-(5-chloro-3-(hydroxymethyl)pyridin-2-yl)-2-methylpropyl)carbamate To a stirred solution of ethyl (S)-2-(1-((tert-butoxycarbonyl)amino)-2-methylpropyl)-5-chloronicotinate (6.09 g, 17.1 mmol) at 0° C. in EtOH (70 mL) was added sodium borohydride (1.30 g, 34.1 mmol). Calcium chloride (1.89 g, 17.1 mmol) was added portionwise while maintaining the temperature between 0° C. and 5° C. The resulting mixture was stirred at 0° C. for 90 min, then quenched slowly at 0° C. with saturated aqueous ammonium chloride solution (100 mL). The aqueous phase was extracted with EtOAc (3×100 mL), then the combined organic layer was washed with brine (50 mL), dried over anhydrous MgSO$_4$, filtered and concentrated under reduced pressure. Crude tert-butyl (S)-(1-(5-chloro-3-(hydroxymethyl)pyridin-2-yl)-2-methylpropyl)carbamate was carried forward without any purification. LC-MS $t_R$=0.94 min in 1 min chromatography, MS (ESI) 315.3 [M+H]$^+$. $^1$H NMR (CDCl$_3$, 400 MHz): δ 8.46 (d, J=2.4 Hz, 1H), 7.67 (d, J=2.8 Hz, 1H), 5.34 (d, J=9.2 Hz, 1H), 4.99 (dd, J=2.0 Hz, 8.4 Hz, 1H), 4.54 (t, J=9.2 Hz, 1H), 4.41 (dd, J=10.0 Hz, 12.4 Hz, 1H), 4.33 (d, J=10.0 Hz, 1H), 2.18-2.12 (m, 1H), 1.36 (s, 9H), 1.10 (d, J=6.4 Hz, 3H), 0.69 (d, J=6.8 Hz, 3H).

Step 4: (S)-(2-(1-((tert-butoxycarbonyl)amino)-2-methylpropyl)-5-chloropyridin-3-yl)methyl methanesulfonate To a solution of tert-butyl (S)-(1-(5-chloro-3-(hydroxymethyl)pyridin-2-yl)-2-methylpropyl)carbamate (5.33 g, 16.9 mmol) in CH$_2$Cl$_2$ (70 mL) at 0° C. was added triethylamine (3.54 mL, 25.4 mmol) and methanesulfonyl chloride (1.44 mL, 18.6 mmol). The mixture was warmed to rt and stirred for 3 h, at which point it was quenched with saturated aqueous sodium bicarbonate solution (100 mL). The aqueous phase was extracted with ethyl acetate (3×100 mL). The combined organic layer was washed with brine (50 mL), dried over anhydrous MgSO$_4$, filtered and concentrated under reduced pressure. The crude residue (a 3:1 mixture of (S)-(2-(1-((tert-butoxycarbonyl)amino)-2-methylpropyl)-5-chloropyridin-3-yl)methyl methanesulfonate and tert-butyl (S)-(1-(5-chloro-3-(chloromethyl)pyridin-2-yl)-2-methylpropyl)carbamate) was carried forward without any purification. LC-MS $t_R$=1.01 min in 1 min chromatography, MS (ESI) m/z 393.3 [M+H]$^+$. $^1$H NMR (CDCl$_3$, 400 MHz): δ 8.53 (d, J=2.4 Hz, 1H), 7.74 (d, J=2.8 Hz, 1H), 5.44 (d, J=12.4 Hz, 1H), 5.37 (d, J=12.8 Hz, 1H), 5.31 (d, J=8.4 Hz, 1H), 4.59 (t, J=9.2 Hz, 1H), 3.13 (s, 3H), 2.13-2.04 (m, 1H), 1.36 (s, 9H), 1.03 (d, J=6.8 Hz, 3H), 0.77 (d, J=6.8 Hz, 3H). Characterization data from a purified sample of (S)-(2-(1-((tert-butoxycarbonyl)amino)-2-methylpropyl)-5-chloropyridin-3-yl)methyl methanesulfonate.

Step 5: tert-butyl (S)-3-chloro-7-isopropyl-5,7-dihydro-6H-pyrrolo[3,4-b]pyridine-6-carboxylate To a solution of (S)-(2-(1-((tert-butoxycarbonyl)amino)-2-methylpropyl)-5-chloropyridin-3-yl)methyl methanesulfonate and tert-butyl (S)-(1-(5-chloro-3-(chloromethyl)pyridin-2-yl)-2-methylpropyl)carbamate (3:1 mixture, 6.39 g, 16.9 mmol) in THF (75 mL) at 0° C. was added sodium hydride (60% dispersion in mineral oil, 811 mg, 20.3 mmol). The mixture was warmed to rt and stirred for 15 h, at which point it was quenched with saturated aqueous ammonium chloride solution (100 mL). The aqueous phase was extracted with ethyl acetate (3×100 mL). The combined organic layer was washed with brine (50 mL), dried over anhydrous MgSO$_4$, filtered and concentrated under reduced pressure. The residue was purified by silica gel chromatography (eluting with 5% EtOAc in hexanes, gradient to 10%) to give tert-butyl (S)-3-chloro-7-isopropyl-5,7-dihydro-6H-pyrrolo[3,4-b]pyridine-6-carboxylate (4.31 g, 85% yield over 3 steps) as a yellow oil. LC-MS $t_R$=1.12 min in 1 min chromatography, MS (ESI) m/z 297.3 [M+H]$^+$. $^1$H NMR (CDCl$_3$, 400 MHz, mixture of rotamers): δ 8.43 (s, 1H), 7.56 (s, 0.6H), 7.50 (s, 0.4H), 4.96 (s, 0.4H), 4.87 (s, 0.6H), 4.86 (d, J=16.0 Hz, 0.6H), 4.74 (d, J=15.6 Hz, 0.4H), 4.52 (d, J=12.0 Hz, 0.4H), 4.49 (d, J=15.2 Hz, 0.6H), 2.60-2.51 (m, 0.4H), 2.40-2.36 (m, 0.6H), 1.49 (s, 9H), 1.08 (d, J=7.2 Hz, 1.2H), 0.99 (d, J=7.2 Hz, 1.8H), 0.78 (d, J=6.8 Hz, 1.8H), 0.72 (d, J=6.8 Hz, 1.2H).

Step 6: tert-butyl (S)-3-chloro-7-isopropyl-5,7-dihydro-6H-pyrrolo[3,4-b]pyridine-6-carboxylate Potassium carbonate (758 mg, 5.49 mmol) and 4 Å molecular sieves (250 mg) were placed in a 50 mL round-bottom flask which was then flame dried. Palladium (II) acetate (32.8 mg, 146 µmol) and 1,3-bis(dicyclohexylphosphonium)propane bis (tetrafluoroborate) (179 mg, 292 µmol) were added to the flask, which was then sealed with a septum. Tert-butyl (S)-3-chloro-7-isopropyl-5,7-dihydro-6H-pyrrolo[3,4-b]pyridine-6-carboxylate (1.09 g, 3.66 mmol) was dissolved in DMF (12 mL) and added to the flask, followed by 1-butanol (3.34 mL, 36.6 mmol). The flask was then evacuated and backfilled with CO three times, with the final time under a balloon of 1 atm of CO. The flask was heated to 100° C. and stirred for 6 h. The mixture was then cooled to rt and quenched with 1 N NaOH (25 mL). The mixture was stirred for 30 min, at which point isopropyl acetate (50 mL) was added. The phases were separated, then the organic phase was extracted with 1 N NaOH (2×50 mL), then the combined aqueous layer was acidified to pH=2 with concentrated HCl. The aqueous layer was then extracted with EtOAc (3×25 mL), then the combined organic layer was dried over anhydrous MgSO$_4$, filtered and concentrated under reduced pressure. The crude residue (S)-6-(tert-butoxycarbonyl)-7-isopropyl-6,7-dihydro-5H-pyrrolo[3,4-b]pyridine-3-carboxylic acid was carried forward without any purification.

Preparation A2: (S)-6-(tert-butoxycarbonyl)-7-ethyl-6,7-dihydro-5H-pyrrolo[3,4-b]pyridine-3-carboxylic acid

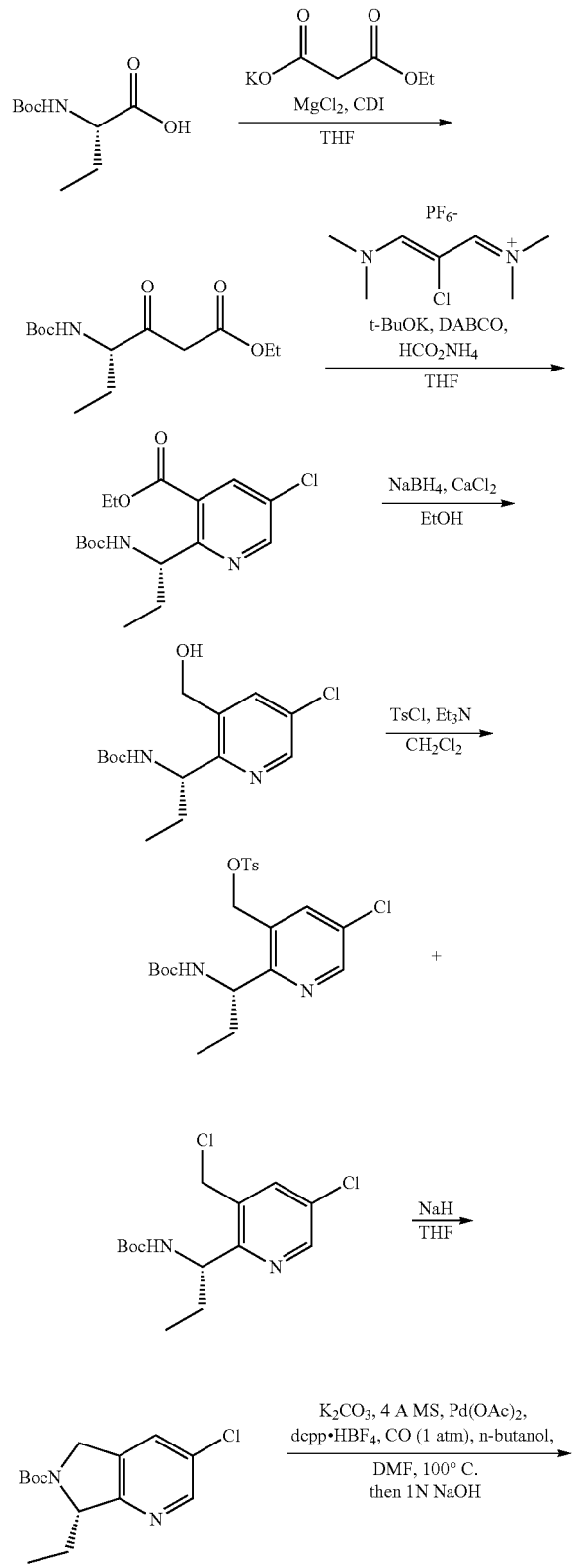

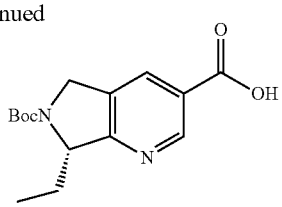

A2

Step 1: (S)-methyl 4-((tert-butoxycarbonyl)amino)-3-oxohexanoate

To a mixture of (S)-2-((tert-butoxycarbonyl)amino)butanoic acid (200 g, 0.985 mol) in THF (1 L) was added 1,1'-carbonyldiimidazole (176 g, 1.084 mol) at rt. The mixture was stirred at rt for 1 h. Then magnesium chloride (101 g, 1.084 mol) and potassium 3-methoxy-3-oxopropanoate (169 g, 1.084 mol) were added. After addition, the mixture was stirred at 50° C. for 3 h. TLC (petroleum ether:ethyl acetate=5:1) showed the starting material was consumed. The mixture was cooled and filtered; the filter cake was washed with THF (300 mL) and filtered. The combined filtrate was concentrated under reduced pressure and the residue was diluted with EtOAc (1 L) washed with water (800 mL), brine (800 mL), dried over anhydrous sodium sulfate, filtered and concentrated under reduced pressure to give (S)-methyl 4-((tert-butoxycarbonyl)amino)-3-oxohexanoate (117 g, 45%) as a yellow oil, which was used in the next step directly without further purification.

Step 2: (S)-methyl 2-(1-((tert-butoxycarbonyl)amino)propyl)-5-chloronicotinate To a solution of (S)-methyl 4-((tert-butoxycarbonyl)amino)-3-oxohexanoate (117 g, 0.452 mol) in anhydrous THF (1.0 L) was added potassium tert-butoxide (51.3 g, 0.474 mol) in portions at 0° C. After stirring for 1 h at 0° C., 1,4-diazabicyclo[2.2.2]octane (53.1 g, 0.474 mol) and 2-chloro-1,3-bis(dimethylamino)trimethinium hexafluorophosphate (145 g, 0.474 mol) were added portionwise to the mixture at 0° C. The mixture was stirred at rt for 3 h and the solution turned red. Ammonium acetate (104 g, 1.355 mol) was added to the solution, and the resulting mixture was stirred at rt overnight. TLC (petroleum ether:ethyl acetate=5:1) showed no starting material remaining. The mixture was cooled and filtered; the filtrate was concentrated under reduced pressure and the residue was diluted with EtOAc (1.5 L) and washed with water (1 L), brine (1 L), dried over anhydrous sodium sulfate, filtered and concentrated under reduced pressure. The residue was purified by silica gel chromatography, eluting with petroleum ether:ethyl acetate=25:1-17:1 to give (S)-methyl 2-(1-((tert-butoxycarbonyl)amino)propyl)-5-chloronicotinate (53 g, 36%) as a yellow oil. LC-MS $t_R$=0.961 min in 5-95AB_1.5 min chromatography (Merck RP-18e 25-2 mm), MS (ESI) m/z 272.9 [M−55]$^+$. $^1$H NMR (CDCl$_3$, 400 MHz): δ 8.61 (d, J=2.4 Hz, 1H), 8.18 (d, J=2.4 Hz, 1H), 5.71-5.54 (m, 1H), 3.94 (s, 3H), 1.86-1.83 (m, 1H), 1.60-1.58 (m, 1H), 1.26 (s, 9H), 0.95 (t, J=7.2 Hz, 3H).

Step 3: (S)-tert-butyl (1-(5-chloro-3-(hydroxymethyl)pyridin-2-yl)propyl)carbamate To a solution of (S)-methyl 2-(1-((tert-butoxycarbonyl)amino)propyl)-5-chloronicotinate (60 g, 0.183 mol) in anhydrous ethanol (800 mL) was added sodium borohydride portionwise (14.0 g, 0.366 mol) at 0° C. slowly and stirred for about 20 min To the resulting mixture was added calcium chloride (20.1 g, 0.183 mol) at 0° C. slowly in four portions. The mixture was stirred at 0° C. for 1.5 h. TLC (petroleum ether:ethyl acetate=5:1) showed no starting material remaining. The mixture was quenched with saturated aqueous $NH_4Cl$ solution (50 mL) at 0° C. slowly and then stirred for 30 min. The mixture was concentrated to remove part of the ethanol, then extracted with ethyl acetate (3×1.0 L). The combined organic layers were washed with water (2×1.0 L) and saturated aqueous $NaHCO_3$ solution (500 mL), dried over anhydrous sodium sulfate, filtered and concentrated under reduced pressure to give (S)-tert-butyl (1-(5-chloro-3-(hydroxymethyl)pyridin-2-yl)propyl)carbamate (50 g, 91%) as a yellow solid, which was used directly for the next step without further purification. LC-MS $t_R$=0.703 min in 5-95AB_1.5 min chromatography (Merck RP-18e 25-2 mm), MS (ESI) m/z 244.9 $[M-55]^+$.

Step 4: (S)-tert-butyl (1-(5-chloro-3-(chloromethyl)pyridin-2-yl)propyl)carbamate & (S)-(2-(1-((tert-butoxycarbonyl)amino)propyl)-5-chloropyridin-3-yl)methyl 4-methylbenzenesulfonate To a solution of (S)-tert-butyl (1-(5-chloro-3-(hydroxymethyl)pyridin-2-yl)propyl)carbamate (50 g, 0.167 mol) in $CH_2Cl_2$ (500 mL) was added triethylamine (50.5 g, 0.499 mol) and p-toluenesulfonyl chloride (63 g, 0.333 mol) at 0° C. The mixture was stirred at rt for 1.5 h. TLC (petroleum ether:ethyl acetate=5:1) showed no starting material remaining. The mixture was diluted with $CH_2Cl_2$ (500 mL), washed with water (2×1.0 L) and brine (1 L), dried over anhydrous $Na_2SO_4$, filtered and concentrated under reduced pressure. The residue was purified by silica gel chromatography (eluting with petroleum ether:ethyl acetate=0 to 10:1) to give (S)-tert-butyl (1-(5-chloro-3-(chloromethyl)pyridin-2-yl)propyl)carbamate (11 g, 21%) as a red solid and (S)-(2-(1-((tert-butoxycarbonyl)amino)propyl)-5-chloropyridin-3-yl)methyl 4-methylbenzenesulfonate (23 g, 30%) as a yellow solid. LC-MS $t_R$=0.840 min in 5-95AB_1.5 min chromatography (Merck RP-18e 25-2 mm), MS (ESI) m/z 262.9 $[M-55]^+$.

Step 5: (S)-tert-butyl 3-chloro-7-ethyl-5H-pyrrolo[3,4-b]pyridine-6(7H)-carboxylate Procedure same as that for tert-butyl (S)-3-chloro-7-isopropyl-5,7-dihydro-6H-pyrrolo[3,4-b]pyridine-6-carboxylate with (S)-tert-butyl (1-(5-chloro-3-(chloromethyl)pyridin-2-yl) propyl)carbamate (11 g, 34.6 mmol) and (S)-(2-(1-((tert-butoxycarbonyl)amino)propyl)-5-chloropyridin-3-yl)methyl 4-methylbenzenesulfonate as the starting materials. $^1$H NMR ($CDCl_3$, 400 MHz): δ 8.45 (s, 1H), 7.56 (s, 0.6H), 7.50 (s, 0.4H), 5.30 (s, 0.4H), 4.94 (s, 0.6H), 4.77 (d, J=15.6 Hz, 0.6H), 4.70 (d, J=15.6 Hz, 0.4H), 4.55 (s, 0.6H), 4.51 (s, 0.4H), 2.26-2.14 (m, 1H), 2.04-1.96 (m, 1H), 1.51 (s, 9H), 0.67 (t, J=7.6 Hz, 3H).

Step 6: (S)-6-(tert-butoxycarbonyl)-7-ethyl-6,7-dihydro-5H-pyrrolo[3,4-b]pyridine-3-carboxylic acid Potassium carbonate (33.8 g, 24.5 mmol) and 4 Å molecular sieves (11.30 g) were placed in a 50 mL round-bottom flask which was then flame dried. Palladium (II) acetate (757 mg, 3.26 mmol) and 1,3-bis(dicyclohexylphosphonium)propane bis(tetrafluoroborate) (3.98 g, 6.52 mmol) were added to the flask, which was then sealed with a septum. (S)-tert-butyl 3-chloro-7-ethyl-5H-pyrrolo[3,4-b]pyridine-6(7H)-carboxylate (23 g, 81.5 mmol) was dissolved in DMF (250 mL) and added to the flask, followed by 1-butanol (60.4 g, 815 mmol). The flask was then evacuated and backfilled with CO four times. CO gas (from a gas bag, a volume of 30 L) was then bubbled into the flask, with heating to 100° C. overnight. LCMS showed no starting material remaining. The reaction was then cooled to rt and 6 g of NaOH in 100 ml water was added. After stirring for 1 h, LCMS showed a 100% conversion to the acid product. The mixture was acidified to pH=3-4 with 1 N HCl solution and extracted with ethyl acetate (3×1 L). The combined organic layers were washed with water (2×1 L) and brine (1 L), dried over anhydrous sodium sulfate, filtered and concentrated under reduced pressure. The residue was purified by silica gel chromatography (eluting with petroleum ether:ethyl acetate=20:1-1:1) to give the desired product (20 g, 84%, ee=28.24%), which was then purified by SFC separation to give (S)-6-(tert-butoxycarbonyl)-7-ethyl-6,7-dihydro-5H-pyrrolo[3,4-b]pyridine-3-carboxylic acid (9 g, ee=95.49%) as a yellow solid. LC-MS $t_R$=0.813 min in 5-95AB_1.5 min chromatography (Merck RP-18e 25-2 mm), MS (ESI) m/z 292.9 $[M+H]^+$. $^1$H NMR ($CDCl_3$, 400 MHz): δ 9.23 (s, 1H), 7.28 (s, 0.6H), 8.23 (s, 0.4H), 5.21 (s, 0.4H), 5.11 (s, 0.6H), 4.89 (d, J=16.0 Hz, 0.6H), 4.80 (d, J=15.6 Hz, 0.4H), 4.65 (s, 0.6H), 4.61 (s, 0.4H), 2.25-2.14 (m, 1H), 2.08-2.04 (m, 1H), 1.53 (s, 9H), 0.68 (t, J=7.6 Hz, 3H). Isomer SFC 1215-186-P1A_1 $t_R$=6.71 in 15 min chromatography (Column: AD-H, Method Name: 5-40_2.5 ml.met, ee=95.49%).

Preparation A3: (S)-6-(tert-butoxycarbonyl)-7-(tetrahydro-2H-pyran-4-yl)-6,7-dihydro-5H-pyrrolo[3,4-b]pyridine-3-carboxylic acid

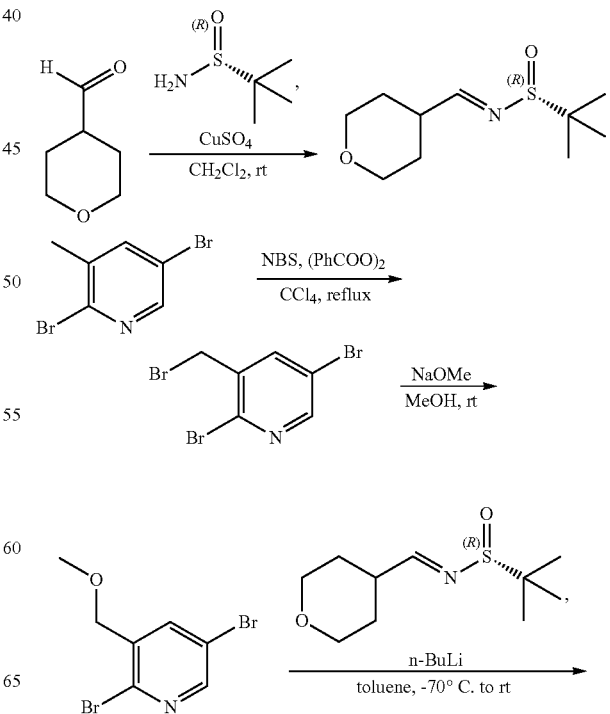

-continued

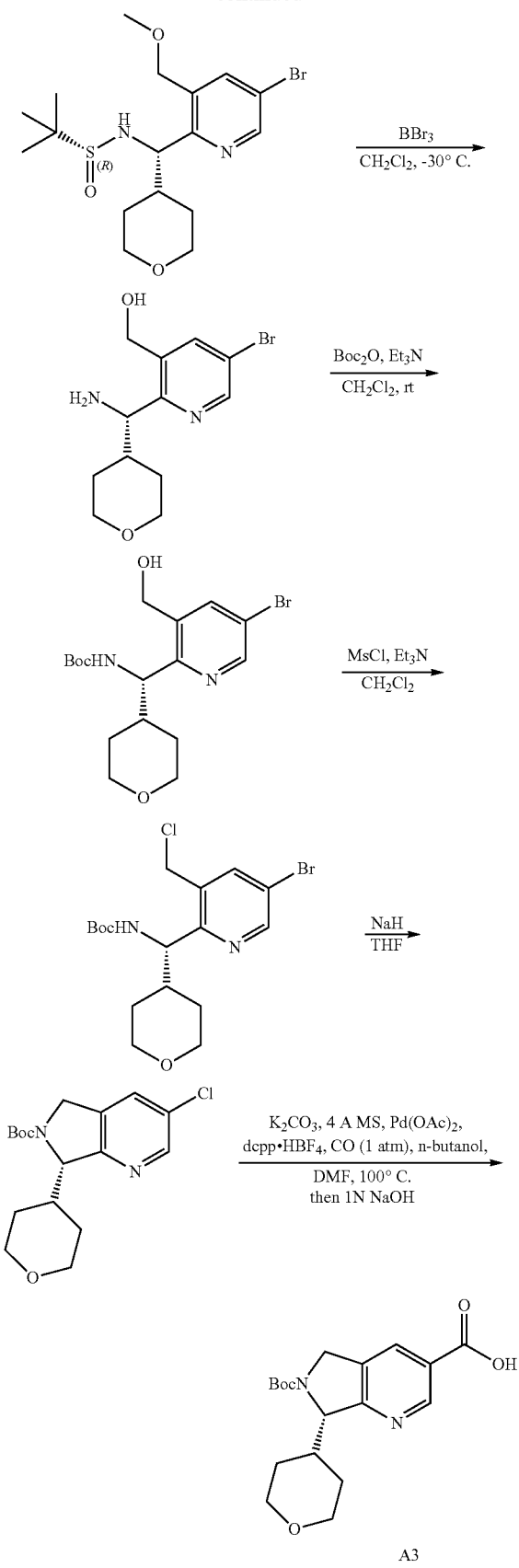

Step 1: (R,E)-2-methyl-N-((tetrahydro-2H-pyran-4-yl)methylene)propane-2-sulfinamide Procedure same as that for (R,E)-N-(2-((tert-butyldimethylsilyl)oxy)ethylidene)-2-methylpropane-2-sulfinamide with tetrahydro-2H-pyran-4-carbaldehyde and (R)-2-methylpropane-2-sulfinamide as the starting martials. LC-MS $t_R$=1.072 min in 5-95AB_1.5 min chromatography (Merck RP-18e 25-2 mm), MS (ESI) m/z 217.9 [M+H]$^+$.

Step 2: 2,5-dibromo-3-(bromomethyl)pyridine

A mixture of 2,5-dibromo-3-methylpyridine (20.0 g, 80.0 mmol), N-bromosuccinimide (12.8 g, 72 mmol) and benzoyl peroxide (1.03 g, 4 mmol) in CCl$_4$ (300 mL) was heated to reflux for 3 h. The mixture was cooled to rt, washed with water (2×100 mL) and brine (100 mL), dried over anhydrous sodium sulfate, filtered and concentrated under vacuum. The residue was purified by preparative HPLC (HCl) to give 2,5-dibromo-3-(bromomethyl)pyridine (11.0 g, 42%) as a white solid. $^1$H NMR: (CDCl$_3$, 400 MHz): δ 8.38-8.39 (d, J=2.4 Hz, 1H), 7.91-7.92 (d, J=2.4 Hz, 1H), 4.51 (s, 2H).

Step 3: 2,5-dibromo-3-(methoxymethyl)pyridine

A mixture of 2,5-dibromo-3-(bromomethyl)pyridine (11.0 g, 33.3 mmol) and sodium methoxide (5.4 g, 100 mmol) in methanol (150 mL) was stirred at rt for 18 h. The mixture was filtered and the filtrate was concentrated under vacuum. The residue was purified by silica gel chromatography (eluting with petroleum ether:ethyl acetate=10:1) to give 2,5-dibromo-3-(methoxymethyl)pyridine (8.7 g, 93%) as a liquid. $^1$H NMR (CDCl$_3$, 400 MHz): δ 8.35 (s, 1H), 7.93 (s, 1H), 4.45 (s, 2H), 3.53 (s, 3H).

Step 4: (R)—N—((S)-(5-bromo-3-(methoxymethyl)pyridin-2-yl)(tetrahydro-2H-pyran-4-yl)methyl)-2-methylpropane-2-sulfinamide & (R)—N—((R)-(5-bromo-3-(methoxymethyl)pyridin-2-yl)(tetrahydro-2H-pyran-4-yl)methyl)-2-methylpropane-2-sulfinamide Procedure same as that for (R)—N—((R)-2-((tert-butyldimethylsilyl)oxy)-1-(4-(ethylthio)phenyl)ethyl)-2-methylpropane-2-sulfinamide with 2,5-dibromo-3-(methoxymethyl)pyridine and (R)-tert-butylsulfonamide as the starting materials. LC-MS $t_R$=0.824 min in 5-95AB_1.5 min chromatography (Merck RP-18e 25-2 mm), MS (ESI) 420.9 [M+1]$^+$. Isomer SFC $t_R$=11.19 and 11.71 in 25 min chromatography (Column: AS-RH_10-80_B_08 ML_25 MIN), ee=97.16%.

Step 5: (S)-(2-(amino(tetrahydro-2H-pyran-4-yl)methyl)-5-bromopyridin-3-yl)methanol To a solution of (R)—N—((S)-(5-bromo-3-(methoxymethyl)pyridin-2-yl) (tetrahydro-2H-pyran-4-yl)methyl)-2-methylpropane-2-sulfinamide (1.5 g, 3.6 mmol) in CH$_2$Cl$_2$ (30 mL) was added boron tribromide (4.5 g, 18.0 mmol) at −30° C. The mixture was stirred at −30° C. for 2 h. MeOH (5 mL) was then carefully added to the mixture at −30° C. and the reaction was allowed to warm to rt. Upon reaching rt, the mixture was concentrated under reduced pressure to afford crude (S)-(2-(amino(tetrahydro-2H-pyran-4-yl)methyl)-5-bromopyridin-3-yl)methanol (1.0 g, crude) as an oil, which was used for the next step without further

Step 6: (S)-tert-butyl ((5-bromo-3-(hydroxymethyl)pyridin-2-yl)(tetrahydro-2H-pyran-4-yl)methyl)carbamate A mixture of (S)-(2-(amino(tetrahydro-2H-pyran-4-yl)methyl)-5-bromopyridin-3-yl)methanol (1.0 g, 3.3 mmol), di-tert-butyl dicarbonate (1.1 g, 5.0 mmol) and triethylamine (1.0 g, 10 mmol) in $CH_2Cl_2$ (10 mL) was stirred at rt for 16 h. The mixture was quenched with water (10 mL) and extracted with $CH_2Cl_2$ (3×10 mL). The combined organic layer was washed with brine (2×10 mL), dried over anhydrous $Na_2SO_4$, filtered and concentrated under reduced pressure. The residue was purified by silica gel chromatography (eluting with petroleum ether:ethyl acetate=5:1-3:1) to give (S)-tert-butyl ((5-bromo-3-(hydroxymethyl)pyridin-2-yl)(tetrahydro-2H-pyran-4-yl)methyl)carbamate (500 mg, 38%) as an oil. LC-MS $t_R$=2.870 min in 0-30CD_POS.M chromatography (Merck RP-18e 25-2 mm), MS (ESI) m/z 401.1 [M+1]$^+$.

Step 7: (S)-tert-butyl ((5-bromo-3-(chloromethyl)pyridin-2-yl)(tetrahydro-2H-pyran-4-yl)methyl)carbamate Procedure same as that for (S)-(2-(1-((tert-butoxycarbonyl)amino)-2-methylpropyl)-5-chloropyridin-3-yl)methyl methanesulfonate with (S)-tert-butyl ((5-bromo-3-(hydroxymethyl)pyridin-2-yl)(tetrahydro-2H-pyran-4-yl)methyl)carbamate as the starting material. LC-MS $t_R$=0.943 min in 5-95AB_1.5 min chromatography (Merck RP-18e 25-2 mm), MS (ESI) m/z 365.0 [M+1]$^+$.

Step 8: (S)-tert-butyl 3-bromo-7-(tetrahydro-2H-pyran-4-yl)-5H-pyrrolo[3,4-b]pyridine-6(7H)-carboxylate Procedure same as that for tert-butyl (S)-3-chloro-7-isopropyl-5,7-dihydro-6H-pyrrolo[3,4-b]pyridine-6-carboxylate with (S)-tert-butyl ((5-bromo-3-(chloromethyl)pyridin-2-yl) (tetrahydro-2H-pyran-4-yl)methyl)carbamate (350 mg, 0.83 mmol) as the starting material. LC-MS $t_R$=1.723 min in 5-95AB_1.5 min chromatography (Merck RP-18e 25-2 mm), MS (ESI) m/z 385.1 [M+1]$^+$. Isomer SFC $t_R$=2.930 and 4.433 in 12 min chromatography (Column: AD_3_B2_5_40_25 ML), ee=97.80%.

Step 9: (S)-6-(tert-butoxycarbonyl)-7-(tetrahydro-2H-pyran-4-yl)-6,7-dihydro-5H-pyrrolo[3,4-b]pyridine-3-carboxylic acid Procedure same as that for (S)-6-(tert-butoxycarbonyl)-7-isopropyl-6,7-dihydro-5H-pyrrolo[3,4-b]pyridine-3-carboxylic acid with (S)-tert-butyl 3-bromo-7-(tetrahydro-2H-pyran-4-yl)-5H-pyrrolo[3,4-b]pyridine-6(7H)-carboxylate as the starting material. LC-MS $t_R$=0.685 min in 5-95AB_1.5 min chromatography (Merck RP-18e 25-2 mm), MS (ESI) 349.1 [M+1]$^+$. Isomer SFC $t_R$=5.146 and 5.602 in 15 min chromatography (Column: AD-H_5_5_40_2.35 ML), ee=95.89%.

Preparation A4: (S)-6-(tert-butoxycarbonyl)-7-((tetrahydro-2H-pyran-4-yl)methyl)-6,7-dihydro-5H-pyrrolo[3,4-b]pyridine-3-carboxylic acid

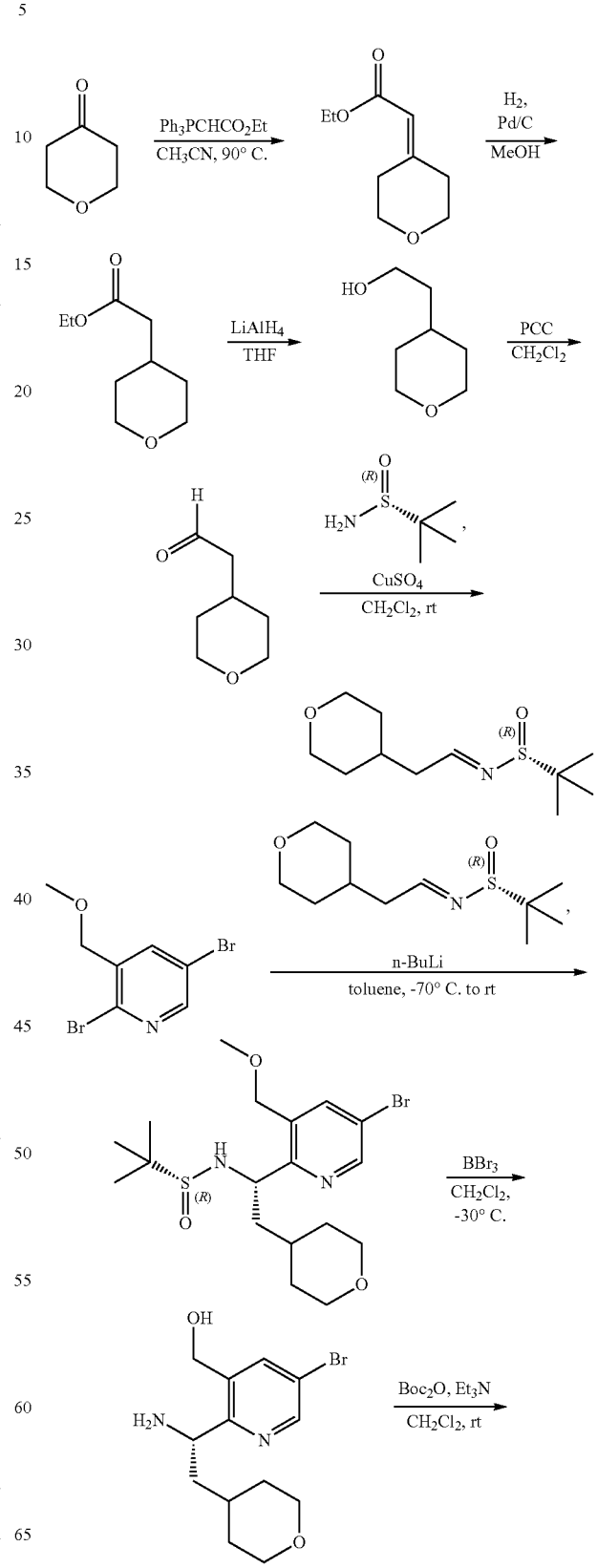

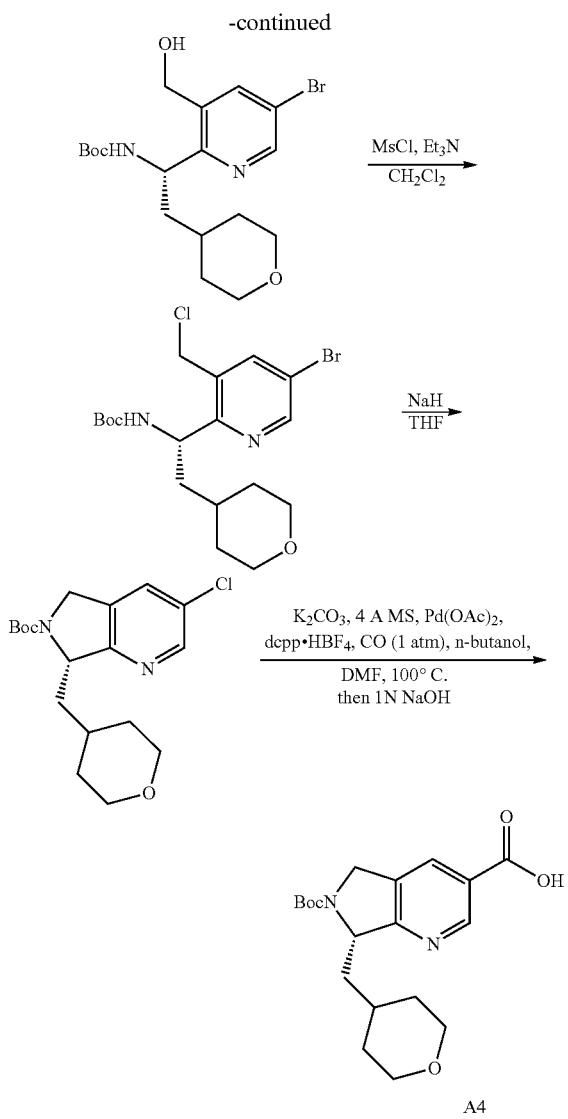

Step 1: ethyl 2-(dihydro-2H-pyran-4(3H)-ylidene)acetate

To a mixture of dihydro-2H-pyran-4(3H)-one (22.5 g, 225 mmol) in acetonitrile (500 mL) was added (carbethoxymethylene)triphenylphosphorane (86.1 g, 247 mmol) at 0° C. The mixture was stirred at 85-90° C. (oil bath) for 48 h. LCMS showed a strong product peak and most of (carbethoxymethylene)triphenylphosphorane consumed. The mixture was cooled to rt, filtered and concentrated under reduced pressure. The residue was purified by silica gel chromatography (eluting with petroleum ether:ethyl acetate=10:1) to give ethyl 2-(dihydro-2H-pyran-4(3H)-ylidene)acetate (38 g, 99%) as a yellow solid. $^1$H NMR (CDCl$_3$, 400 MHz): δ 5.66 (s, 1H), 4.09-4.14 (q, J=7.2 Hz, 2H), 3.71-3.77 (m, 4H), 2.98-3.01 (t, J=5.2 Hz, 2H), 2.30-2.32 (t, J=4.8 Hz, 2H), 1.24-1.28 (t, J=7.2 Hz, 3H).

Step 2: ethyl 2-(tetrahydro-2H-pyran-4-yl)acetate

A mixture of ethyl 2-(dihydro-2H-pyran-4(3H)-ylidene) acetate (21 g, 123 mmol) and dry Pd/C (2.5 g) in methanol (300 mL) was stirred at 16-19° C. for 18 h under H$_2$ (30 psi). TLC (petroleum ether:ethyl acetate=3:1) showed no starting material remaining. The mixture was filtered and the filtrate was concentrated under reduced pressure to give crude ethyl 2-(tetrahydro-2H-pyran-4-yl)acetate (20 g, 94%) as an oil, which was used for the next step directly without further purification. $^1$H NMR (CDCl$_3$, 400 MHz): δ 4.11-4.15 (q, J=7.2 Hz, 2H), 3.93-3.95 (d, J=10.8 Hz, 2H), 3.37-3.43 (t, J=11.6 Hz, 2H), 2.23-2.25 (d, J=6.8 Hz, 2H), 1.99-2.03 (m, 1H), 1.62-1.65 (m, 2H), 1.32-1.36 (m, 2H), 1.24-1.27 (t, J=7.2 Hz, 3H).

Step 3: 2-(tetrahydro-2H-pyran-4-yl)ethanol

To a mixture of ethyl 2-(tetrahydro-2H-pyran-4-yl)acetate (20 g, 116 mmol) in anhydrous THF (300 mL) was added lithium aluminum hydride (8.8 g, 232 mmol) portionwise at 0° C. The mixture was stirred at 11-13° C. for 18 h. TLC (petroleum ether: ethyl acetate=3:1) showed no starting material remaining. The mixture was quenched with water (9 mL), 10% aq. NaOH solution (9 mL) and water (18 mL) successively at 0° C., filtered and concentrated under reduced pressure to give crude 2-(tetrahydro-2H-pyran-4-yl)ethanol (11.7 g, 77%) as an oil, which was used for the next step directly without further purification. $^1$H NMR (CDCl$_3$, 400 MHz): δ 3.86-3.90 (m, 2H), 3.58-3.61 (t, J=6.4 Hz, 2H), 3.32-3.35 (t, J=11.6 Hz, 2H), 2.69-2.70 (m, 1H), 1.61-1.63 (m, 3H), 1.54-1.60 (m, 2H), 1.43-1.45 (m, 2H).

Step 4: 2-(tetrahydro-2H-pyran-4-yl)acetaldehyde

A mixture of 2-(tetrahydro-2H-pyran-4-yl)ethanol (11.70 g, 89.9 mmol) and pyridinium chlorochromate (38.8 g, 179.8 mmol) in CH$_2$Cl$_2$ (200 mL) was stirred at 16-19° C. for 17 h. TLC (petroleum ether:ethyl acetate=3:1) showed the reaction was complete. The mixture was filtered with Kieselguhr and the filtrate (150 mL) was used for the next step directly without further purification.

Step 5: (R,E)-2-methyl-N-(2-(tetrahydro-2H-pyran-4-yl)ethylidene)propane-2-sulfinamide Procedure same as that for (R,E)-N-(2-((tert-butyldimethylsilyl)oxy)ethylidene)-2-methylpropane-2-sulfinamide with 2-(tetrahydro-2H-pyran-4-yl)acetaldehyde and (R)-2-methylpropane-2-sulfinamide (21.8 g, 179.8 mmol) as the starting materials. LC-MS t$_R$=1.082 min in 10-80AB_2.0 min chromatography (Xtimate 3 um, C18, 2.1*30 mm), MS (ESI) m/z 232.0 [M+H]$^+$. $^1$H NMR (CDCl$_3$, 400 MHz): δ 8.06-8.09 (t, J=5.2 Hz, 1H), 3.38-3.44 (m, 4H), 2.47-2.50 (m, 2H), 2.29-2.31 (m, 1H), 1.62-1.68 (m, 4H).

Step 6: (R)—N—((S)-1-(5-bromo-3-(methoxymethyl)pyridin-2-yl)-2-(tetrahydro-2H-pyran-4-yl)ethyl)-2-methylpropane-2-sulfinamide and (R)—N—((R)-1-(5-bromo-3-(methoxymethyl)pyridin-2-yl)-2-(tetrahydro-2H-pyran-4-yl)ethyl)-2-methylpropane-2-sulfinamide Procedure same as that for (R)—N—((R)-2-((tert-butyldimethylsilyl)oxy)-1-(4-(ethylthio)phenyl)ethyl)-2-methylpropane-2-sulfinamide with 2,5-dibromo-3-(methoxymethyl)pyridine and (R,E)-2-methyl-N-(2-(tetrahydro-2H-pyran-4-yl)ethylidene)propane-2-sulfinamide as the starting materials. LC-MS t$_R$=0.849 min in 5-95AB_1.5 min chromatography (Merck RP-18e 25-2 mm), MS (ESI) m/z 433.0 [M+H]$^+$. Isomer SFC t$_R$=12.39 in 25 min chromatography (Column: AD-RH_10-80_B_08 ML_25 min), ee=97.16%. Another Isomer: LC-MS $t_R$=1.081 min in 10-80AB_2.0 min chromatography (Xtimate, 2.1*30 mm, 3 um), MS (ESI) m/z 433.0 [M+H]$^+$. Isomer SFC $t_R$=13.04 and 15.09 in 25 min chromatography (Column: AD-RH_10-80_B_08 ML_25 min), ee=96.46%.

Step 7: (S)-(2-(1-amino-2-(tetrahydro-2H-pyran-4-yl)ethyl)-5-bromopyridin-3-yl) methanol Procedure same as that for (S)-(2-(amino(tetrahydro-2H-pyran-4-yl)methyl)-5-bromopyridin-3-yl)methanol with (R)—N—((S)-1-(5-bromo-3-(methoxymethyl)pyridin-2-yl)-2-(tetrahydro-2H-pyran-4-yl)ethyl)-2-methylpropane-2-sulfinamide as the starting material. LC-MS $t_R$=0.307 min in 0-30AB_2.0 min chromatography (Xtimate, 2.1*30 mm, 3 um), MS (ESI) m/z 315.0 [M+H]$^+$.

Step 8: (S)-tert-butyl 1-(5-bromo-3-(hydroxymethyl)pyridin-2-yl)-2-(tetrahydro-2H-pyran-4-yl) ethylcarbamate Procedure same as that for (S)-tert-butyl ((5-bromo-3-(hydroxymethyl)pyridin-2-yl)(tetrahydro-2H-pyran-4-yl)methyl)carbamate with (S)-(2-(1-amino-2-(tetrahydro-2H-pyran-4-yl)ethyl)-5-bromopyridin-3-yl)methanol as the starting material. LC-MS $t_R$=0.716 min in 5-95AB_1.5 min chromatography (MK RP-18e 25-2 mm), MS (ESI) m/z 414.9 [M+H]$^+$.

Step 9: (S)-tert-butyl 1-(5-bromo-3-(chloromethyl)pyridin-2-yl)-2-(tetrahydro-2H-pyran-4-yl)ethylcarbamate Procedure same as that for (S)-(2-(1-(((tert-butoxycarbonyl)amino)-2-methylpropyl)-5-chloropyridin-3-yl)methyl methanesulfonate with (S)-tert-butyl 1-(5-bromo-3-(hydroxymethyl)pyridin-2-yl)-2-(tetrahydro-2H-pyran-4-yl) ethylcarbamate as the starting material. LC-MS $t_R$=0.962 min in 5-95AB_1.5 min chromatography (Merck RP-18e 25-2 mm), MS (ESI) m/z 434.9 [M+1]$^+$.

Step 10: (S)-tert-butyl 3-bromo-7-((tetrahydro-2H-pyran-4-yl)methyl)-5H-pyrrolo[3,4-b]pyridine-6 (7H)-carboxylate Procedure same as that for tert-butyl (S)-3-chloro-7-isopropyl-5,7-dihydro-6H-pyrrolo[3,4-b]pyridine-6-carboxylate with (S)-tert-butyl 1-(5-bromo-3-(chloromethyl)pyridin-2-yl)-2-(tetrahydro-2H-pyran-4-yl)ethylcarbamate as the starting material. LC-MS $t_R$=0.792 min in 5-95AB_1.5 min chromatography (MK RP-18e 25-2 mm), MS (ESI) m/z 396.9 [M+H]$^+$.

Step 11: (S)-6-(tert-butoxycarbonyl)-7-((tetrahydro-2H-pyran-4-yl)methyl)-6,7-dihydro-5H-pyrrolo[3,4-b]pyridine-3-carboxylic acid Procedure same as that for (S)-6-(tert-butoxycarbonyl)-7-isopropyl-6,7-dihydro-5H-pyrrolo[3,4-b]pyridine-3-carboxylic acid with (S)-tert-butyl 3-bromo-7-((tetrahydro-2H-pyran-4-yl)methyl)-5H-pyrrolo[3,4-b]pyridine-6(7H)-carboxylate as the starting material. LC-MS $t_R$=0.990 min in 10-80AB_2.0 min chromatography (Xtimate 3 um, C18, 2.1*30 mm), MS (ESI) m/z 363.1 [M+1]$^+$.

Preparation A5: (S)-7-benzyl-6-(tert-butoxycarbonyl)-6,7-dihydro-5H-pyrrolo[3,4-b]pyridine-3-carboxylic acid

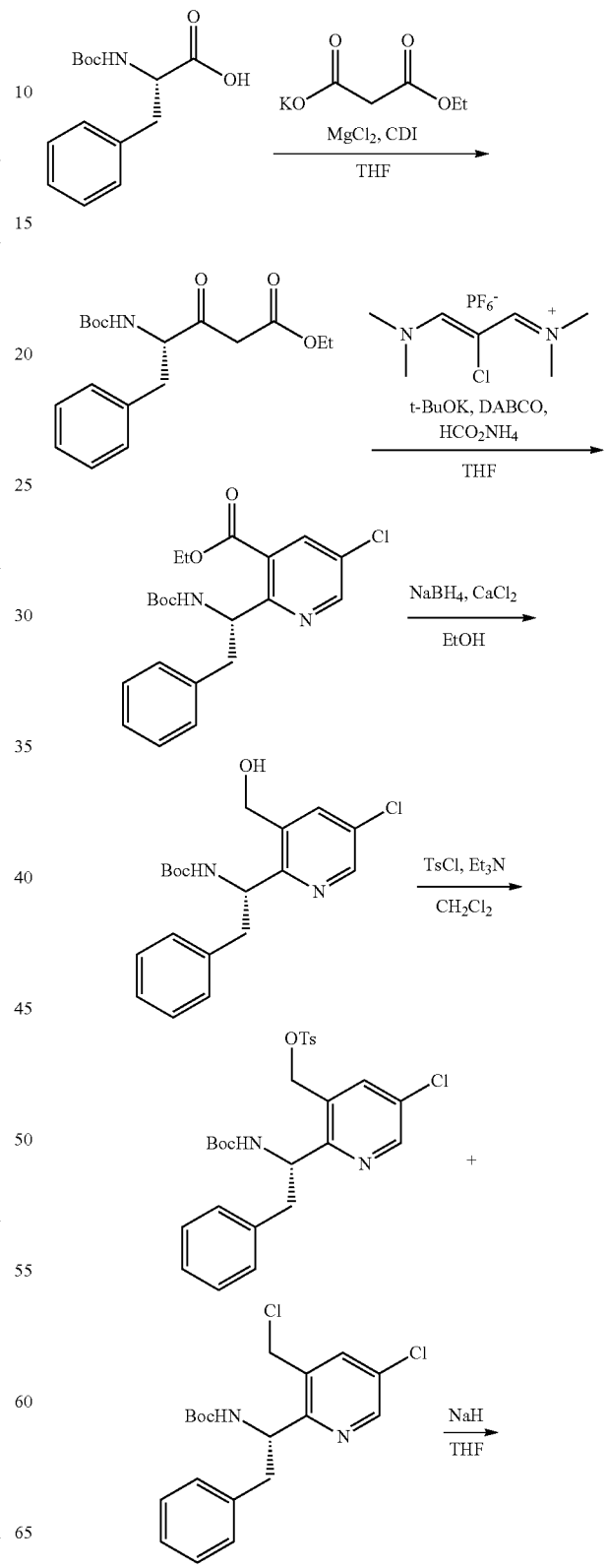

-continued

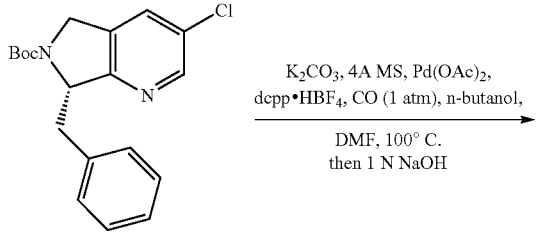

K₂CO₃, 4A MS, Pd(OAc)₂,
dcpp·HBF₄, CO (1 atm), n-butanol,
———————————————→
DMF, 100° C.
then 1 N NaOH

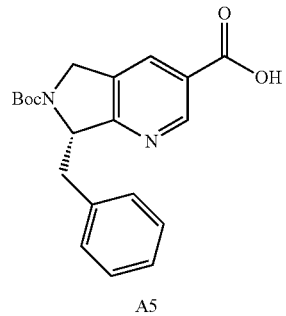

A5

Step 1: (S)-methyl 4-(tert-butoxycarbonylamino)-3-oxo-5-phenylpentanoate

Procedure same as that for ethyl (S)-4-((tert-butoxycarbonyl)amino)-5-methyl-3-oxohexanoate with (S)-2-(tert-butoxycarbonylamino)-3-phenylpropanoic acid as the starting material.

Step 2: (S)-methyl 2-(1-(tert-butoxycarbonylamino)-2-phenylethyl)-5-chloronicotinate Procedure same as that for (S)-2-(1-((tert-butoxycarbonyl)amino)-2-methylpropyl)-5-chloronicotinate with (S)-methyl 4-(tert-butoxycarbonylamino)-3-oxo-5-phenylpentanoate as the starting material. LC-MS $t_R$=1.007 min in 5-95AB_1.5 min chromatography (MK RP18e 25-2 mm), MS (ESI) m/z 335.1 [M-55]⁺.

Step 3: (S)-tert-butyl 1-(5-chloro-3-(hydroxymethyl)pyridin-2-yl)-2-phenylethylcarbamate Procedure same as that for tert-butyl (S)-(1-(5-chloro-3-(hydroxymethyl)pyridin-2-yl)-2-methylpropyl)carbamate with (S)-methyl 2-(1-(tert-butoxycarbonylamino)-2-phenylethyl)-5-chloronicotinate as the starting material. LC-MS $t_R$=0.812 min in 5-95AB_1.5 min chromatography (MK RP18e 25-2 mm), MS (ESI) m/z 362.9, 306.8 [M+H]⁺, [M-55]⁺.

Step 4: (S)-(2-(1-(tert-butoxycarbonylamino)-2-phenylethyl)-5-chloropyridin-3-yl) methyl 4-methylbenzenesulfonate Procedure same as that for (S)-(2-(1-((tert-butoxycarbonyl)amino)propyl)-5-chloropyridin-3-yl)methyl 4-methylbenzenesulfonate with (S)-tert-butyl 1-(5-chloro-3-(hydroxymethyl)pyridin-2-yl)-2-phenylethylcarbamate as the starting material. LC-MS $t_R$=1.069 min in 5-95AB_1.5 min chromatography (MK RP18e 25-2 mm), MS (ESI) m/z 539.1 [M+23]⁺.

Step 5: (S)-tert-butyl 7-benzyl-3-chloro-5H-pyrrolo[3,4-b]pyridine-6(7H)-carboxylate Procedure same as that for tert-butyl (S)-3-chloro-7-isopropyl-5,7-dihydro-6H-pyrrolo[3,4-b]pyridine-6-carboxylate with (S)-(2-(1-(tert-butoxycarbonylamino)-2-phenylethyl)-5-chloropyridin-3-yl)methyl 4-methylbenzenesulfonate as the starting material. LC-MS $t_R$=0.995 min in 5-95AB_1.5 min chromatography (MK RP18e 25-2 mm), MS (ESI) m/z 345.1 [M+H]⁺.

Step 6: (S)-7-benzyl-6-(tert-butoxycarbonyl)-6,7-dihydro-5H-pyrrolo[3,4-b]pyridine-3-carboxylic acid Procedure same as that for (S)-6-(tert-butoxycarbonyl)-7-isopropyl-6,7-dihydro-5H-pyrrolo[3,4-b]pyridine-3-carboxylic acid with (S)-tert-butyl 7-benzyl-3-chloro-5H-pyrrolo[3,4-b]pyridine-6(7H)-carboxylate as the starting material. LC-MS $t_R$=0.869 min in 5-95AB_1.5 min chromatography (MK RP18e 25-2 mm), MS (ESI) m/z 355.2 [M+H]⁺.

Preparation A6: 6-(tert-butoxycarbonyl)-7-methyl-6,7-dihydro-5H-pyrrolo[3,4-b]pyridine-3-carboxylic acid

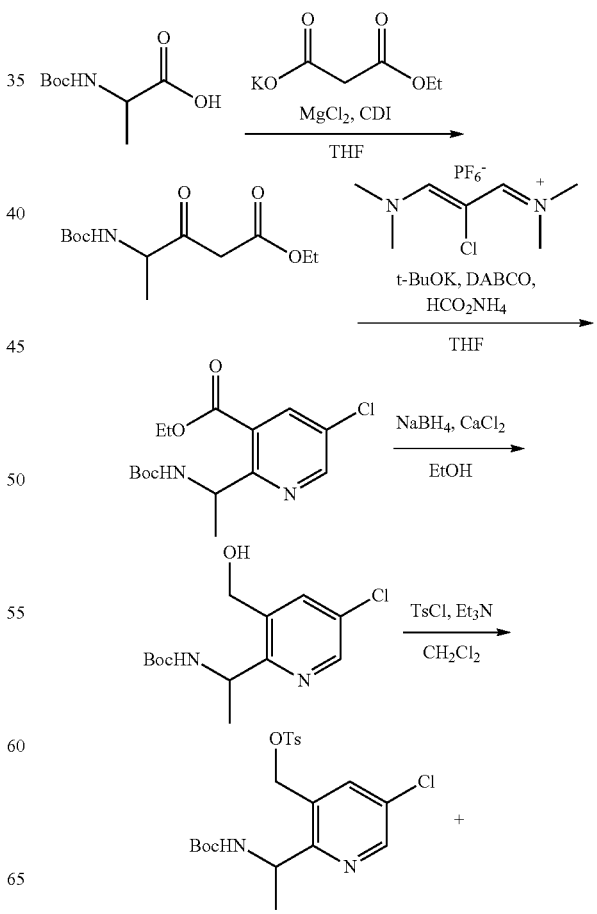

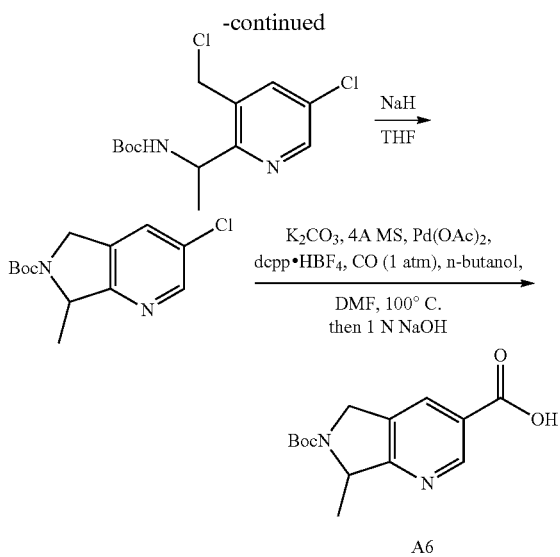

A6

Step 1: methyl 4-(tert-butoxycarbonylamino)-3-oxopentanoate

Procedure same as that for ethyl (S)-4-((tert-butoxycarbonyl)amino)-5-methyl-3-oxohexanoate with 2-(tert-butoxycarbonylamino)propanoic acid as the starting material. $^1$H NMR (CDCl$_3$, 400 MHz): δ 5.05-5.26 (m, 1H), 4.28-4.39 (m, 1H), 3.72 (s, 3H), 3.50-3.62 (m, 2H), 1.42 (s, 9H), 1.30-1.35 (d, J=7.2 Hz, 3H).

Step 2: methyl 2-(1-(tert-butoxycarbonylamino)ethyl)-5-chloronicotinate

Procedure same as that for (S)-2-(1-((tert-butoxycarbonyl)amino)-2-methylpropyl)-5-chloronicotinate with methyl 4-(tert-butoxycarbonylamino)-3-oxopentanoate as the starting material. $^1$H NMR (CDCl$_3$, 400 MHz): δ 8.57-8.68 (d, J=2.8 Hz, 1H), 8.14-8.24 (d, J=2.4 Hz, 1H), 5.55-5.91 (m, 2H), 3.95 (s, 3H), 1.34-1.47 (m, 12H). LCMS t$_R$=1.063 min in 10-80AB_2.0 min chromatography (Xbridge Shield RP18 2.1*50 mm), MS (ESI) m/z 315.1 [M+H]$^+$.

Step 3: tert-butyl 1-(5-chloro-3-(hydroxymethyl)pyridin-2-yl)ethylcarbamate

Procedure same as that for tert-butyl (S)-(1-(5-chloro-3-(hydroxymethyl)pyridin-2-yl)-2-methylpropyl)carbamate with methyl 2-(1-(tert-butoxycarbonylamino)ethyl)-5-chloronicotinate as the starting material. LCMS t$_R$=0.887 min in 10-80AB_2.0 min chromatography (Xbridge Shield RP18 2.1*50 mm), MS (ESI) m/z 287.1 [M+H]$^+$.

Step 4: tert-butyl 1-(5-chloro-3-(chloromethyl)pyridin-2-yl)ethylcarbamate

Procedure same as that for (S)-(2-(1-((tert-butoxycarbonyl)amino)propyl)-5-chloropyridin-3-yl)methyl 4-methylbenzenesulfonate with tert-butyl 1-(5-chloro-3-(hydroxymethyl)pyridin-2-yl)ethylcarbamate as the starting material. LCMS t$_R$=1.086 min in 10-80AB_2.0 min chromatography (Xbridge Shield RP18 2.1*50 mm), MS (ESI) m/z 305.1 [M+H]$^+$.

Step 5: tert-butyl 3-chloro-7-methyl-5H-pyrrolo[3,4-b]pyridine-6(7H)-carboxylate Procedure same as that for tert-butyl (S)-3-chloro-7-isopropyl-5,7-dihydro-6H-pyrrolo[3,4-b]pyridine-6-carboxylate with tert-butyl 1-(5-chloro-3-(chloromethyl)pyridin-2-yl)ethylcarbamate as the starting material. LCMS t$_R$=1.047 min in 10-80AB_2.0 min chromatography (Xbridge Shield RP18 2.1*50 mm), MS (ESI) m/z 269.1 [M+H]$^+$.

Step 6: 6-(tert-butoxycarbonyl)-7-methyl-6,7-dihydro-5H-pyrrolo[3,4-b]pyridine-3-carboxylic acid Procedure same as that for (S)-6-(tert-butoxycarbonyl)-7-isopropyl-6,7-dihydro-5H-pyrrolo[3,4-b]pyridine-3-carboxylic acid with tert-butyl 3-chloro-7-methyl-5H-pyrrolo[3,4-b]pyridine-6(7H)-carboxylate as the starting material. LCMS t$_R$=0.882 min in 10-80AB_2.0 min chromatography (Xbridge Shield RP18 2.1*50 mm), MS (ESI) m/z 279.1 [M+H]$^+$.

Preparation A7: (R)-6-(tert-butoxycarbonyl)-7-(((tert-butyldimethylsilyl)oxy)methyl)-6,7-dihydro-5H-pyrrolo[3,4-b]pyridine-3-carboxylic acid

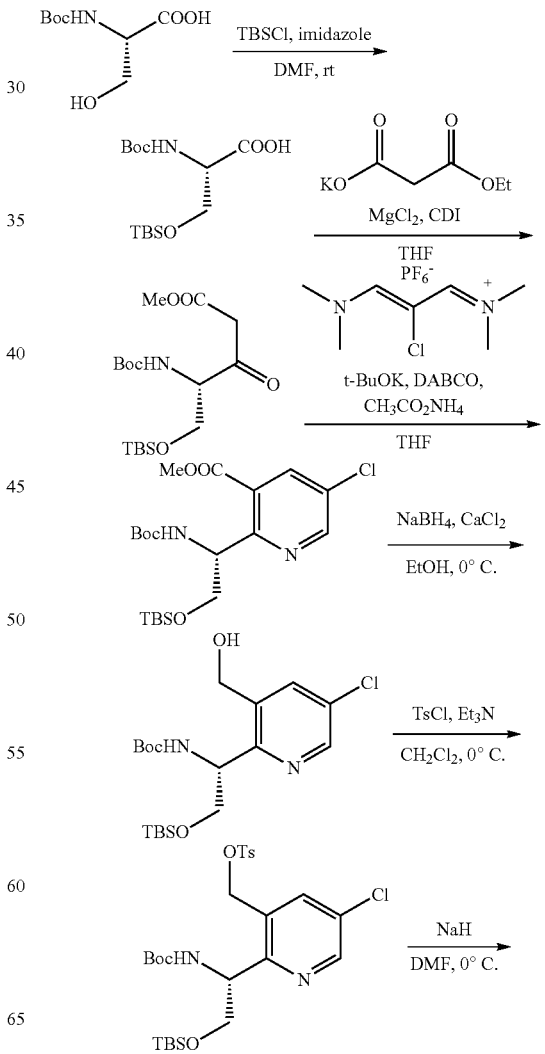

-continued

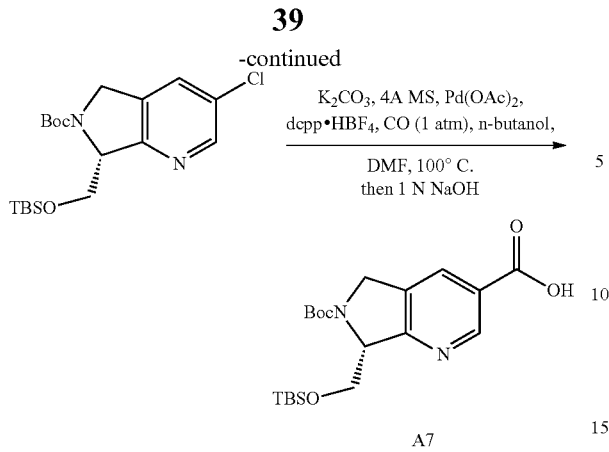

A7

Step 1: (S)-2-((tert-butoxycarbonyl)amino)-3-((tert-butyldimethylsilyl)oxy)propanoic acid To a solution of (S)-2-((tert-butoxycarbonyl)amino)-3-hydroxypropanoic acid (30 g, 0.146 mol) in anhydrous DMF (300 mL) was added tert-butylchlorodimethylsilane (21.90 g, 0.146 mol) and imidazole (19.80 g, 0.292 mol) at 0° C., then the mixture was stirred at rt for 18 h. The mixture was diluted with ethyl acetate (300 mL) and water (30 mL), extracted with ethyl acetate (3×300 mL), washed with water (2×1000 mL), brine (2×1000 mL), dried over anhydrous sodium sulfate, filtered and concentrated to give (S)-2-((tert-butoxycarbonyl)amino)-3-((tert-butyldimethylsilyl)oxy)propanoic acid (34 g, 72%) as a yellow oil. $^1$H NMR (CDCl$_3$, 400 MHz): δ 5.20-5.30 (m, 1H), 4.25-4.35 (m, 1H), 4.01-4.15 (m, 1H), 3.75-3.85 (m, 1H), 1.40 (s, 9H), 0.82 (s, 9H), 0.01 (s, 6H).

Step 2: (S)-methyl 4-((tert-butoxycarbonyl)amino)-5-((tert-butyldimethylsilyl)oxy)-3-oxopentanoate A mixture of (S)-2-((tert-butoxycarbonyl)amino)-3-((tert-butyldimethylsilyl)oxy)propanoic acid (24.0 g, 75.2 mmol), 1,1'-carbonyldiimidazole (14.6 g, 90.2 mmol) in THF (250 mL) was stirred at rt for 1 h. Then potassium 3-methoxy-3-oxopropanoate (11.70 g, 75.2 mmol) and magnesium chloride (7.14 g, 75.2 mmol) were added. After addition, the mixture was stirred at 50° C. for 16 h. TLC (petroleum ether:ethyl acetate=5:1) showed the starting material was consumed. The mixture was quenched with water (200 mL) and extracted with ethyl acetate (3×150 mL). The combined organic layers were washed with saturated aqueous NaHCO$_3$ solution (500 mL) and brine (500 mL), dried over anhydrous sodium sulfate, filtered and concentrated under reduced pressure to give (S)-methyl 4-((tert-butoxycarbonyl)amino)-5-((tert-butyldimethylsilyl)oxy)-3-oxopentanoate (28 g, 100% crude) as a yellow oil, which was used for the next step directly without further purification. LCMS $t_R$=1.282 min in 10-80AB_2.0 min chromatography (Xtimate, 2.1*30 mm, 3 um), MS (ESI) m/z 276.1 [M−100]$^+$.

Step 3: (R)-methyl 5-chloro-2-(2,2,3,3,10,10-hexamethyl-8-oxo-4,9-dioxa-7-aza-3-silaundecan-6-yl)nicotinate To a solution of (S)-methyl 4-((tert-butoxycarbonyl)amino)-5-((tert-butyldimethylsilyl)oxy)-3-oxopentanoate (32 g, 85.3 mmol) in THF (320 mL) was added potassium tert-butoxide (10.50 g, 93.8 mmol) at 0° C. After stirring for 45 min, DABCO (10.5 g, 93.8 mmol) and 2-chloro-1,3-bis(dimethylamino)trimethinium hexafluorophosphate (27 g, 89.5 mmol) were added to the mixture at 0° C. The mixture was stirred at rt for 3 h. Ammonium acetate (7.20 g, 93.8 mmol) was added to the above solution, and the resulting mixture was stirred at rt for 18 h. TLC (petroleum ether:ethyl acetate=5:1) showed the starting material was consumed. The mixture was filtered and the filtrate was concentrated under reduced pressure. The residue was diluted with ethyl acetate (200 mL), washed with water (3×100 mL) and brine (100 mL), dried over anhydrous sodium sulfate, filtered and concentrated under reduced pressure. The residue was purified by silica gel chromatography (eluting with petroleum ether:ethyl acetate=10:1, gradient to 8:1) to give (R)-methyl 5-chloro-2-(2,2,3,3,10,10-hexamethyl-8-oxo-4,9-dioxa-7-aza-3-silaundecan-6-yl)nicotinate (11 g, 29%) as a white solid. LCMS $t_R$=0.990 min in 10-80AB_2.0 min chromatography (Xtimate, 2.1*30 mm, 3 um), MS (ESI) m/z 445.0 [M+H]$^+$.

Step 4: (R)-tert-butyl (2-((tert-butyldimethylsilyl)oxy)-1-(5-chloro-3-(hydroxymethyl)pyridin-2-yl)ethyl)carbamate To a solution of (R)-methyl 5-chloro-2-(2,2,3,3,10,10-hexamethyl-8-oxo-4,9-dioxa-7-aza-3-silaundecan-6-yl)nicotinate (4.0 g, 9.0 mmol) in ethanol (40 mL) was added sodium borohydride (0.66 g, 18.0 mmol) and calcium chloride (1.0 g, 9.0 mmol) at 0° C. The mixture was stirred at 0° C. for 2 h. TLC (petroleum ether:ethyl acetate=3:1) showed the starting material was consumed. The mixture was quenched with saturated aqueous NH$_4$Cl solution (20 mL) and concentrated under reduced pressure. The residue was extracted with ethyl acetate (3×20 mL). The combined organic layers were washed with brine (20 mL), dried over anhydrous sodium sulfate, filtered and concentrated under reduced pressure to give (R)-tert-butyl (2-((tert-butyldimethylsilyl)oxy)-1-(5-chloro-3-(hydroxymethyl)pyridin-2-yl)ethyl)carbamate (3.45 g, 92%) as a colorless oil, which was used for the next step directly without further purification.

Step 5: (R)-(5-chloro-2-(2,2,3,3,10,10-hexamethyl-8-oxo-4,9-dioxa-7-aza-3-silaundecan-6-yl)pyridin-3-yl)methyl 4-methylbenzenesulfonate To a solution of (R)-tert-butyl (2-((tert-butyldimethylsilyl)oxy)-1-(5-chloro-3-(hydroxymethyl)pyridin-2-yl)ethyl)carbamate (3.45 g, 8.20 mmol) in CH$_2$Cl$_2$ (40 mL) was added p-toluenesulfonyl chloride (3.15 g, 16.40 mmol) and triethylamine (2.48 g, 24.60 mmol) slowly at 0° C. The mixture was stirred at 0° C. for 1 h. TLC (petroleum ether:ethyl acetate=5:1) showed the starting material was consumed. The mixture was quenched with saturated aqueous NaHCO$_3$ solution (20 mL), extracted with ethyl acetate (3×20 mL) and washed with brine (20 mL). The combined organic layer was dried over anhydrous sodium sulfate, filtered and concentrated under reduced pressure. The residue was purified by silica gel chromatography (eluting with petroleum ether:ethyl acetate=10:1, gradient to 5:1) to give (R)-(5-chloro-2-(2,2,3,3,10,10-hexamethyl-8-oxo-4,9-dioxa-7-aza-3-silaundecan-6-yl)pyridin-3-yl)methyl 4-methylbenzenesulfonate (3.15 g, 66%) as a colorless oil. LCMS $t_R$=1.497 min in 10-80AB_2.0 min chromatography (Xtimate, 2.1*30 mm, 3 um), MS (ESI) m/z 571.0 [M+H]$^+$.

Step 6: (R)-tert-butyl 7-(((tert-butyldimethylsilyl)oxy)methyl)-3-chloro-5H-pyrrolo[3,4-b]pyridine-6(7H)-carboxylate To a solution of (R)-(5-chloro-2-(2,2,3,3,10,10-hexamethyl-8-oxo-4,9- dioxa-7-aza-3-silaundecan-6-yl)pyridin-3- yl)methyl 4-methylbenzenesulfonate (3.15 g, 5.5 mmol) in DMF (30 mL) was added sodium hydride (0.66 g, 16.5 mmol, 60% disperion in mineral oil) at 0° C. The mixture was stirred at 0° C. for 1 h. TLC (petroleum ether:ethyl acetate=5:1) showed the starting material was consumed. The mixture was quenched with saturated aqueous NH₄Cl solution (30 mL) and extracted with ethyl acetate (3×20 mL). The combined organic layers were washed with brine (20 mL), dried over anhydrous sodium sulfate, filtered and concentrated under reduced pressure. The residue was purified by silica gel chromatography (eluting with petroleum ether:ethyl acetate=10:1, gradient to 5:1) to give (R)-tert-butyl 7-(((tert-butyldimethylsilyl)oxy)methyl)-3-chloro-5H-pyrrolo[3,4-b]pyridine-6(7H)-carboxylate (1.20 g, 54%) as a colorless oil. LCMS $t_R$=1.323 min in 10-80AB_2.0 min chromatography (Xtimate ODS 2.1*30 mm, 3 um), MS (ESI) m/z 343.1 [M−55]⁺.

Step 7: (R)-6-(tert-butoxycarbonyl)-7-(((tert-butyldimethylsilyl)oxy)methyl)-6,7-dihydro-5H-pyrrolo[3,4-b]pyridine-3-carboxylic acid Procedure same as that for (S)-6-(tert-butoxycarbonyl)-7-ethyl-6,7-dihydro-5H-pyrrolo[3,4-b]pyridine-3-carboxylic acid with (R)-tert-butyl 7-(((tert-butyldimethylsilyl)oxy)methyl)-3-chloro-5H-pyrrolo[3,4-b]pyridine-6(7H)-carboxylate as the starting material. LCMS $t_R$=3.835 min in 10-80AB_7.0 min chromatography (Xtimate ODS 2.1*30 mm, 3 um), MS (ESI) m/z 353.1 [M−55]⁺. ¹H NMR (CDCl₃, 400 MHz): δ 9.20 (s, 1H), 8.18 (d, J=22.4 Hz, 1H), 4.99 (s, 1H), 4.76 (s, 1H), 4.63-4.64 (m, 1H), 4.42-4.63 (m, 1H), 4.07-4.12 (m, 1H), 1.53 (s, 9H), 0.65 (s, 9H), 0.07 (s, 3H), 0.18 (s, 3H). Basic preparative HPLC method. Mobile phase A: water with 0.05% NH₃H₂O. Mobile phase B: CH₃CN. Flow rate: 80 ml/min. Detection: UV 220 nm/254 nm Column: Phenomenex Gemini C18 250*50 mm*5um. Column temperature: 30° C. Time in min, % A, % B; 0.00, 55, 35; 30.00, 40, 60; 30.20, 0, 100; 35.00, 0, 100.

Preparation A8: (R)-6-(tert-butoxycarbonyl)-7-(methoxymethyl)-6,7-dihydro-5H-pyrrolo[3,4-b]pyridine-3-carboxylic acid

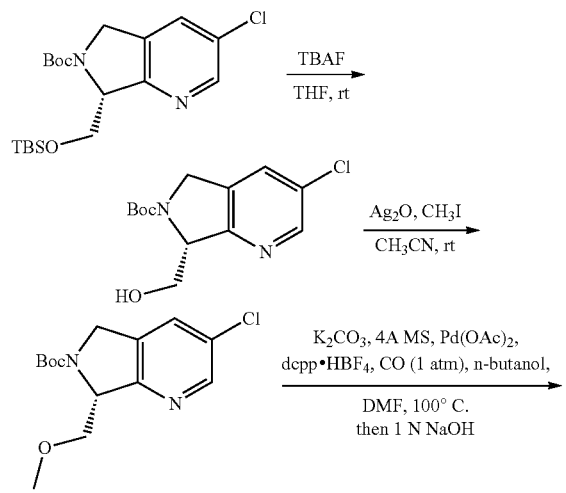

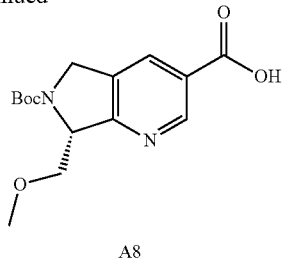

A8

Step 1: (R)-tert-butyl 3-chloro-7-(hydroxymethyl)-5H-pyrrolo[3,4-b]pyridine-6(7H)-carboxylate To a solution of (R)-tert-butyl 7-(((tert-butyldimethylsilyl)oxy)methyl)-3-chloro-5H-pyrrolo[3,4-b]pyridine-6(7H)-carboxylate (1.0 g, 2.5 mmol) in THF (10 mL) was added dropwise tetrabutylammonium fluoride (5 mL, 1.0 M in THF). The mixture was stirred at rt for 4 h. LCMS showed the starting material was consumed. The mixture was concentrated under reduced pressure. The residue was extracted with ethyl acetate (3×10 mL), then the combined organic layer was washed with brine (20 mL), dried over anhydrous sodium sulfate, filtered and concentrated under reduced pressure. The residue was purified by silica gel chromatography (petroleum ether:ethyl acetate=10:1, gradient to 1:1) to give (R)-tert-butyl 3-chloro-7-(hydroxymethyl)-5H-pyrrolo[3,4-b]pyridine-6(7H)-carboxylate (0.55 g, 77%) as a white solid. LCMS $t_R$=0.712 min in 5-95AB_1.5 min chromatography (RP-18e, 25-2 mm) MS (ESI) m/z 229 [M−55]⁺.

Step 2: (R)-tert-butyl 3-chloro-7-(methoxymethyl)-5H-pyrrolo[3,4-b]pyridine-6(7H)-carboxylate To a solution of (R)-tert-butyl 3-chloro-7-(hydroxymethyl)-5H-pyrrolo[3,4-b]pyridine-6(7H)-carboxylate (0.55 g, 1.93 mmol) in CH₃CN (10 mL) was added dropwise silver (I) oxide (2.24 g, 9.68 mmol) and iodomethane (0.60 mL, 9.68 mmol). The mixture was stirred at rt for 18 h. LCMS showed the starting material was consumed. The mixture was filtered and concentrated under reduced pressure. The residue was purified by silica gel chromatography (petroleum ether:ethyl acetate=10:1, gradient to 1:1) to give (R)-tert-butyl 3-chloro-7-(methoxymethyl)-5H-pyrrolo[3,4-b]pyridine-6(7H)-carboxylate (0.40 g, 69%) as a yellow solid. LCMS $t_R$=0.725 min in 5-95AB_1.5 min chromatography (RP-18e, 25-2 mm) MS (ESI) m/z 298.9 [M+H]⁺.

Step 3: (R)-6-(tert-butoxycarbonyl)-7-(methoxymethyl)-6,7-dihydro-5H-pyrrolo[3,4-b]pyridine-3-carboxylic acid Procedure same as that for (S)-6-(tert-butoxycarbonyl)-7-ethyl-6,7-dihydro-5H-pyrrolo[3,4-b]pyridine-3-carboxylic acid with (R)-tert-butyl 3-chloro-7-(methoxymethyl)-5H-pyrrolo[3,4-b]pyridine-6(7H)-carboxylate (400 mg, 1.34 mmol) as the starting material. LCMS $t_R$=0.937 min in 10-80AB_2.0 min chromatography (Xtimate ODS 2.1*30 mm, 3 um), MS (ESI) m/z 309.2 [M+H]⁺. HCl preparative HPLC method. Mobile phase A: water with 0.05% HCl. Mobile phase B: CH₃CN. Flow rate: 30 mL/min Detection: UV 220 nm/254 nm. Column: Synergi Max-RP 150*30 mm*4 u. Column temperature: 30° C. Time in min, % A, % B; 0.00, 70, 30; 11.00, 5, 95; 11.20, 0, 100; 13.00, 0, 100.

Preparation A9: (R)-6-(tert-butoxycarbonyl)-7-(trifluoromethyl)-6,7-dihydro-5H-pyrrolo[3,4-b]pyridine-3-carboxylic acid

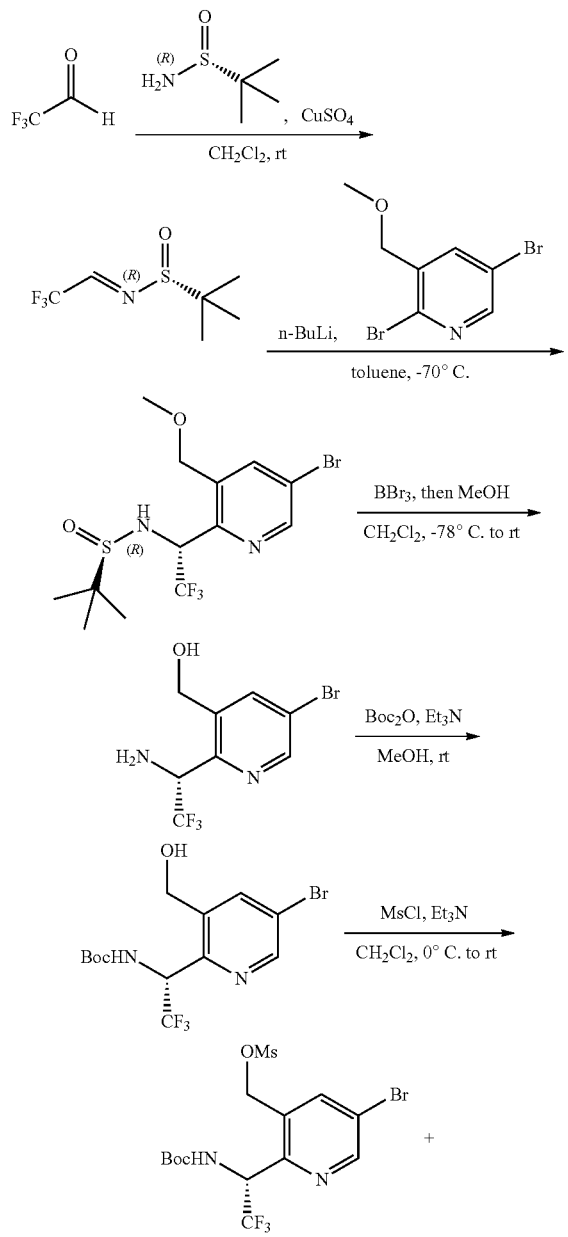

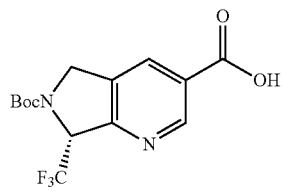

Step 1: (R,E)-2-methyl-N-(2,2,2-trifluoroethylidene)propane-2-sulfinamide

To a solution of 2,2,2-trifluoroacetaldehyde (30.0 g, 0.25 mole) in CH$_2$Cl$_2$ (300 mL) was added (R)-2-methylpropane-2-sulfinamide (31.20 g, 0.25 mole) and MgSO$_4$ (30 g), then the mixture was stirred at 40° C. for 4 h. The mixture was filtered, then 4A MS (120 g) was added to the filtrate. The mixture was stirred at 40° C. for 18 h. The mixture was filtered and the filtrate was concentrated to give (R,E)-2-methyl-N-(2,2,2-trifluoroethylidene)propane-2-sulfinamide (40 g, 76% crude) as a white solid. LC-MS t$_R$=0.851 min in 10-80AB_7.0 min chromatography (Xtimate ODS 2.1*30 mm, 3 um), MS (ESI) m/z 202.0 [M+H]$^+$.

Step 2: (R)—N—((R)-1-(5-bromo-3-(methoxymethyl)pyridin-2-yl)-2,2,2-trifluoroethyl)-2-methylpropane-2-sulfinamide To 30 mL of toluene was added n-BuLi (6.0 mL, 1.50 mmol) at −70° C., followed a solution of 2,5-dibromo-3-(methoxymethyl)pyridine (2.80 g, 1.0 mmol) in toluene (10 mL). After being stirred for 30 min, a solution of (R,E)-2-methyl-N-(2,2,2-trifluoroethylidene)propane-2-sulfinamide (3.35 g, 1.0 mmol, 60% purity) in toluene (10 mL) was added to the mixture. The resulting mixture was stirred at −70° C. for 2 h. Saturated aqueous NH$_4$Cl solution (20 mL) was added to the mixture, followed by extraction with ethyl acetate (3×20 mL). The combined organic layers were washed with brine (20 mL), dried over anhydrous sodium sulfate, filtered and concentrated under reduced pressure. The residue was purified by silica gel chromatography (eluting with petroleum ether:ethyl acetate=5:1, gradient to 3:1) to give (R)—N—((R)-1-(5-bromo-3-(methoxymethyl)pyridin-2-yl)-2,2,2-trifluoroethyl)-2-methylpropane-2-sulfinamide (1.60 g, 39%) as an oil. LC-MS t$_R$=1.105 min in 10-80AB_2.0 min chromatography (Xtimate, 2.1*30 mm, 3 um), MS (ESI) m/z 402.9 [M+H]$^+$.

Step 3: (R)-(2-(1-amino-2,2,2-trifluoroethyl)-5-bromopyridin-3-yl)methanol

To a solution of (R)—N—((R)-1-(5-bromo-3-(methoxymethyl)pyridin-2-yl)-2,2,2-trifluoroethyl)-2-methylpropane-2-sulfinamide (0.75 g, 1.86 mmol) in CH$_2$Cl$_2$ (10 mL) was added boron tribromide (2.33 g, 9.32 mmol) at −78° C. The mixture was stirred at rt for 18 h. Methanol (10 mL) was added to the mixture slowly. The mixture was concentrated under reduced pressure to give (R)-(2-(1-amino-2,2,2- trifluoroethyl)-5-bromopyridin-3-yl)methanol (0.529 g, 100% crude) as a yellow oil which was used in the next step directly. LC-MS $t_R$=1.306 min in 10-80 CD_POS (Xtimate ODS 2.1*30 mm, 3 um), MS (ESI) m/z 284.9 [M+H]$^+$.

Step 4: (R)-tert-butyl (1-(5-bromo-3-(hydroxymethyl)pyridin-2-yl)-2,2,2-trifluoroethyl)carbamate A mixture of (R)-(2-(1-amino-2,2,2-trifluoroethyl)-5-bromopyridin-3-yl)methanol (529 mg, 1.86 mmol), di-tert-butyl dicarbonate (0.814 g, 3.73 mmol) and triethylamine (0.939 g, 9.30 mmol) in MeOH (10 mL) was stirred at rt for 18 h. The mixture was concentrated under reduced pressure. The residue was purified by silica gel chromatography (eluting with petroleum ether:ethyl acetate=10:1, gradient to 5:1) to give (R)-tert-butyl (1-(5-bromo-3-(hydroxymethyl)pyridin-2-yl)-2,2,2-trifluoroethyl)carbamate (510 mg, 71%) as a white solid. LC-MS $t_R$=1.036 min in 10-80AB_2.0 min chromatography (Xtimate ODS 2.1*30 mm, 3 um), MS (ESI) m/z 385.0 [M+H]$^+$.

Step 5: (R)-(5-bromo-2-(1-((tert-butoxycarbonyl)amino)-2,2,2-trifluoroethyl)pyridin-3-yl)methyl methanesulfonate & (R)-tert-butyl (1-(5-bromo-3-(chloromethyl)pyridin-2-yl)-2,2,2-trifluoroethyl)carbamate To a solution of (R)-tert-butyl (1-(5-bromo-3-(hydroxymethyl)pyridin-2-yl)-2,2,2-trifluoroethyl)carbamate (510 mg, 1.32 mmol) and triethylamine (0.91 mL, 6.60 mmol) in CH$_2$Cl$_2$ (10 mL) was added methanesulfonyl chloride (302 mg, 2.64 mmol) at 0° C. The mixture was stirred at rt for 18 h. LCMS showed the starting material was consumed. The reaction mixture was quenched with H$_2$O (10 mL), then extracted with CH$_2$Cl$_2$ (3×10 mL). The combined organic layers were washed with brine (20 mL), dried over anhydrous Na$_2$SO$_4$, filtered and concentrated under reduced pressure. The residue was purified by silica gel chromatography (eluting with petroleum ether:ethyl acetate=10:1, gradient to 5:1) to give (R)-(5-bromo-2-(1-((tert-butoxycarbonyl)amino)-2,2,2-trifluoroethyl)pyridin-3-yl)methyl methanesulfonate (150 mg, 25%) as a white solid and (R)-tert-butyl (1-(5-bromo-3-(chloromethyl)pyridin-2-yl)-2,2,2-trifluoroethyl)carbamate (350 mg, 66%) as a white solid. LC-MS $t_R$=1.265 min in 10-80AB_2.0 min chromatography (Xtimate, 2.1*30 mm, 3 um), MS (ESI) m/z 347.0 [M+H]$^+$.

Step 6: (R)-tert-butyl 3-bromo-7-(trifluoromethyl)-5H-pyrrolo[3,4-b]pyridine-6(7H)-carboxylate To a solution of (R)-tert-butyl (1-(5-bromo-3-(chloromethyl)pyridin-2-yl)-2,2,2-trifluoroethyl)carbamate (350 mg, 0.87 mmol) in DMF (10 mL) was added sodium hydride (104 mg, 2.61 mmol, 60% dispersion in mineral oil) at 0° C. The mixture was stirred at 0° C. for 1 h. The mixture was quenched with water (10 mL) and extracted with ethyl acetate (3×10 mL). The combined organic layer was washed with brine (20 mL), dried over anhydrous Na$_2$SO$_4$, filtered and concentrated under reduced pressure. The residue was purified by silica gel chromatography (eluting with petroleum ether:ethyl acetate=10:1, gradient to 8:1) to give (R)-tert-butyl 3-bromo-7-(trifluoromethyl)-5H-pyrrolo[3,4-b]pyridine-6(7H)-carboxylate (170 mg, 53%) as a white solid. LC-MS $t_R$=1.097 min in 10-80AB_2.0 min chromatography (Xtimate, 2.1*30 mm, 3 um), MS (ESI) m/z 367.0 [M+H]$^+$.

SFC $t_R$=1.491 min (major), 1.778 min in 12.0 min chromatography (Column: AD-3_B3_5_40_25 ML), ee=67.2%.

Step 7: (R)-6-(tert-butoxycarbonyl)-7-(trifluoromethyl)-6,7-dihydro-5H-pyrrolo[3,4-b]pyridine-3-carboxylic acid Procedure same as that for (S)-6-(tert-butoxycarbonyl)-7-ethyl-6,7-dihydro-5H-pyrrolo[3,4-b]pyridine-3-carboxylic acid with (R)-tert-butyl 3-bromo-7-(trifluoromethyl)-5H-pyrrolo[3,4-b]pyridine-6(7H)-carboxylate as the starting material. LC-MS $t_R$=2.466 min in 10-80AB_7.0 min chromatography (Xtimate ODS 2.1*30 mm, 3 um), MS (ESI) m/z 333.1 [M+H]$^+$. HCl preparative HPLC method. Mobile phase A: water with 0.05% HCl. Mobile phase B: CH$_3$CN. Flow rate: 30 mL/min. Detection: UV 220 nm/254 nm Column: Synergi Max-RP 150*30 mm*4 um. Column temperature: 30° C. Time in min, % A, % B; 0.00, 60, 40; 8.00, 30, 70; 8.20, 0, 100; 10.00, 0, 100.

Preparation B1: (R)-2-amino-2-(4-(ethylsulfonyl)phenyl)ethanol

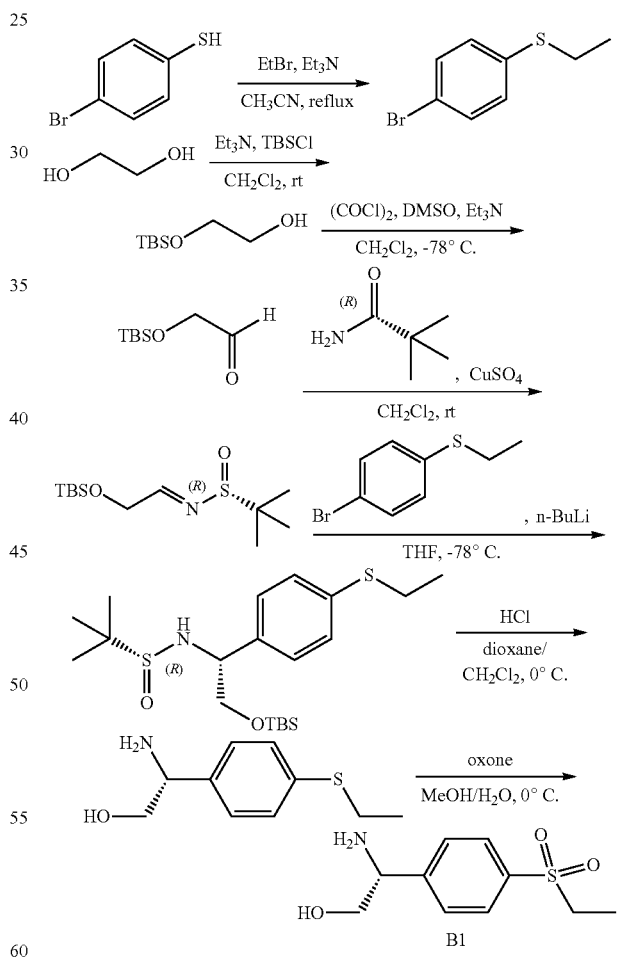

Step 1: (4-bromophenyl)(ethyl)sulfane

A mixture of 4-bromobenzenethiol (50 g, 0.26 mol), bromoethane (58 g, 0.53 mol) and triethylamine (78 g, 0.78 mol) in acetonitrile (1 L) was stirred at reflux for 17 h. The mixture was cooled to rt and filtered. The filtrate was concentrated under vacuum. The residue was purified by silica gel chromatography (eluting with petroleum ether) to give (4-bromophenyl)(ethyl)sulfane (55 g, 96%) as an oil. $^1$H NMR (CDCl$_3$, 400 MHz): δ 7.40-7.42 (dd, J=6.4, 2.0 Hz, 2H), 7.18-7.20 (dd, J=6.4, 2.0 Hz, 2H), 2.91-2.96 (q, J=7.2 Hz, 2H), 1.30-1.33 (t, J=7.2 Hz, 3H).

Step 2: 2-((tert-butyldimethylsilyl)oxy)ethanol

To a solution of ethane-1,2-diol (110 g, 1.77 mol) in anhydrous CH$_2$Cl$_2$ (1.1 L) was added triethylamine (215.2 g, 296 mL, 2.13 mol) at rt. The mixture was cooled to 0° C., then tert-butylchlorodimethylsilane (267.1 g, 1.77 mol) dissolved in CH$_2$Cl$_2$ (300 mL) was added dropwise over 1 h. The mixture stirred at rt overnight. The reaction mixture was quenched with saturated aqueous NH$_4$Cl solution (400 mL) and separated. The aqueous phase was extracted with MTBE (2×400 mL). The combined organic layers were concentrated under vacuum and the residue was redissolved in MTBE (400 mL). The MTBE layer was washed with water (2×500 mL) and brine (500 mL), dried over anhydrous sodium sulfate, filtered and concentrated under vacuum to give 2-((tert-butyldimethylsilyl)oxy)ethanol (280 g, 90%) as a slight oil, which was used for the next step directly without further purification. $^1$H NMR (CDCl$_3$, 400 MHz): δ 3.64-3.66 (m, 2H), 3.57-3.60 (m, 2H), 0.85 (s, 9H), 0.02 (s, 6H).

Step 3: 2-((tert-butyldimethylsilyl)oxy)acetaldehyde

To a solution of CH$_2$Cl$_2$ (1.8 L) cooled to −30° C. was added oxalyl chloride (79.2 g, 52.8 mL, 624 mmol) dropwise. The mixture was cooled to −78° C., then DMSO (62.5 g, 88.5 mL, 1.25 mmol) was added dropwise. After addition, the mixture was stirred at −78° C. for 30 min. A solution of 2-((tert-butyldimethylsilyl)oxy)ethanol (100 g, 567 mmol) dissolved in CH$_2$Cl$_2$ (200 mL) was added slowly at −78° C. The reaction mixture was stirred at −78° C. for 1 h. Triethylamine (287 g, 395 mL, 2.84 mmol) was added dropwise at −78° C. The mixture was stirred at −78° C. for 30 min and then rt overnight. The reaction mixture was washed with water (1 L), 1 N HCl (2×1 L), saturated aqueous NaHCO$_3$ solution (1 L) and brine (1 L). The organic layer was dried over anhydrous sodium sulfate, filtered and concentrated under vacuum to give 2-((tert-butyldimethylsilyl)oxy)acetaldehyde (98.5 g, 99.8%) as a brown oil, which was used for the next step directly without further purification. $^1$H NMR (CDCl$_3$, 400 MHz): δ 9.70 (s, 1H), 4.22 (s, 2H), 0.93 (s, 9H), 0.11 (s, 6H).

Step 4: (R,E)-N-(2-((tert-butyldimethylsilyl)oxy)ethylidene)-2-methylpropane-2-sulfinamide A mixture of 2-((tert-butyldimethylsilyl)oxy)acetaldehyde (93.5 g, 0.54 mol), (R)-2-methylpropane-2-sulfinamide (78.8 g, 0.65 mol) and copper (II) sulfate (215 g, 1.35 mol) in anhydrous CH$_2$Cl$_2$ (1.5 L) was stirred at rt for 16 h. The mixture was quenched with H$_2$O (800 mL) and separated. The aqueous phase was extracted with CH$_2$Cl$_2$ (2×1 L). The combined organic layers were washed with water (1 L) and brine (1 L), dried over anhydrous sodium sulfate, filtered and concentrated under vacuum. The residue was purified by silica gel chromatography (eluting with petroleum ether: ethyl acetate=8:1) to give (R,E)-N-(2-((tert-butyldimethylsilyl)oxy)ethylidene)-2-methylpropane-2-sulfinamide (38.5 g, 26%) as a yellow oil. $^1$H NMR (CDCl$_3$, 400 MHz): δ 7.96-7.97 (t, J=3.2 Hz, 1H), 4.44-4.45 (d, J=2.8 Hz, 2H), 1.11 (s, 9H), 0.00 (s, 6H).

Step 5: (R)—N—((R)-2-((tert-butyldimethylsilyl)oxy)-1-(4-(ethylthio)phenyl)ethyl)-2-methylpropane-2-sulfinamide To a solution of (4-bromophenyl)(ethyl)sulfane (28.9 g, 133.1 mmol) in anhydrous THF (500 mL) was added dropwise n-butyllithium (73 mL, 181.5 mmol, 2.5 M in hexanes) at −78° C. The mixture was stirred at −78° C. for 30 min. A solution of (R,E)-N-(2-((tert-butyldimethylsilyl)oxy)ethylidene)-2-methylpropane-2-sulfinamide (33.5 g, 121 mmol) in anhydrous THF (100 mL) was added to the mixture at −78° C. The mixture was stirred at −78° C. for 2 h, then allowed to warm to rt and stirred for 2 h. The mixture was quenched with saturated aqueous NH$_4$Cl solution (200 mL) and extracted with ethyl acetate (3×300 mL). The combined organic layer was washed with water (200 mL) and brine (200 mL), dried over anhydrous Na$_2$SO$_4$, filtered and concentrated under vacuum. The residue was purified by silica gel chromatography (eluting with petroleum ether: ethyl acetate=15:1) three times to afford (R)—N—((R)-2-((tert-butyldimethylsilyl)oxy)-1-(4-(ethylthio)phenyl)ethyl)-2-methylpropane-2-sulfinamide (22 g, 44%) as a yellow oil. $^1$H NMR (CDCl$_3$, 400 MHz): δ 7.21-7.24 (d, J=7.2 Hz, 2H), 7.18-7.21 (d, J=8.4 Hz, 2H), 4.42-4.45 (d, J=8.8, 2.4 Hz, 1H), 4.21 (brs, 1H), 3.69-3.73 (dd, J=10.4, 4.4 Hz, 1H), 3.51-3.56 (t, J=9.6 Hz, 1H), 2.87-2.92 (q, J=7.6 Hz, 2H), 1.25-1.29 (t, J=7.2 Hz, 3H), 1.18 (s, 9H), 0.88 (s, 9H), 0.02 (s, 6H). LCMS t$_R$=1.010 min in 5-95AB_1.5 min chromatography (MK RP18e 25-2 mm), MS (ESI) m/z 437.9 [M+Na]$^+$. Isomer SFC t$_R$=3.607 and 4.014 min in 12 min chromatography (AD-H_5_5_40_2.3 5 ML), ee=90.85%.

Step 6: (R)-2-amino-2-(4-(ethylthio)phenyl)ethanol

To a solution of (R)—N—((R)-2-((tert-butyldimethylsilyl)oxy)-1-(4-(ethylthio)phenyl)ethyl)-2-methylpropane-2-sulfinamide (22 g, 52.9 mmol) in CH$_2$Cl$_2$ (250 mL) was added HCl (26.5 mL, 4 N in dioxane) at 0° C. The mixture was stirred at rt for 2 h. LCMS showed no starting material remaining. The mixture was concentrated under reduced pressure to afford crude (R)-2-amino-2-(4-(ethylthio)phenyl)ethanol HCl salt (12.3 g, 100%) as a brown solid, which was used for the next step directly without further purification. LCMS t$_R$=1.226 min in 0-30AB_2 min chromatography (Xtimate 3 um, C18, 2.1*30 mm), MS (ESI) m/z 180.9 [M−OH]$^+$.

Step 7: (R)-2-amino-2-(4-(ethylsulfonyl)phenyl)ethanol

To a mixture of (R)-2-amino-2-(4-(ethylthio)phenyl)ethanol (15.2 g, 65.0 mmol) in methanol (200 mL) was added dropwise a solution of oxone reagent (80.0 g, 130.0 mmol) in water (200 mL) at 0° C. The mixture was stirred at rt for 1.5 h; LCMS showed no starting material remaining. The mixture was filtered and methanol was removed under reduced pressure. The aqueous phase was extracted with EtOAc (2×80 mL), then the aqueous layer was basified to pH=8-9 with solid sodium carbonate portionwise at 0° C., then this solution was lyophilized (contained the Na$_2$CO$_3$). The solid was dissolved in CH$_2$Cl$_2$:MeOH (3:1, 600 mL) and stirred for 30 min, filtered, then concentrated under reduced pressure. The residue was purified by silica gel chromatography (eluting with CH$_2$Cl$_2$:MeOH=1:0 to 4:1) to give (R)-2-amino-2-(4-(ethylsulfonyl)phenyl)ethanol (11.5 g, 77%) as a white solid. LC-MS t$_R$=0.738 min in 0-30CD_POS chromatography (Xtimate ODS 2.1*30 mm, 3 um), MS (ESI) m/z 230.1 [M+H]$^+$. Isomer SFC t$_R$=6.99 min in 30 min chromatography (CD-PH_10-80_B_08 ML), ee=97.42%. $^1$H NMR (D$_2$O, 400 MHz): δ 7.82-7.84 (d, J=8.0 Hz, 2H), 7.54-7.56 (d, J=8.4 Hz, 2H), 4.33-4.35 (t, J=6.4 Hz, 1H), 3.72-3.78 (m, 2H), 3.19-3.25 (q, J=7.6 Hz, 2H), 1.03-1.07 (t, J=7.6 Hz, 3H).

Alternate Preparation for B1

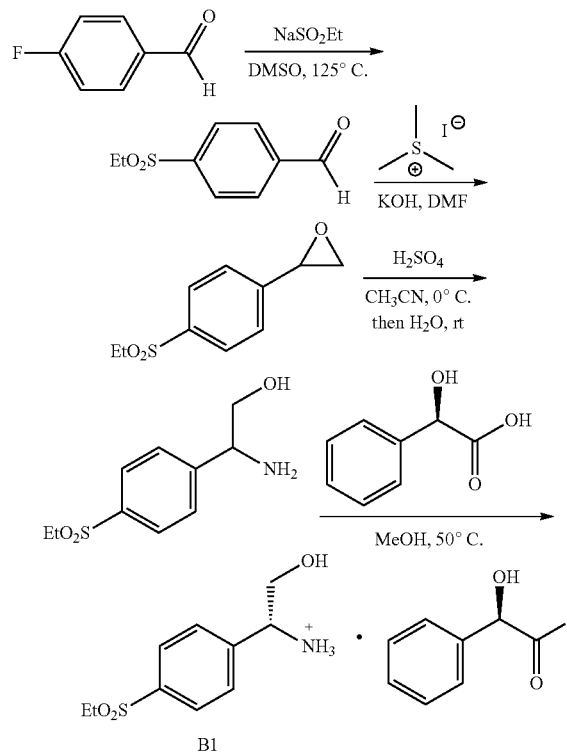

Step 1: 4-(ethylsulfonyl)benzaldehyde

To a solution of 4-fluorobenzaldehyde (24.6 g, 198 mmol) in dimethylsulfoxide (60 mL) was added sodium ethanesulfinate (46 g, 396 mmol). The resulting mixture was stirred at 125° C. for 20 h. After cooling to rt, the reaction mixture was triturated with 350 mL of H$_2$O. The product was filtered, washed with two 10-mL portions of EtOH and dried under vacuum to afford 4-(ethylsulfonyl)benzaldehyde as a light yellow solid (31.2 g, 80% yield). LC-MS t$_R$=1.19 min in 2 min chromatography, MS (ESI) m/z 199.1 [M+H]$^+$. $^1$H NMR (CDCl$_3$) δ 10.14 (s, 1H), 8.09 (s, 4H), 3.16 (q, J=7.2 Hz, 2H), 1.30 (t, J=7.2 Hz, 3H).

Step 2: 2-(4-(ethylsulfonyl)phenyl)oxirane

To a solution of 4-(ethylsulfonyl)benzaldehyde (10 g, 50.5 mmol) in DMF (85 mL) at rt was added trimethylsulfonium iodide (11.9 g, 58.1 mmol) followed by potassium hydroxide powder (5.66 g, 101 mmol). The reaction mixture was stirred at rt for 20 min before quenching with H$_2$O (50 mL). The mixture was carefully neutralized with 1 N HCl solution (55 mL) and extracted with ethyl acetate (3×100 mL). The combined organic phase was washed with brine, dried over anhydrous Na$_2$SO$_4$, and passed through a pad of silica gel (eluting with ethyl acetate). It was concentrated under reduced pressure to afford crude 2-(4-(ethylsulfonyl) phenyl)oxirane as yellow oil, which was used directly for the next step without further purification. LC-MS t$_R$=1.13 min in 2 min chromatography, MS (ESI) m/z 213.2 [M+H]$^+$.

Step 3: 2-amino-2-(4-(ethylsulfonyl)phenyl)ethan-1-ol

To a solution of crude 2-(4-(ethylsulfonyl)phenyl)oxirane (50.5 mmol) in CH$_3$CN (200 mL) at 0° C. was slowly added concentrated sulfuric acid (5.4 mL, 101 mmol). The mixture was allowed to stir at rt for 1.5 h. LCMS showed the starting material was consumed. H$_2$O (15 mL) was added to the reaction mixture. Stirring continued at rt for 8 h, then at 45° C. for 10 h. After cooling to rt, the pH of the reaction mixture was adjusted to 3-4 by addition of 1 N NaOH solution (90 mL). The mixture was extracted with ethyl acetate (100 mL). The organic phase was then extracted with H$_2$O (2×30 mL). The combined aqueous layers were then basified with 1 N NaOH solution (110 mL) to pH=9 and extracted with 1-butanol (5×60 mL). The combined organic layer (consisting of 1-butanol extracts) was dried over anhydrous Na$_2$SO$_4$, filtered and concentrated under reduced pressure. It was dried under high vacuum to afford crude 2-amino-2-(4-(ethylsulfonyl)phenyl)ethan-1-ol as an off-white solid. 4 g, 35% yield over 3 steps. Intermediate 4-(4-(ethylsulfonyl) phenyl)-2-methyl-4,5-dihydrooxazole: LC-MS t$_R$=0.77, 0.81 min in 2 min chromatography, MS (ESI) m/z 254.26 [M+H]$^+$. 2-amino-2-(4-(ethylsulfonyl)phenyl)ethan-1-ol: LC-MS t$_R$=0.61 min in 2 min chromatography, MS (ESI) m/z 230.21 [M+H]$^+$. $^1$H NMR (CD$_3$OD): δ 7.88 (d, J=8.4 Hz, 2H), 7.64 (d, J=8.4 Hz, 2H), 4.16-4.12 (m, 1H), 3.76-3.72 (m, 1H), 3.66-3.61 (m, 1H), 3.17 (q, J=7.2 Hz, 2H), 1.19 (t, J=7.2 Hz, 3H).

Step 4: 2-amino-2-(4-(ethylsulfonyl)phenyl)ethan-1-ol mono-mandelate salt

To a solution of 2-amino-2-(4-(ethylsulfonyl) phenyl)ethan-1-ol (238 mg, 1.0 mmol) in MeOH (3 mL) at 50° C. was added a solution of (R)-Mandelic acid (76 mg, 0.5 mmol) in MeOH (1 mL). The resulting solution was allowed to cool down to ambient temperature slowly. After stirring for 1 day, the resulting crystals were collected by vacuum filtration and dried under high vacuum, providing the mono-mandelate salt as a white crystal, 107 mg (28% yield), 92.5% ee. $^1$H NMR (CD$_3$OD): δ 7.97 (d, J=8.0 Hz, 2H), 7.71 (d, J=8.4 Hz, 2H), 7.46 (d, J=8.0 Hz, 2H), 7.46 (d, J=8.0 Hz, 2H), 7.31-7.27 (m, 2H), 7.25-7.22 (m, 1H), 4.42-4.42 (m, 1H), 3.92-3.89 (m, 1H), 3.81-3.77 (m, 1H), 3.21 (q, J=7.2 Hz, 2H), 1.21 (t, J=7.2 Hz, 3H).

Preparation B2: (1R,2R)-1-amino-1-(4-(ethylsulfonyl)phenyl)propan-2-ol and (1S,2S)-1-amino-1-(4-(ethylsulfonyl)phenyl)propan-2-ol

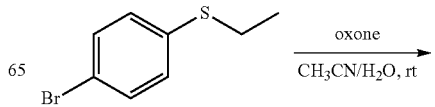

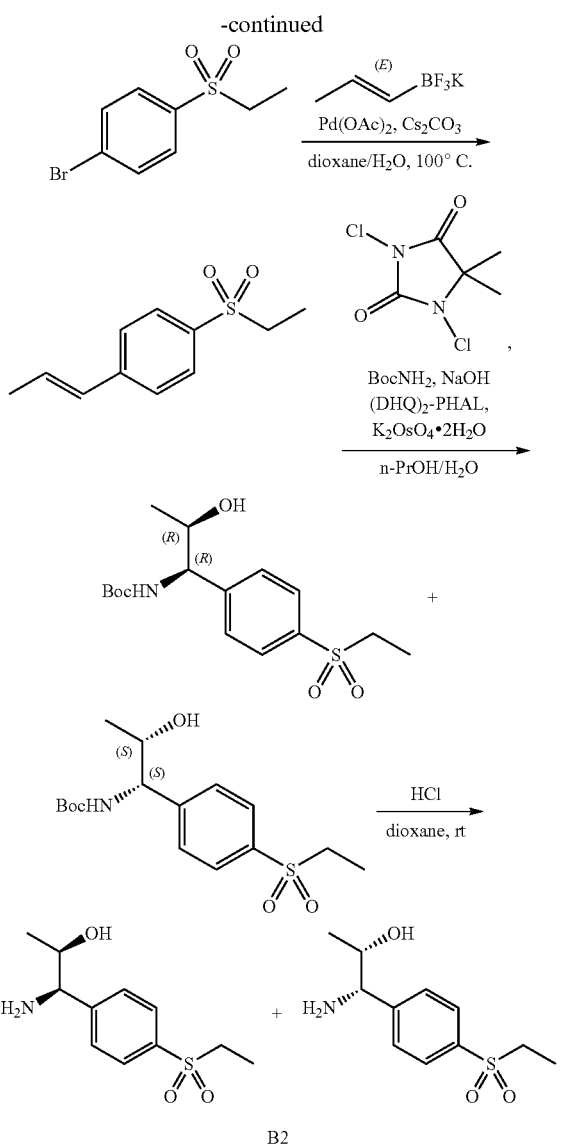

Step 1: 1-bromo-4-(ethylsulfonyl)benzene

To a solution of (4-bromophenyl)(ethyl)sulfane (5 g, 23.15 mmol) in acetonitrile (50 mL) was added water (50 mL) and oxone (28.94 g, 46.30 mmol). The mixture was stirred at rt for 1 h. TLC (petroleum ether:ethyl acetate=10:1) showed that the starting material was completely consumed. The reaction mixture was quenched with saturated aqueous sodium sulfite (150 mL) and extracted with EtOAc (3×50 mL). The combined organic layers were washed with water (100 mL), dried over anhydrous Na$_2$SO$_4$, filtered and concentrated under reduced pressure. The residue was purified by silica gel chromatography eluting with petroleum ether:ethyl acetate 10:1 to 2:1 to afford 1-bromo-4-(ethylsulfonyl)benzene (5.2 g, 90%) as a white solid. $^1$H NMR (CDCl$_3$, 400 MHz): δ 7.73 (dd, J=8.4, 18.0 Hz, 4H), 3.10 (q, J=7.2 Hz, 2H), 1.26 (t, J=7.2 Hz, 3H).

Step 2: (E)-1-(ethylsulfonyl)-4-(prop-1-en-1-yl)benzene

To a solution of 1-bromo-4-(ethylsulfonyl)benzene (572 mg, 2.3 mmol) in dioxane (20 mL) was added potassium (E)-propenyl-1-trifluoroborate (375 mg, 2.53 mmol), cesium carbonate (1.5 g, 4.6 mmol), water (4 mL) and palladium (II) acetate (57 mg, 0.25 mmol). The mixture was stirred at 100° C. for 16 h. The mixture was filtered, then the filtrate was concentrated under reduced pressure. The residue was purified by silica gel chromatography eluting with petroleum ether:ethyl acetate 10:1 to 5:1 to afford (E)-1-(ethylsulfonyl)-4-(prop-1-en-1-yl)benzene (410 mg, 85%) as a white solid. $^1$H NMR (CDCl$_3$, 400 MHz): δ 7.80 (d, J=8.4 Hz, 2H), 7.47 (d, J=8.4 Hz, 2H), 6.50-6.35 (m, 2H), 3.10 (q, J=7.6 Hz, 2H), 1.93 (d, J=4.8 Hz, 3H), 1.26 (t, J=7.6 Hz, 3H).

Step 3: tert-butyl ((1R,2R)-1-(4-(ethylsulfonyl)phenyl)-2-hydroxypropyl)carbamate and tert-butyl ((1S,2S)-1-(4-(ethylsulfonyl)phenyl)-2-hydroxypropyl)carbamate To a solution of tert-butyl carbamate (708 mg, 6.05 mmol) in 1-propanol (15 mL) was added aqueous NaOH solution (14 mL, 0.38 M). The mixture was stirred at rt for 5 min, then 1,3-dichloro-5,5-dimethylimidazolidine-2,4-dione (797 mg, 2.93 mmol) was added. The mixture was stirred at rt for 10 min Solutions of (DHQ)$_2$-PHAL (92 mg, 0.12 mmol) in 1-propanol (1 mL), (E)-1-(ethylsulfonyl)-4-(prop-1-en-1-yl)benzene (410 mg, 1.95 mmol) in 1-propanol (2 mL), and K$_2$OsO$_4$.H$_2$O (29 mg, 0.08 mmol) in aq. NaOH solution (0.2 mL, 0.38 M) were added successively to the reaction mixture at 0° C. The mixture was stirred at rt for 16 h. The mixture was diluted with water (100 mL) and extracted with EtOAc (3×50 mL). The combined organic layers were dried over anhydrous Na$_2$SO$_4$, filtered and concentrated under reduced pressure. The residue was purified by chromatography column on silica gel eluting with petroleum ether:ethyl acetate 10:1 to 1:1 and preparative TLC (petroleum ether:ethyl acetate=1:1) to afford a mixture of tert-butyl ((1R,2R)-1-(4-(ethylsulfonyl)phenyl)-2-hydroxypropyl)carbamate and tert-butyl ((1S,2S)-1-(4-(ethylsulfonyl)phenyl)-2-hydroxypropyl)carbamate (175 mg, 26%) as a white solid. LCMS t$_R$=0.774 min in 5-95AB_1.5 min chromatography (Welch MK RP-18e, 25-2 mm), MS (ESI) m/z 366.1 [M+Na]$^+$. $^1$H NMR (CDCl$_3$ 400 MHz): δ 7.86 (d, J=8.4 Hz, 2H), 7.50 (d, J=8.4 Hz, 2H), 5.60-5.50 (m, 1H), 4.75-4.60 (m, 1H), 4.13-4.02 (m, 1H), 3.10 (q, J=7.6 Hz, 2H), 1.43 (s, 9H), 1.35-1.25 (m, 6H).

Step 4: (1R,2R)-1-amino-1-(4-(ethylsulfonyl)phenyl)propan-2-ol and (1S,2S)-1-amino-1-(4-(ethylsulfonyl)phenyl)propan-2-ol Procedure same as that for (S)—N—((S)-1-(4-(ethylsulfonyl)phenyl)-2-hydroxyethyl)-7-isopropyl-6,7-dihydro-5H-pyrrolo[3,4-b]pyridine-3-carboxamide with a mixture of tert-butyl ((1R,2R)-1-(4-(ethylsulfonyl)phenyl)-2-hydroxypropyl)carbamate and tert-butyl ((1S,2S)-1-(4-(ethylsulfonyl)phenyl)-2-hydroxypropyl)carbamate as the starting materials.

Preparation B3: (1R,2S)-1-amino-1-(4-(ethylsulfonyl)phenyl)propan-2-ol & (1S,2R)-1-amino-1-(4-(ethylsulfonyl)phenyl)propan-2-ol

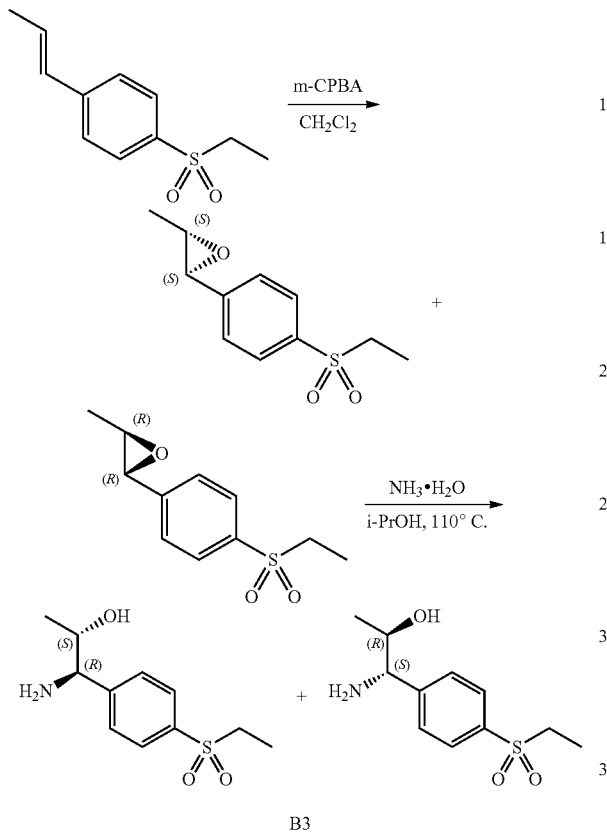

Step 1: (2S,3S)-2-(4-(ethylsulfonyl)phenyl)-3-methyloxirane and (2R,3R)-2-(4-(ethylsulfonyl)phenyl)-3-methyloxirane To a solution of (E)-1-(ethylsulfonyl)-4-(prop-1-en-1-yl)benzene (200 mg, 0.95 mmol) in CH$_2$Cl$_2$ (10 mL) was added m-chloroperbenzoic acid (500 mg, 2.86 mmol). The mixture was stirred at 18° C. for 20 h. TLC (petroleum ether:ethyl acetate=3:1) showed that the starting material was consumed completely. The reaction solution was quenched with saturated aqueous sodium sulfite solution (40 mL) and extracted with CH$_2$Cl$_2$ (3×15 mL). The combined organic layers were dried over anhydrous Na$_2$SO$_4$, filtered and concentrated under reduced pressure. The residue was purified by silica gel chromatography eluting with petroleum ether:ethyl acetate 15:1 to 3:1 to afford a mixture of (2S,3S)-2-(4-(ethylsulfonyl)phenyl)-3-methyloxirane and (2R,3R)-2-(4-(ethylsulfonyl)phenyl)-3-methyloxirane (180 mg, 80%) as a colorless oil. $^1$H NMR (CDCl$_3$, 400 MHz): δ 7.85 (d, J=8.4 Hz, 2H), 7.44 (d, J=8.4 Hz, 2H), 3.64 (d, J=1.6 Hz, 1H), 3.09 (q, J=7.6 Hz, 2H), 3.00 (dd, J=2.0, 5.2 Hz, 1H), 1.47 (d, J=5.2 Hz, 3H), 1.25 (t, J=7.6 Hz, 3H).

Step 2: (1R,2S)-1-amino-1-(4-(ethylsulfonyl)phenyl)propan-2-ol and (1S,2R)-1-amino-1-(4-(ethylsulfonyl)phenyl)propan-2-ol To a mixture of (2S,3S)-2-(4-(ethylsulfonyl)phenyl)-3-methyloxirane and (2R,3R)-2-(4-(ethylsulfonyl)phenyl)-3-methyloxirane (120 mg, 0.53 mmol) in i-PrOH (4 mL) was added ammonium hydroxide (4 mL). The mixture was stirred at 110° C. in a sealed tube for 17 h. LCMS showed that the reaction was complete. The mixture was concentrated under reduced pressure and then lyophilized to remove excess ammonium hydroxide to afford a crude mixture of (1R,2S)-1-amino-1-(4-(ethylsulfonyl)phenyl)propan-2-ol and (1S,2R)-1-amino-1-(4-(ethylsulfonyl)phenyl)propan-2-ol (120 mg, 100%) as a yellow oil, which was used for the next step directly without further purification.

LCMS t$_R$=0.338 min in 0-30AB_2 min chromatography (Welch Xtimate 3 um, C18, 2.1*30 mm), MS (ESI) m/z 243.9 [M+H]$^+$.

Preparation B4: 2-amino-2-(4-(ethylthio)phenyl)propan-1-ol

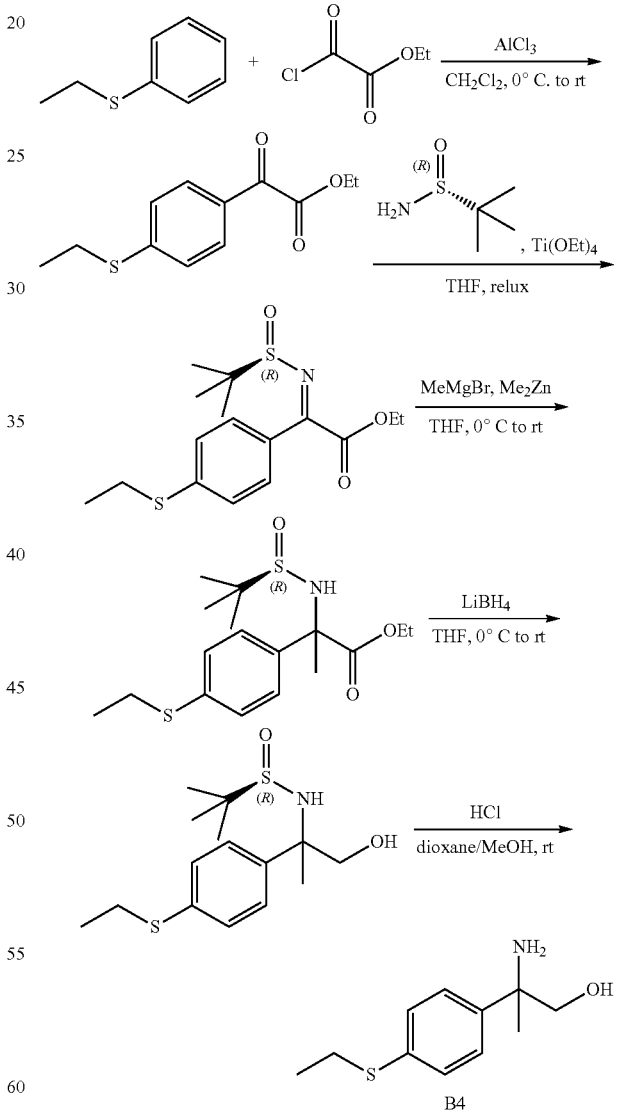

Step 1: ethyl 2-(4-(ethylthio)phenyl)-2-oxoacetate

To a mixture of aluminum chloride (47.6 g, 357 mmol) in dichloromethane (200 mL) at 0° C. was added ethyl 2-chloro-2-oxoacetate (31.9 mL, 286 mmol) slowly. After stirring for 20 min, a solution of ethyl phenyl sulfide (32.80 g, 238 mmol) in dichloromethane (200 mL) was added dropwise at 0° C. After the addition, the mixture was stirred at 0° C. for 30 min before warming to rt and stirring for 2.5 h. LCMS showed that the reaction was complete. The reaction mixture was quenched by ice, diluted with ethyl acetate (800 mL), then washed successively with water (250 mL) and brine (100 mL). It was dried over $Na_2SO_4$, filtered and concentrated by rotary evaporation to afford 52.41 g (93% yield) of crude ethyl 2-(4-(ethylthio)phenyl)-2-oxoacetate as a yellowish oil, which was used without further purification. LCMS $t_R$=1.77 min in 2 min chromatography, MS (ESI) m/z 239 $[M+H]^+$.

Step 2: ethyl (R,E)-2-((tert-butylsulfinyl)imino)-2-(4-(ethylthio)phenyl)acetate To a mixture of ethyl 2-(4-(ethylthio)phenyl)-2-oxoacetate (20 g, 84.3 mmol) in dry THF (100 mL) was added (R)-2-methylpropane-2-sulfinamide (11.18 g, 92.7 mmol) and titanium (IV) ethoxide (28.74 g, 126 mmol). The mixture was heated at reflux overnight. The solution color gradually turned into a light brown. After cooling to rt, the reaction mixture was quenched with brine (25 mL) and stirred for 30 min. It was then filtered through a pad of Celite, rinsing the solid with ethyl acetate (100 mL). The filtrate was washed with water (50 mL) and brine (25 mL), then the organic phase was dried over $Na_2SO_4$, filtered, and concentrated by rotary evaporation to afford 23.09 g (80.6% yield) of crude ethyl (R,E)-2-((tert-butylsulfinyl)imino)-2-(4-(ethylthio)phenyl)acetate as a light brown oil, which was used without further purification. LCMS $t_R$=1.81 min in 2 min chromatography, MS (ESI) m/z 342 $[M+H]^+$.

Step 3: ethyl (R)-2-(((R)-tert-butylsulfinyl)amino)-2-(4-(ethylthio)phenyl)propanoate To a mixture of ethyl (R,E)-2-((tert-butylsulfinyl)imino)-2-(4-(ethylthio)phenyl)acetate (100 mg, 0.293 mmol), in dry THF (4 mL) at 0° C. was added dimethyl zinc (2.0 M in toluene, 161 µL, 0.322 mmol). After stirring for 10 min, methylmagnesium bromide (1.4 M in toluene/THF, 2.46 mL, 3.44 mmol) was added dropwise. The mixture was stirred at 0° C. for 20 min before warming to rt and stirring for 16 h. The reaction mixture was quenched with saturated aqueous ammonium chloride solution (15 mL), then diluted with ethyl acetate (50 mL). The organic layer was washed with 0.5% aqueous HCl (20 mL) and brine (10 mL), dried over $Na_2SO_4$, filtered and concentrated by rotary evaporation. The residue was purified by silica gel chromatography (100% hexanes, gradient to 1:1 hexanes:ethyl acetate) to afford 60 mg (57% yield) of ethyl (R)-2-(((R)-tert-butylsulfinyl)amino)-2-(4-(ethylthio)phenyl)propanoate. LCMS $t_R$=1.61 min in 2 min chromatography, MS (ESI) m/z 358 $[M+H]^+$.

Step 4: (R)—N—((R)-2-(4-(ethylthio)phenyl)-1-hydroxypropan-2-yl)-2-methylpropane-2-sulfinamide To a solution of ethyl (R)-2-(((R)-tert-butylsulfinyl)amino)-2-(4-(ethylthio)phenyl)propanoate (60 mg, 0.168 mmol) in dry THF (3 mL) at 0° C. was added dropwise lithium borohydride (2.0 M in THF, 126 µL, 0.252 mmol). The mixture was stirred at 0° C. for 10 min before warming to rt and stirring for 3 h. The reaction mixture was quenched by saturated aqueous ammonium chloride solution (15 mL) and diluted with ethyl acetate (25 mL). The organic layer was washed with 0.5% HCl (15 mL) and brine (10 mL), dried over $Na_2SO_4$, filtered and concentrated by rotary evaporation to afford 56 mg (~100% yield) of (R)—N—((R)-2-(4-(ethylthio)phenyl)-1-hydroxypropan-2-yl)-2-methylpropane-2-sulfinamide, which was used without further purification. LCMS $t_R$=1.35 min in 2 min chromatography, MS (ESI) m/z 316 $[M+H]^+$.

Step 5: 2-amino-2-(4-(ethylthio)phenyl)propan-1-ol

To a solution of (R)—N—((R)-2-(4-(ethylthio)phenyl)-1-hydroxypropan-2-yl)-2-methylpropane-2-sulfinamide (53 mg, 0.168 mmol) in methanol (3 mL) was added HCl solution (4.0 M in dioxane, 3 mL). The mixture was stirred at rt for 3 h. The mixture was concentrated to afford crude 2-amino-2-(4-(ethylthio)phenyl)propan-1-ol, which was used without further purification. LCMS $t_R$=0.66 min in 2 min chromatography, MS (ESI) m/z 195 $[M-NH_3+H]^+$.

Preparation B5: (R)-2-amino-2-(5-(ethylsulfonyl)pyridin-2-yl)ethanol

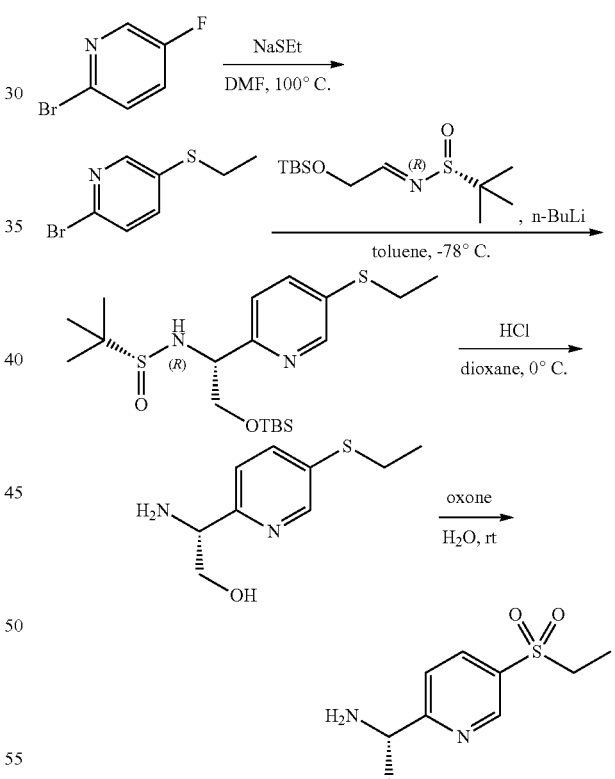

Step 1: 2-bromo-5-(ethylthio)pyridine

To a mixture of 2-bromo-5-fluoropyridine (6.28 g, 35.66 mmol) in anhydrous DMF (60 mL) was added sodium ethanethiolate (3 g, 35.66 mmol). The mixture was stirred at 100° C. for 3 h. TLC (petroleum ether/ethyl acetate 10/1) showed that the starting material was not consumed completely. Additional sodium ethanethiolate (0.9 g, 9.56 mmol) was added to the mixture. The mixture was stirred at 100° C. for 12 h. The mixture was quenched with H₂O (150 mL) and extracted with ethyl acetate (3×150 mL). The combined organic layers were washed with brine (400 mL), dried over anhydrous sodium sulfate, filtered and concentrated under reduced pressure. The residue was purified by silica gel chromatography (eluting with petroleum ether/ethyl acetate 80/1) to afford 2-bromo-5-(ethylthio)pyridine (7.0 g, 90%) as a colorless oil.

LC-MS $t_R$=0.717 min in 5-95AB_1.5 min chromatography (Welch Merck RP-18e 25-2 mm), MS (ESI) m/z 217.6 [M+H]⁺.

Step 2: (R)—N—((R)-2-((tert-butyldimethylsilyl)oxy)-1-(5-(ethylthio)pyridin-2-yl)ethyl)-2-methylpropane-2-sulfinamide To a solution of toluene (60 mL) was added n-BuLi (10.6 mL, 26.48 mmol, 2.5 M in hexanes) dropwise at −78° C.; the internal temperature did not exceed −50° C. A solution of 2-bromo-5-(ethylthio)pyridine (3.85 g, 17.65 mmol) in toluene (10 mL) was then added to the reaction mixture at −78° C.; the internal temperature did not exceed −65° C. The mixture was stirred at −78° C. for 1 h. A solution of (R,E)-N-(2-((tert-butyldimethylsilyl)oxy)ethylidene)-2-methylpropane-2-sulfinamide (4.90 g, 17.65 mmol) in toluene (10 mL) was added to the reaction mixture at −78° C.; the internal temperature did not exceed −60° C. The mixture was stirred at −78° C. for another 2 h. The mixture was quenched with brine (150 mL) at −78° C. and extracted with ethyl acetate (3×150 mL). The combined organic layers were washed with brine (400 mL), dried over anhydrous sodium sulfate, filtered and concentrated under reduced pressure. The residue was purified by silica gel chromatography (eluting with petroleum ether/ethyl acetate 10/1 to 3/1) to afford (R)—N—((R)-2-((tert-butyldimethylsilyl)oxy)-1-(5-(ethylthio)pyridin-2-yl)ethyl)-2-methylpropane-2-sulfinamide (3.0 g, 41%) as a pale yellow oil. LC-MS $t_R$=1.014 min in 5-95AB_1.5 min chromatography (Welch Merck RP-18e 25-2 mm), MS (ESI) m/z 417.2 [M+H]⁺.

Step 3: (R)-2-amino-2-(5-(ethylthio)pyridin-2-yl)ethanol

Procedure same as that for (R)-2-amino-2-(4-(ethylthio)phenyl)ethanol with (R)—N—((R)-2-((tert-butyldimethylsilyl)oxy)-1-(5-(ethylthio)pyridin-2-yl)ethyl)-2-methylpropane-2-sulfinamide as the starting material.

Step 4: (R)-2-amino-2-(5-(ethylsulfonyl)pyridin-2-yl)ethanol

Procedure same as that for (R)-2-amino-2-(4-(ethylsulfonyl)phenyl)ethanol with (R)-2-amino-2-(5-(ethylthio)pyridin-2-yl)ethanol as the starting material. ¹H NMR (CD₃OD, 400 MHz): δ 9.08 (s, 1H), 8.35 (dd, J=2.0, 8.4 Hz, 1H), 7.79 (d, J=8.4 Hz, 1H), 4.70 (t, J=5.6 Hz, 1H), 4.03 (dd, J=4.8, 12.0 Hz, 1H), 3.91 (dd, J=4.8, 11.6 Hz, 1H), 3.29 (q, J=7.2 Hz, 2H), 1.25 (t, J=7.2 Hz, 3H).

Preparation B6: (R)-2-amino-2-(4-(methylsulfonyl)phenyl)ethanol

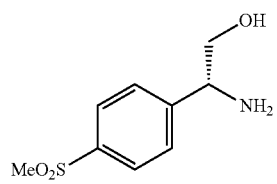

The compound was prepared analogously to (R)-2-amino-2-(4-(methylsulfonyl)phenyl)ethanol (B1).

Preparation B7: (R)-2-amino-2-(5-(methylsulfonyl)pyridin-2-yl)ethanol

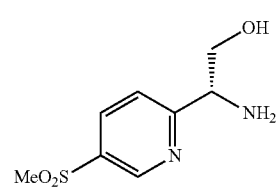

The compound was prepared analogously to (R)-2-amino-2-(5-(ethylsulfonyl)pyridin-2-yl)ethanol (B5).

Preparation C1: trans-4-(trifluoromethyl)cyclohexanecarbaldehyde

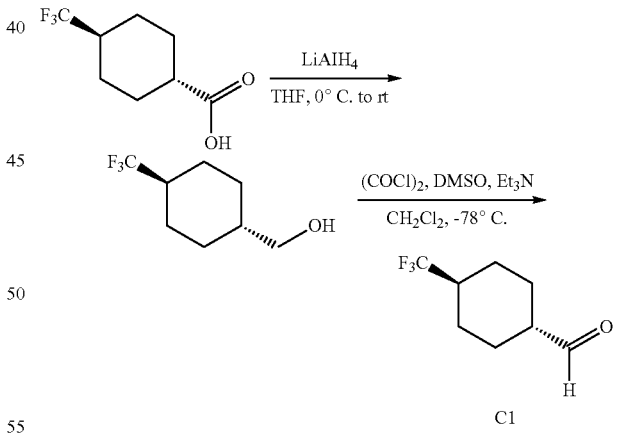

Step 1: (trans-4-(trifluoromethyl)cyclohexyl)methanol

To a mixture of lithium aluminum hydride (11.6 g, 0.306 mol) in anhydrous THF (350 mL) was added a solution of trans-4-(trifluoromethyl)cyclohexanecarboxylic acid (30 g, 0.153 mol) in anhydrous THF (50 mL) at 0° C. dropwise. The mixture was stirred at 0° C. for 2 h. TLC (petroleum ether:ethyl acetate=10:1) showed no starting material remaining. The mixture was quenched with water (12 mL), 15% aqueous NaOH solution (24 mL) and H₂O (12 mL) successively. The mixture was filtered and the filtrate was concentrated under vacuum to give (trans-4-(trifluoromethyl)cyclohexyl)methanol (24 g, 86%) as a liquid. ¹H NMR (CDCl₃, 400 MHz): δ 3.49-3.50 (d, J=6.0 Hz, 2H), 1.91-2.07 (m, 4H), 1.50-1.57 (m, 1H), 1.32-1.36 (m, 2H), 0.98-1.05 (m, 2H).

Step 2: trans-4-(trifluoromethyl)cyclohexanecarbaldehyde

To a mixture of oxalyl chloride (24.96 g, 13.84 mL, 197.7 mmol) in CH₂Cl₂ (250 mL) was added dropwise DMSO (20.72 g, 28 mL, 395.4 mmol) at −65° C. The mixture was stirred at −65° C. for 30 min (trans-4-(trifluoromethyl)cyclohexyl)methanol (12 g, 65.9 mmol) dissolved in CH₂Cl₂ (50 mL) was added dropwise at −65° C. and the mixture was stirred at −65° C. for another 30 min Triethylamine (66.4 g, 91.2 mL, 659 mmol) was added dropwise below −65° C. The mixture was stirred at −65° C. for 30 min, then stirred at rt for 1.5 h. The mixture was quenched with water (200 mL) and separated. The aqueous layer was extracted with CH₂Cl₂ (2×300 mL). The combined organic layers were washed with water (200 mL) and brine (200 mL), dried over anhydrous sodium sulfate, filtered and concentrated under vacuum. The residue was purified by silica gel chromatography (eluting with petroleum ether:ethyl acetate=10:1) to give trans-4-(trifluoromethyl)cyclohexanecarbaldehyde (8.9 g, 75%) as a slight yellow oil. ¹H NMR (CDCl₃, 400 MHz): δ 9.70 (s, 1H), 2.16-2.65 (m, 3H), 2.04-2.12 (m, 3H), 1.00-1.39 (m, 4H).

Preparation C2: 6-(trifluoromethyl)tetrahydro-2H-pyran-3-carbaldehyde

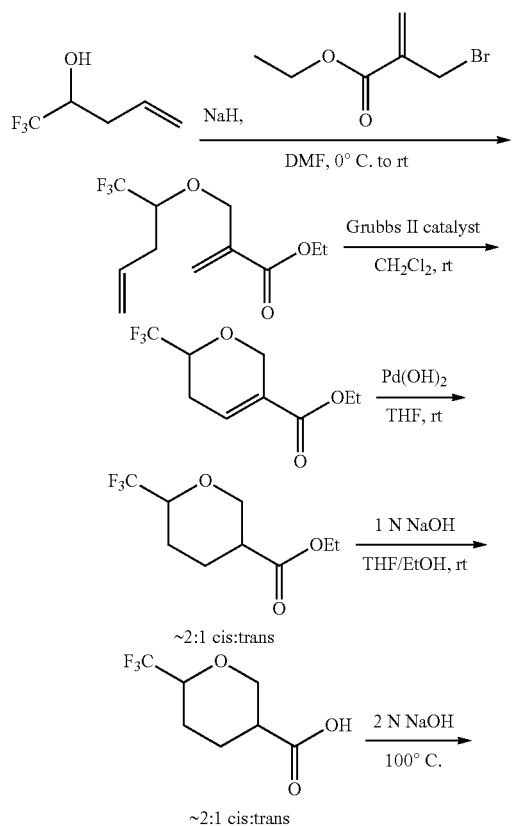

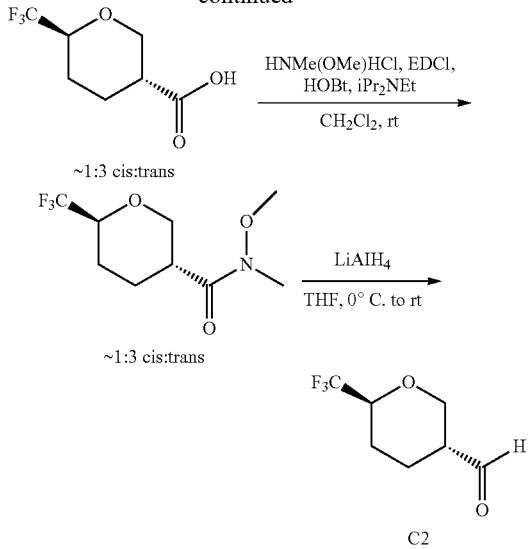

Step 1: ethyl 2-(((1,1,1-trifluoropent-4-en-2-yl)oxy)methyl)acrylate

To a solution of 1,1,1-trifluoropent-4-en-2-ol (6.7 g, 48 mmol) in anhydrous (dried with CaH₂) DMF (85 mL) was added sodium hydride (2.3 g, 57 mmol, 60% in mineral oil) in portions at 0° C. The mixture was stirred at 0° C. for 30 min, then ethyl 2-(bromomethyl)acrylate (9.2 g, 48 mmol) was added dropwise to the resulting mixture via syringe at 0° C. After addition, the mixture was stirred at rt for 2 h. TLC analysis (eluting with petroleum ether:ethyl acetate=10:1) showed that the starting material was consumed. The reaction was quenched with water (50 mL) at 0° C. and the aqueous layer was extracted with ethyl acetate (3×50 mL). The combined organic layers were washed successively with water (3×50 mL) and brine (50 mL), dried over anhydrous sodium sulfate, filtered and concentrated under reduced pressure. The crude residue was purified by silica gel chromatography (eluting with petroleum ether/ethyl acetate: gradient from 100/1 to 50/1) to afford ethyl 2-(((1,1,1-trifluoropent-4-en-2-yl)oxy)methyl)acrylate (6.6 g, 55%) as a pale yellow oil. ¹H NMR (CDCl₃ 400 MHz): δ 6.31 (s, 1H), 5.89 (s, 1H), 5.85-5.74 (m, 1H), 5.23-5.07 (m, 2H), 4.52-4.43 (m, 1H), 4.38-4.15 (m, 3H), 3.82-3.68 (m, 1H), 2.50-2.35 (m, 2H), 1.38-1.20 (m, 3H).

Step 2: ethyl 6-(trifluoromethyl)-5,6-dihydro-2H-pyran-3-carboxylate

To a solution of ethyl 2-(((1,1,1-trifluoropent-4-en-2-yl)oxy)methyl)acrylate (6.6 g, 26.2 mmol) in anhydrous CH₂Cl₂ (2.6 L) was added Grubbs II catalyst (2.2 g, 2.62 mmol) under N₂. The mixture was stirred at rt for 3 h. TLC analysis (eluting with petroleum ether:ethyl acetate=10:1) showed that the reaction was complete. Water (2 L) was added to the mixture to quench the reaction. After partition, the organic layer was washed successively with water (3×2 L) then brine (2 L), dried over anhydrous sodium sulfate, filtered and concentrated under reduced pressure. The residue was purified by silica gel chromatography (eluting with petroleum ether/ethyl acetate: gradient from 100/1 to 80/1) to afford ethyl 6-(trifluoromethyl)-5,6-dihydro-2H-pyran-3-carboxylate (4.83 g, 82%) as a pale yellow oil. ¹H NMR (CDCl₃ 400 MHz): δ 7.01 (d, J=2.8 Hz, 1H), 4.63-4.58 (m, 1H), 4.40-4.33 (m, 1H), 4.20 (q, J=7.2 Hz, 2H), 3.95-3.84 (m, 1H), 2.57-2.46 (m, 1H), 2.41-2.32 (m, 1H), 1.28 (t, J=7.2 Hz, 3H).

Step 3: ethyl 6-(trifluoromethyl)tetrahydro-2H-pyran-3-carboxylate

To a solution of ethyl 6-(trifluoromethyl)-5,6-dihydro-2H-pyran-3-carboxylate (4.83 g, 22 mmol) in anhydrous THF (130 mL) was added dry Pd(OH)₂ on carbon (2.7 g, 10% w/w). The mixture was stirred at rt for 16 h under H₂ (30 psi). TLC analysis (eluting with petroleum ether/ethyl acetate=10/1) showed that most of the starting material was not consumed. The mixture was filtered, then the filtrate was concentrated under reduced pressure and dissolved into anhydrous THF (60 mL). Dry Pd(OH)₂ on carbon (2.7 g, 10% w/w) was added to the mixture. The mixture was stirred at rt for 28 h under H₂ (30 psi). TLC analysis (eluting with petroleum ether/ethyl acetate=10/1) showed that the starting material was consumed. The mixture was filtered and the filtrate was concentrated under reduced pressure to afford crude ethyl 6-(trifluoromethyl)tetrahydro-2H-pyran-3-carboxylate (3.4 g, 70%) as a colorless oil, which was used for the next step directly without further purification. ¹H NMR (CDCl₃ 400 MHz): δ 4.50 (d, J=11.6 Hz, 1H), 4.18 (q, J=7.2 Hz, 2H), 3.80-3.68 (m, 1H), 3.66 (d, J=3.2, 11.6 Hz, 1H), 2.55-2.49 (m, 1H), 2.43-2.35 (m, 1H), 1.95-1.81 (m, 1H), 1.75-1.65 (m, 2H), 1.25 (t, J=7.2 Hz, 3H).

Step 4: 6-(trifluoromethyl)tetrahydro-2H-pyran-3-carboxylic acid

To a solution of crude ethyl 6-(trifluoromethyl)tetrahydro-2H-pyran-3-carboxylate (2.0 g, 8.8 mmol) in THF (24 mL), EtOH (12 mL) was added 1 N aqueous NaOH solution (12 mL). The mixture was stirred at rt for 3 h. TLC analysis (eluting with petroleum ether:ethyl acetate=10:1) showed that the reaction was complete. The mixture was added to water (20 mL) and concentrated under reduced pressure to remove the organic solvent. The residue was washed with MTBE (20 mL) and adjusted to pH=4-5 with 1 N HCl solution. Then, the aqueous layer was extracted with EtOAc (3×20 mL). The combined organic layers were washed with brine (20 mL), dried over anhydrous sodium sulfate, filtered and concentrated under reduced pressure to afford crude 6-(trifluoromethyl)tetrahydro-2H-pyran-3-carboxylic acid (1.72 g, 98%) as a pale yellow oil, which was used for the next step directly without further purification.

The ratio of cis:trans isomers was ~2:1 based on ¹H NMR and ¹⁹F NMR analysis. ¹H NMR (CDCl₃ 400 MHz): δ 8.56 (br s, 1H), 4.47 (d, J=12.0 Hz, 0.68H), 4.25 (d, J=12.0 Hz, 0.32H), 3.76-3.62 (m, 1.68H), 3.47 (t, J=11.2 Hz, 0.32H), 2.71-2.61 (m, 0.32H), 2.58-2.51 (m, 0.68H), 2.38-2.22 (m, 1H), 1.88-1.80 (m, 1H), 1.75-1.60 (m, 2H).

Step 5: 6-(trifluoromethyl)tetrahydro-2H-pyran-3-carboxylic acid

To a solution of crude 6-(trifluoromethyl)tetrahydro-2H-pyran-3-carboxylic acid (1.72 g, 8.69 mmol) was added a 2 N aqueous NaOH solution (76 mL). The mixture was stirred in sealed tube at 100° C. for 84 h. The mixture was diluted with water (20 mL) and washed with MTBE (50 mL). The aqueous layer was adjusted to pH=4-5 with 1 N HCl solution and extracted with EtOAc (3×50 mL). The combined organic layers were washed with brine (50 mL), dried over anhydrous sodium sulfate, filtered and concentrated under reduced pressure to afford crude 6-(trifluoromethyl)tetrahydro-2H-pyran-3-carboxylic acid (1.60 g, 93%) as a pale yellow oil, which was used for the next step directly without further purification.

The ratio of cis:trans was ~1:3 based on ¹H NMR and ¹⁹F NMR analysis. ¹H NMR (CDCl₃ 400 MHz): δ 4.54 (d, J=12.0 Hz, 0.25H), 4.32 (dd, J=2.8, 11.6 Hz, 0.75H), 3.83-3.68 (m, 1.25H), 3.52 (t, J=11.2 Hz, 0.75H), 2.75-2.58 (m, 1H), 2.45-2.30 (m, 1H), 1.95-1.85 (m, 1H), 1.83-1.63 (m, 2H).

Step 6: N-methoxy-N-methyl-6-(trifluoromethyl)tetrahydro-2H-pyran-3-carboxamide To a solution of crude 6-(trifluoromethyl)tetrahydro-2H-pyran-3-carboxylic acid (1.0 g, 5.01 mmol) (~1:3 cis:trans ratio of isomers) in anhydrous CH₂Cl₂ (60 mL) was added N,O-dimethylhydroxylamine hydrochloride (980 mg, 10.10 mmol), EDCI (1.93 g, 10.10 mmol), HOBt (1.36 g, 10.10 mmol), and diisopropylethylamine (1.95 g, 15.15 mmol). The mixture was stirred at rt for 16 h. The mixture was diluted with water (60 mL) and extracted with CH₂Cl₂ (3×60 mL). The combined organic layers were washed with brine (60 mL), dried over anhydrous sodium sulfate, filtered and concentrated under reduced pressure. The residue was purified by silica gel chromatography (eluting with petroleum ether/ethyl acetate: gradient from 30/1 to 15/1) to afford N-methoxy-N-methyl-6-(trifluoromethyl)tetrahydro-2H-pyran-3-carboxamide (1.05 g, 87%) as a pale yellow oil.

The ratio of cis:trans was ~1:3 based on ¹H NMR and ¹⁹F NMR analysis. ¹H NMR (CDCl₃ 400 MHz): δ 4.30-4.24 (m, 0.25H), 4.22-4.15 (m, 0.75H), 3.90-3.68 (m, 4H), 3.62-3.52 (m, 1H), 3.24-3.14 (m, 2H), 3.10-2.98 (m, 1H), 2.14-2.04 (m, 1H), 1.95-1.80 (m, 2H), 1.80-1.65 (m, 2H).

Step 7: 6-(trifluoromethyl)tetrahydro-2H-pyran-3-carbaldehyde

To a solution of N-methoxy-N-methyl-6-(trifluoromethyl)tetrahydro-2H-pyran-3-carboxamide (90 mg, 0.373 mmol) (~1:3 cis:trans ratio of isomers) in anhydrous THF (5 mL) was added lithium aluminum hydride (0.75 mL, 0.746 mmol, 1 M in THF) dropwise at 0° C. under N₂. The mixture was stirred at 0° C. for 1 h. TLC analysis (eluting with petroleum ether/ethyl acetate: 5/1) showed that the reaction was complete. The mixture was quenched with saturated aqueous sodium sulfate solution (1 mL) and filtered. The filtrate was diluted with CH₂Cl₂ (60 mL) and washed with water (60 mL), 10% aqueous HCl solution (0.5 M, 60 mL), saturated aqueous NaHCO₃ solution (60 mL) and water (60 mL). The organic layer was dried over anhydrous sodium sulfate, filtered and concentrated under reduced pressure to afford crude 6-(trifluoromethyl)tetrahydro-2H-pyran-3-carbaldehyde (60 mg, 88%) as a pale yellow oil, which was used for the next step directly without further purification. The ratio of cis:trans was ~1:3 based on ¹H NMR and ¹⁹F NMR analysis.

Preparation C3: trans-5-(trifluoromethyl)tetrahydro-2H-pyran-2-carbaldehyde

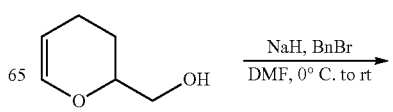

-continued

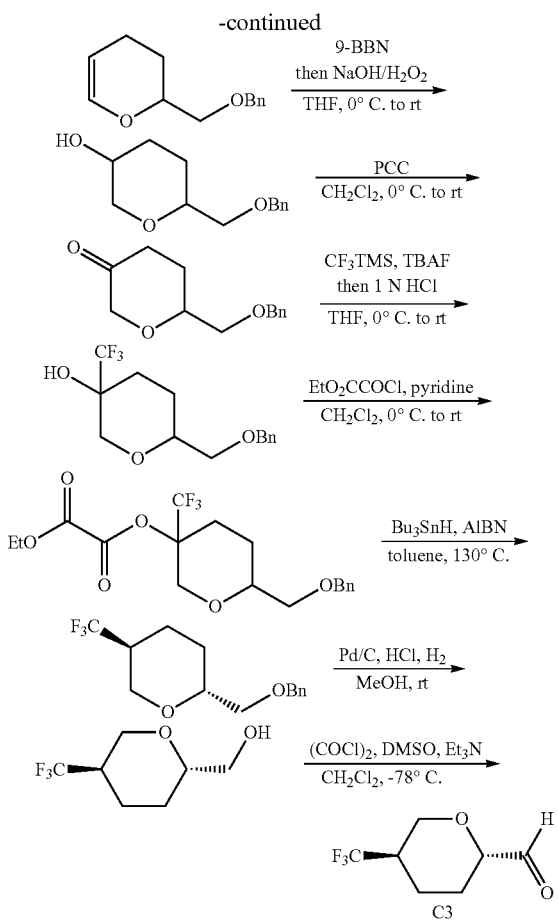

Step 1: 2-((benzyloxy)methyl)-3,4-dihydro-2H-pyran

To a mixture of sodium hydride (15.8 g, 394.5 mmol, 60% in mineral oil) in anhydrous DMF (460 mL) was added dropwise (3,4-dihydro-2H-pyran-2-yl)methanol (30.0 g, 263 mmol) dissolved in anhydrous DMF (20 mL) at 0° C. slowly. The mixture was stirred at 0° C. for 30 min (Bromomethyl) benzene (49.4 g, 34.3 mL, 289 mmol) dissolved in anhydrous DMF (20 mL) was added dropwise and the mixture was stirred at rt for 18 h. TLC (petroleum ether) showed most of the (bromomethyl)benzene was consumed and a new spot was found. The mixture was quenched with H$_2$O (200 mL) at 0° C. slowly, then extracted with ethyl acetate (3×300 mL). The combined organic layers were washed with H$_2$O (3×300 mL) and brine (200 mL), dried over anhydrous sodium sulfate, filtered and concentrated under reduced pressure. The residue was purified by silica gel chromatography on (eluting with petroleum ether) to give 2-((benzyloxy)methyl)-3,4-dihydro-2H-pyran (39.4 g, 73%) as a colorless oil. $^1$H NMR (CDCl$_3$, 400 MHz): δ 7.27-7.35 (m, 5H), 6.39 (d, J=6.0 Hz, 1H), 4.68-4.69 (m, 1H), 4.53-4.63 (m, 2H), 4.00-4.03 (m, 1H), 3.51-3.61 (m, 2H), 2.06-2.09 (m, 1H), 1.98-2.04 (m, 1H), 1.82-1.83 (m, 1H), 1.67-1.70 (m, 1H).

Step 2: 6-((benzyloxy)methyl)tetrahydro-2H-pyran-3-ol

To a mixture of 2-((benzyloxy)methyl)-3,4-dihydro-2H-pyran (31 g, 152 mmol) in anhydrous THF (400 mL) was added dropwise 9-BBN (730 mL, 365 mmol, 0.5 M in THF) at 0° C. for 1 h. The mixture was stirred at rt for 18 h. TLC (petroleum ether:ethyl acetate=5:1) showed the starting material was consumed. 10% aqueous NaOH solution (200 mL) was added to the mixture at 0° C., followed by 30% H$_2$O$_2$ (100 mL). The mixture was stirred at 21-25° C. for 1 h. The reaction mixture was quenched with saturated aqueous Na$_2$SO$_3$ solution (200 mL) at 0° C. and concentrated under reduced pressure to remove THF. The residue was extracted with ethyl acetate (2×200 mL). The combined organic layers were washed with H$_2$O (200 mL) and brine (200 mL), dried over anhydrous sodium sulfate, filtered and concentrated under reduced pressure. The residue was purified by silica gel chromatography (eluting with petroleum ether:ethyl acetate=2:1 to 1:1) to give 6-((benzyloxy) methyl)tetrahydro-2H-pyran-3-ol (30.7 g, 91%) as a colorless oil. LC-MS t$_R$=0.869 min in 10-80AB_2 min chromatography (Xtimate ODS 2.1*30 mm, 3 um), MS (ESI) m/z 240.1 [M+18]$^+$. $^1$H NMR (CDCl$_3$, 400 MHz): δ 7.20-7.27 (m, 5H), 4.45-4.55 (m, 2H), 3.97-4.00 (m, 1H), 3.60-3.65 (m, 1H), 3.34-3.43 (m, 3H), 3.05-3.11 (m, 1H), 2.13-2.14 (m, 1H), 1.69-1.71 (m, 1H), 1.41-1.43 (m, 2H).

Step 3: 6-((benzyloxy)methyl)dihydro-2H-pyran-3(4H)-one

To a mixture of 6-((benzyloxy)methyl)tetrahydro-2H-pyran-3-ol (45.5 g, 205 mmol) in anhydrous CH$_2$Cl$_2$ (500 mL) was added pyridinium chlorochromate (88.4 g, 410 mmol) portionwise at 0° C. The mixture was stirred at rt for 72 h. TLC (petroleum ether: ethyl acetate=3:1) showed the starting material was consumed. The mixture was filtered through Kieselguhr and the filtrate was concentrated under reduced pressure. The residue was purified by silica gel chromatography (eluting with petroleum ether:ethyl acetate=3:1 to 2:1) to give 6-((benzyloxy)methyl)dihydro-2H-pyran-3(4H)-one (31 g, 69%) as an oil. LC-MS t$_R$=0.735 min in 10-80AB_2 min chromatography (Xtimate 2.1*30 mm, 3 um), MS (ESI) m/z 256.1 [M+36]$^+$. $^1$H NMR (CDCl$_3$, 400 MHz): δ 7.19-7.29 (m, 5H), 4.49-4.57 (m, 2H), 4.11-4.15 (m, 1H), 3.92-2.95 (m, 1H), 3.85-3.91 (m, 1H), 3.47-3.54 (m, 2H), 2.53-2.54 (m, 1H), 2.40-2.44 (m, 1H), 1.97-1.99 (m, 1H), 1.83-1.90 (m, 1H).

Step 4: 6-((benzyloxy)methyl)-3-(trifluoromethyl) tetrahydro-2H-pyran-3-ol

To a mixture of 6-((benzyloxy)methyl)dihydro-2H-pyran-3(4H)-one (31.0 g, 141 mmol) and trimethyl(trifluoromethyl)silane (50.1 g, 353 mmol) in anhydrous THF (300 mL) was added dropwise tetrabutylammonium fluoride (3.1 mL, 1 M in THF) at 0° C. The mixture was stirred at rt for 2 h. TLC (petroleum ether:ethyl acetate=5:1) showed the starting material was consumed. HCl solution (340 mL, v:v=1:1) was added to the mixture at 0° C., then stirring continued at rt for 18 h. TLC (petroleum ether:ethyl acetate=5:1) showed the reaction was complete. The mixture was concentrated under reduced pressure to remove THF. The residue was extracted with ethyl acetate (3×200 mL). The combined organic layers were washed with H$_2$O (100 mL,) and brine (100 mL), dried over anhydrous sodium sulfate, filtered and concentrated under reduced pressure. The residue was purified by silica gel chromatography (eluting with petroleum ether:ethyl acetate=5:1) to give 6-((benzyloxy)methyl)-3-(trifluoromethyl)tetrahydro-2H-pyran-3-ol (10.0 g, 25%) as a colorless oil. LC-MS t$_R$=1.041 min in 10-80AB_2 min chromatography (Xtimate ODS 2.1*30 mm, 3 um), MS (ESI) m/z 308.1 [M+18]$^+$. $^1$H NMR (CDCl$_3$, 400 MHz): δ 7.22-7.30 (m, 5H), 4.45-4.55 (m, 2H), 4.09-4.13 (m, 1H), 3.60-3.62 (m, 1H), 3.47-3.49 (m, 1H), 3.32-3.41 (m, 2H), 2.19-2.22 (m, 1H), 2.10 (brs, 1H), 1.62-1.69 (m, 4H). SFC $t_R$=4.512 and 4.857 min in 15 min chromatography (Column: AD-H_3_5_40_2.35 ML), ee=10.12%.

Step 5: 6-((benzyloxy)methyl)-3-(trifluoromethyl) tetrahydro-2H-pyran-3-yl ethyl oxalate To a mixture of 6-((benzyloxy)methyl)-3-(trifluoromethyl)tetrahydro-2H-pyran-3-ol (10.0 g, 34.4 mmol) and pyridine (8.16 g, 8.3 mL, 103.2 mmol) in anhydrous $CH_2Cl_2$ (150 mL) was added dropwise ethyl chlorooxoacetate (9.41 g, 68.8 mmol) at 0° C. The mixture was stirred at rt for 20 h. TLC (petroleum ether:ethyl acetate=5:1) showed most of the starting material was consumed. The mixture was washed with 1 N HCl (50 mL) and brine (50 mL). The organic layer was dried over anhydrous sodium sulfate, filtered and concentrated under reduced pressure. The residue was purified by silica gel chromatography (eluting with petroleum ether:ethyl acetate=8:1) to give 6-((benzyloxy)methyl)-3-(trifluoromethyl)tetrahydro-2H-pyran-3-yl ethyl oxalate (11 g, 82%) as a colorless oil. LC-MS $t_R$=1.225 min in 10-80AB_2 min chromatography (Xtimate ODS 2.1*30 mm, 3 um), MS (ESI) m/z 408.2 [M+18]⁺. ¹H NMR (CDCl₃, 400 MHz): δ 7.29-7.36 (m, 5H), 4.51-4.61 (m, 2H), 4.47-4.48 (m, 1H), 4.35 (q, J=7.2 Hz, 2H), 4.00-4.01 (m, 1H), 3.60-3.62 (m, 1H), 3.53-3.54 (m, 1H), 3.45-3.48 (m, 1H), 2.63-2.68 (m, 1H), 2.34-2.35 (m, 1H), 1.74-1.78 (m, 2H), 139 (t, J=7.2 Hz, 3H).

Step 6: trans-2-((benzyloxy)methyl)-5-(trifluoromethyl)tetrahydro-2H-pyran

To a mixture of 6-((benzyloxy)methyl)-3-(trifluoromethyl)tetrahydro-2H-pyran-3-yl ethyl oxalate (10.0 g, 25.6 mmol) in anhydrous toluene (600 mL) was added dropwise AIBN (1.26 g, 7.68 mmol) and tributyltin hydride (15.05 g, 51.2 mmol) dissolved in anhydrous toluene (200 mL) at 130° C. over 40 min. The mixture was stirred at 130° C. for 7 h. LCMS showed the reaction was complete. The mixture was concentrated under reduced pressure. The residue was dissolved in ethyl acetate (200 mL) and aqueous KF solution (100 mL) and filtered. The filtrate was separated. The aqueous phase was extracted with ethyl acetate (2×200 mL). The combined organic layers were washed with brine (100 mL), dried over anhydrous sodium sulfate, filtered and concentrated under reduced pressure. The residue was purified by silica gel chromatography (eluting with petroleum ether:ethyl acetate=10:1 to 8:1) to give trans-2-((benzyloxy)methyl)-5-(trifluoromethyl)tetrahydro-2H-pyran (less polar peak, 3.3 g, 47%) and cis-2-((benzyloxy)methyl)-5-(trifluoromethyl)tetrahydro-2H-pyran (more polar peak, 1.55 g, 22%) as oil. trans-2-((benzyloxy)methyl)-5-(trifluoromethyl)tetrahydro-2H-pyran: LC-MS $t_R$=3.978 min in 10-80AB_7 min chromatography (Xtimate ODS 2.1*30 mm, 3 um), MS (ESI) m/z 292.0 [M+18]⁺. ¹H NMR (CDCl₃, 400 MHz): δ 7.29-7.35 (m, 5H), 4.57 (q, J=12.0 Hz, 2H), 4.17-4.20 (m, 1H), 3.41-3.54 (m, 4H), 2.37-2.38 (m, 1H), 2.06-2.10 (m, 1H), 1.70-1.74 (m, 1H), 1.30-1.42 (m, 2H). SFC $t_R$=3.237 and 3.528 min in 12 min chromatography (Column: OJ-H_3_5_40_2.5 ML), ee=5.62%. SFC $t_R$=3.158 and 3.375 min in 12 min chromatography (Column: OJ-H_5_5_40_2.5 ML), ee=0.85%. cis-2-((benzyloxy)methyl)-5-(trifluoromethyl)tetrahydro-2H-pyran: LC-MS $t_R$=3.739 min in 10-80AB_7 min chromatography (Xtimate ODS 2.1*30 mm, 3 um), MS (ESI) m/z 292.0 [M+18]⁺. ¹H NMR (CDCl₃ 400 MHz): δ 7.21-7.30 (m, 5H), 4.50 (q, J=12.0 Hz, 2H), 4.14-4.18 (m, 1H), 3.57-3.58 (m, 1H), 3.45-3.49 (m, 1H), 3.33-3.36 (m, 1H), 2.03-2.11 (m, 2H), 1.19-1.77 (m, 3H). SFC $t_R$=3.304 and 4.188 min in 12 min chromatography (Column: OJ-H_3_5_40_2.5 ML), ee=9.85%. SFC $t_R$=3.312 and 4.273 min in 12 min chromatography (Column: OD-H_5_5_40_2.5 ML), ee=18.6%.

Step 7: trans-(5-(trifluoromethyl)tetrahydro-2H-pyran-2-yl)methanol

A mixture of trans-2-((benzyloxy)methyl)-5-(trifluoromethyl)tetrahydro-2H-pyran (1.0 g, 3.6 mmol), dry Pd/C (250 mg, 10% Pd) and HCl (3 mL, 4 N in MeOH) in MeOH (20 mL) was stirred at rt for 18 h under H₂ (15 psi). TLC (petroleum ether:ethyl acetate=10:1) showed the starting material was consumed. The mixture was filtered and the filtrate was concentrated under reduced pressure. The residue was purified by silica gel chromatography (eluting with petroleum ether:ethyl acetate=5:2 to 1:1) to give trans-(5-(trifluoromethyl)tetrahydro-2H-pyran-2-yl)methanol (550 mg, 82%) as a slight yellow oil. ¹H NMR (CDCl₃, 400 MHz): δ 4.10-4.12 (m, 1H), 3.35-3.59 (m, 4H), 2.29-2.30 (m, 1H), 2.01-2.05 (m, 2H), 1.58-1.61 (m, 2H), 1.33-1.36 (m, 1H).

Step 8: trans-5-(trifluoromethyl)tetrahydro-2H-pyran-2-carbaldehyde

To a mixture of oxalyl chloride (1.14 g, 0.77 mL, 8.97 mmol) in anhydrous $CH_2Cl_2$ (15 mL) was added dropwise DMSO (1.4 g, 1.27 mL, 17.94 mmol) at −78° C. The mixture was stirred at −78° C. for 30 min Trans-(5-(trifluoromethyl)tetrahydro-2H-pyran-2-yl)methanol (550 mg, 2.99 mmol) dissolved in $CH_2Cl_2$ (5 mL) was added dropwise at −78° C. and the mixture was stirred at −78° C. for another 2 h. Triethylamine (3.03 g, 4.2 mL, 29.9 mmol) was added dropwise at −78° C. and the mixture was stirred at −78° C. for 30 min, then rt for 1 h. The mixture was added with H₂O (20 mL), extracted with $CH_2Cl_2$ (3×20 mL). The combined organic layers were dried over anhydrous sodium sulfate, filtered and concentrated under reduced pressure. The residue was purified by silica gel chromatography (eluting with petroleum ether:ethyl acetate=3:1) to give trans-5-(trifluoromethyl)tetrahydro-2H-pyran-2-carbaldehyde (450 mg, 70% purity, 83%) as a yellow oil. ¹H NMR (CDCl₃, 400 MHz): δ 9.55 (s, 1H), 4.06-4.19 (m, 2H), 3.35-3.46 (m, 1H), 2.33-2.35 (m, 4H), 2.10-2.14 (m, 1H).

Preparation of Compounds of Formula I

Compounds of Formula (I) were prepared according to the general procedures outlined below.

Example 1

(S)—N—((R)-1-(4-(ethylsulfonyl)phenyl)-2-hydroxyethyl)-7-isopropyl-6-((trans-4-(trifluoromethyl)cyclohexyl)methyl)-6,7-dihydro-5H-pyrrolo[3,4-b]pyridine-3-carboxamide (46)

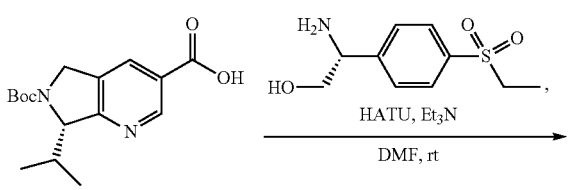

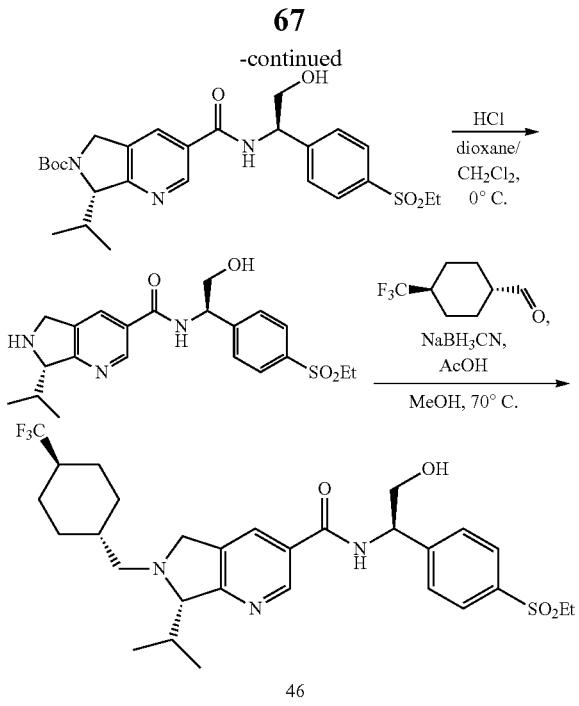

46

Step 1: (S)-tert-butyl 3-(((R)-1-(4-(ethylsulfonyl)phenyl)-2-hydroxyethyl)carbamoyl)-7-isopropyl-5H-pyrrolo[3,4-b]pyridine-6(7H)-carboxylate A mixture of (S)-6-(tert-butoxycarbonyl)-7-isopropyl-6,7-dihydro-5H-pyrrolo[3,4-b]pyridine-3-carboxylic acid (11 g, 36 mmol), (R)-2-amino-2-(4-(ethylsulfonyl)phenyl)ethanol (11.5 g, 43.2 mmol), HATU (16.4 g, 43.2 mmol) and triethylamine (21.9 g, 30 mL, 216 mmol) in DMF (350 mL) was stirred at rt for 2 h. The reaction mixture was diluted with $H_2O$ (140 mL) and extracted with ethyl acetate (3×140 mL). The combined organic layer was washed with water (3×150 mL) and brine (150 mL), dried over anhydrous $Na_2SO_4$, filtered and concentrated under vacuum. The residue was purified by silica gel chromatography (eluting with petroleum ether:ethyl acetate=1:3) to afford (S)-tert-butyl 3-(((R)-1-(4-(ethylsulfonyl)phenyl)-2-hydroxyethyl)carbamoyl)-7-isopropyl-5H-pyrrolo[3,4-b]pyridine-6(7H)-carboxylate (6.1 g, 33%) as a light green solid. LC-MS $t_R$=0.845 min in 5-95AB_1.5 min chromatography (MK RP18e 25-2 mm), MS (ESI) m/z 518.3 [M+H]$^+$. $^1$H NMR (CDCl$_3$, 400 MHz): δ 8.87 (s, 1H), 7.95 (s, 1H), 7.81-7.83 (d, J=8.4 Hz, 2H), 7.53-7.55 (d, J=8.4 Hz, 2H), 7.16 (s, 1H), 5.26-5.28 (m, 1H), 4.88-4.96 (m, 1H), 4.71-4.80 (m, 1H), 4.45-4.47 (m, 1H), 4.03-4.06 (m, 1H), 3.94-3.98 (m, 1H), 3.01-3.06 (q, J=7.6 Hz, 2H), 2.49 (brs, 1H), 2.35 (brs, 1H), 1.46 (s, 9H), 1.19-1.24 (t, J=7.6 Hz, 3H), 0.92-1.02 (m, 3H), 0.67-0.72 (m, 3H). Isomer SFC $t_R$=8.073 and 9.821 min in 15 min chromatography (AD-H_5_5_40_2.35 ML), ee=96.91%.

Step 2: (S)—N—((R)-1-(4-(ethylsulfonyl)phenyl)-2-hydroxyethyl)-7-isopropyl-6,7-dihydro-5H-pyrrolo[3,4-b]pyridine-3-carboxamide To a solution of (S)-tert-butyl 3-(((R)-1-(4-(ethylsulfonyl)phenyl)-2-hydroxyethyl)carbamoyl)-7-isopropyl-5H-pyrrolo[3,4-b]pyridine-6(7H)-carboxylate (6.6 g, 12.8 mmol) in CH$_2$Cl$_2$ (200 mL) was added HCl (60 mL, 4 N in dioxane) at 0° C. The mixture was stirred at rt for 4 h. LCMS showed no starting material remaining. The mixture was concentrated under vacuum. The residue was adjusted to pH=9-10 with 10% NaOH solution, then extracted with ethyl acetate (4×200 mL). The combined organic layers were dried over anhydrous Na$_2$SO$_4$, filtered and concentrated under reduced pressure to afford (S)—N—((R)-1-(4-(ethylsulfonyl)phenyl)-2-hydroxyethyl)-7-isopropyl-6,7-dihydro-5H-pyrrolo[3,4-b]pyridine-3-carboxamide (5.3 g, 99.6%) as a light yellow solid, which was used for the next step directly without further purification. LC-MS $t_R$=0.341 min in 5-95AB_1.5 min chromatography (MK RP18e 25-2 mm), MS (ESI) m/z 418.1 [M+H]$^+$. $^1$H NMR (CDCl$_3$, 400 MHz): δ 8.88 (s, 1H), 7.94 (s, 1H), 7.84-7.86 (d, J=8.4 Hz, 2H), 7.57-7.59 (d, J=8.4 Hz, 2H), 7.28 (s, 1H), 5.29-5.33 (m, 1H), 4.31 (s, 1H), 4.23 (s, 2H), 4.08-4.14 (m, 2H), 4.00-4.07 (m, 1H), 3.06-3.11 (q, J=7.2 Hz, 2H), 2.28-2.31 (m, 1H), 1.24-1.29 (t, J=7.6 Hz, 3H), 1.06-1.08 (d, J=7.2 Hz, 3H), 0.75-0.77 (d, J=6.4 Hz, 3H). Isomer SFC $t_R$=6.964, 7.904 and 9.124 min in 12 min chromatography (AD-3_B2_5_40_25 ML), ee=96.88%.

Step 3: (S)—N—((R)-1-(4-(ethylsulfonyl)phenyl)-2-hydroxyethyl)-7-isopropyl-6-((trans-4-(trifluoromethyl)cyclohexyl)methyl)-6,7-dihydro-5H-pyrrolo[3,4-b]pyridine-3-carboxamide To a mixture of (S)—N—((R)-1-(4-(ethylsulfonyl)phenyl)-2-hydroxyethyl)-7-isopropyl-6,7-dihydro-5H-pyrrolo[3,4-b]pyridine-3-carboxamide (5.3 g, 12.7 mmol) and trans-4-(trifluoromethyl)cyclohexanecarbaldehyde (4.58 g, 25.4 mmol) in anhydrous MeOH (100 mL) was added acetic acid dropwise until the pH was between 6 and 7. Sodium cyanoborohydride (3.19 g, 50.8 mmol) was added portionwise at rt. The mixture was heated to 70° C. and stirred for 1 h. The mixture was cooled to rt and quenched with saturated aqueous sodium bicarbonate (150 mL), then extracted with ethyl acetate (3×200 mL). The combined organic layers were dried over anhydrous Na$_2$SO$_4$, filtered and concentrated under reduced pressure. The residue was purified by silica gel chromatography (eluting with ethyl acetate) to give the product (6.63 g, 90%) as a light green solid, which was purified by SFC separation and acid (HCl) preparative HPLC twice to give (S)—N—((R)-1-(4-(ethylsulfonyl)phenyl)-2-hydroxyethyl)-7-isopropyl-6-((trans-4-(trifluoromethyl)cyclohexyl)methyl)-6,7-dihydro-5H-pyrrolo[3,4-b]pyridine-3-carboxamide (46) (3551.7 mg, 53%) as a light yellow solid. LC-MS $t_R$=0.634 min in 5-95AB_1.5 min chromatography (MK RP-18e 25-2 mm), MS (ESI) adz 582.1 [M+H]$^+$. $^1$H NMR (CD$_3$OD, 400 MHz): δ 9.12-9.13 (d, J=2.0 Hz, 1H), 9.31-9.32 (d, J=1.6 Hz, 1H), 7.91-7.93 (dd, J=6.8, 1.6 Hz, 2H), 7.71-7.73 (d, J=8.0 Hz, 2H), 5.30-5.33 (t, J=6.4 Hz, 1H), 5.16-5.19 (d, J=15.2 Hz, 1H), 4.87-4.89 (m, 1H), 4.70-4.74 (d, J=15.2 Hz, 1H), 3.93-3.95 (d, J=6.4 Hz, 2H), 3.30-3.35 (m, 2H), 3.19-3.25 (q, J=7.6 Hz, 2H), 2.54-2.56 (m, 1H), 2.25-2.27 (m, 1H), 2.03-2.08 (m, 5H), 1.45-1.48 (m, 2H), 1.33-1.35 (m, 4H), 1.23-1.27 (m, 4H), 1.11-1.13 (t, J=6.8 Hz, 3H). $^{19}$F NMR (CD$_3$OD, 400 MHz): δ −75.39. Isomer SFC $t_R$=7.559 min in 12 min chromatography (Column: AD-3_B2_5_40_25 ML) ee=100%. HCl preparative HPLC method; Mobile phase A: water with 0.05% HCl; Mobile phase B: CH$_3$CN. Flow rate: 90 mL/min Detection: UV 220 nm/254 nm Column: Phenomenex Synergi C18 250*50 mm*10 um. Column tem-

Example 2

(S)-7-ethyl-N—((R)-1-(4-(ethylsulfonyl)phenyl)-2-hydroxyethyl)-6-((trans-4-(trifluoromethyl)cyclohexyl)methyl)-6,7-dihydro-5H-pyrrolo[3,4-b]pyridine-3-carboxamide (41)

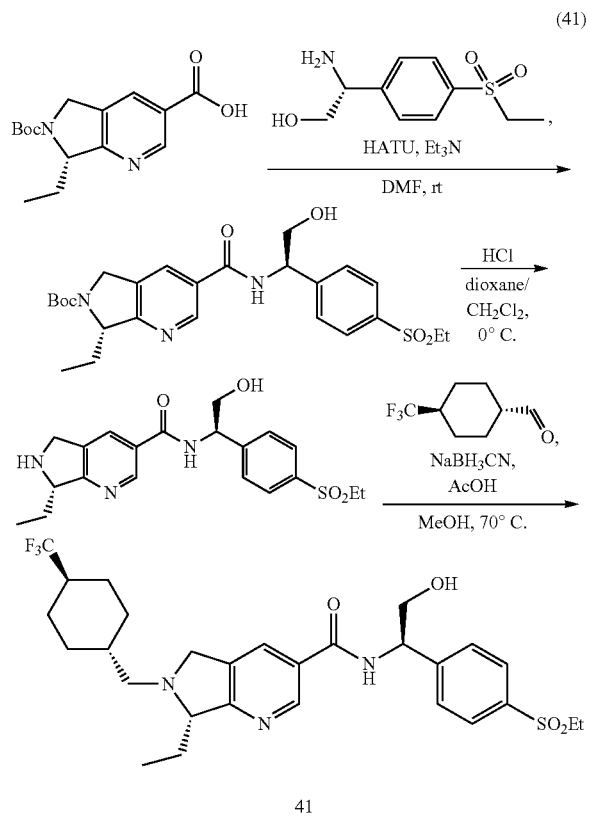

41

Step 1: (S)-tert-butyl 7-ethyl-3-(((R)-1-(4-(ethylsulfonyl)phenyl)-2-hydroxyethyl)carbamoyl)-5H-pyrrolo[3,4-b]pyridine-6(7H)-carboxylate A mixture of (S)-6-(tert-butoxycarbonyl)-7-ethyl-6,7-dihydro-5H-pyrrolo[3,4-b]pyridine-3-carboxylic acid (8 g, 27.4 mmol), HATU (12.5 g, 32.9 mmol) and triethylamine (8.32 g, 11.5 mL, 82.2 mmol) in DMF (120 mL) was stirred at rt for 0.5 h. (R)-2-amino-2-(4-(ethylsulfonyl)phenyl)ethanol (6.9 g, 30.1 mmol) dissolved in DMF (30 mL) was added dropwise to the mixture at 0° C. The mixture was stirred at rt for 2 h. LCMS showed no starting material remaining. The reaction mixture was diluted with water (100 mL) and extracted with ethyl acetate (3×200 mL). The combined organic layers were washed with water (3×100 mL) and brine (100 mL), dried over anhydrous Na₂SO₄, filtered and concentrated under reduced pressure. The residue was purified by silica gel column chromatography (eluting with petroleum ether:ethyl acetate=1:6 to 1:8) to give (S)-tert-butyl 7-ethyl-3-(((R)-1-(4-(ethylsulfonyl)phenyl)-2-hydroxyethyl)carbamoyl)-5H-pyrrolo[3,4-b]pyridine-6(7H)-carboxylate (9.0 g, 65%) as a yellow solid. ¹H NMR (CDCl₃, 400 MHz): δ 8.96 (s, 1H), 8.01 (s, 1H), 7.88-7.90 (d, J=8.0 Hz, 2H), 7.60-7.62 (d, J=8.4 Hz, 2H), 7.29-7.30 (m, 1H), 5.32-5.35 (m, 1H), 5.04-5.13 (m, 1H), 4.76-4.82 (m, 1H), 4.55-4.59 (m, 1H), 4.00-4.13 (m, 2H), 3.08-3.13 (q, J=7.6 Hz, 2H), 2.19-2.22 (m, 2H), 1.53 (s, 9H), 1.28-1.30 (q, J=7.6 Hz, 3H), 0.65-0.68 (q, J=7.2 Hz, 3H). LC-MS $t_R$=0.702 min in 5-95AB_1.5 min chromatography (MERCK RP-18e 25-2 mm), MS (ESI) m/z 504.0 [M+H]⁺.

Step 2: (S)-7-ethyl-N—((R)-1-(4-(ethylsulfonyl)phenyl)-2-hydroxyethyl)-6,7-dihydro-5H-pyrrolo[3,4-b]pyridine-3-carboxamide To a solution of (S)-tert-butyl 7-ethyl-3-(((R)-1-(4-(ethylsulfonyl)phenyl)-2-hydroxyethyl)carbamoyl)-5H-pyrrolo[3,4-b]pyridine-6(7H)-carboxylate (9.0 g, 17.9 mmol) in CH₂Cl₂ (100 mL) was added dropwise HCl (30 mL, 4 N in dioxane) at 0° C. The mixture was stirred at rt for 2 h. TLC (petroleum ether:ethyl acetate=1:3) showed no starting material remaining. The mixture was concentrated under reduced pressure. The residue was basified to pH=9-10 with 10% aqueous NaOH solution, then extracted with ethyl acetate (5×200 mL). The combined organic layers were dried over anhydrous sodium sulfate, filtered and concentrated under reduced pressure to afford (S)-7-ethyl-N—((R)-1-(4-(ethylsulfonyl)phenyl)-2-hydroxyethyl)-6,7-dihydro-5H-pyrrolo[3,4-b]pyridine-3-carboxamide (7.2 g, 100%) as a yellow-red solid, which was used for the next step directly without further purification.

Step 3: (S)-7-ethyl-N—((R)-1-(4-(ethylsulfonyl)phenyl)-2-hydroxyethyl)-6-((trans-4-(trifluoromethyl)cyclohexyl)methyl)-6,7-dihydro-5H-pyrrolo[3,4-b]pyridine-3-carboxamide To a mixture of (S)-7-ethyl-N—((R)-1-(4-(ethylsulfonyl)phenyl)-2-hydroxyethyl)-6,7-dihydro-5H-pyrrolo[3,4-b]pyridine-3-carboxamide (7.2 g, 17.8 mmol) and trans-4-(trifluoromethyl)cyclohexanecarbaldehyde (4.81 g, 26.7 mmol) in anhydrous MeOH (100 mL) was added acetic acid dropwise until the pH was between 6 and 7. Sodium cyanoborohydride (4.47 g, 71.2 mmol) was added portionwise at rt. The mixture was heated to 70° C. and stirred for 1 h. The mixture was cooled to rt and quenched with saturated aqueous sodium bicarbonate (150 mL), then extracted with ethyl acetate (2×150 mL). The combined organic layers were dried over anhydrous Na₂SO₄, filtered and concentrated under reduced pressure. The residue was purified by silica gel chromatography (eluting with ethyl acetate), then purified further by SFC separation (AD-H) and acidic (HCl) preparative HPLC to give (S)-7-ethyl-N—((R)-1-(4-(ethylsulfonyl)phenyl)-2-hydroxyethyl)-6-((trans-4-(trifluoromethyl)cyclohexyl)methyl)-6,7-dihydro-5H-pyrrolo[3,4-b]pyridine-3-carboxamide (41) (total 4.5 g, HCl salt, 46%) as a light yellow solid. LC-MS $t_R$=0.662 min in 5-95AB_1.5 min chromatography (RP-18e 25-2 mm), MS (ESI) m/z 568.0 [M+H]⁺. ¹H NMR (CD₃OD, 400 MHz): δ 9.07 (s, 1H), 8.27 (s, 1H), 7.88-7.90 (d, J=8.0 Hz, 2H), 7.67-7.69 (d, J=8.0 Hz, 2H), 5.26-5.29 (t, J=6.0 Hz, 1H), 5.06-5.10 (m, 2H), 4.70-4.80 (m, 1H), 3.90-3.91 (d, J=6.4 Hz, 2H), 3.30-3.43 (m, 2H), 3.16-3.21 (q, J=7.2 Hz, 2H), 1.97-2.22 (m, 8H), 1.18-1.46 (m, 10H). ¹⁹F NMR (CD₃OD, 400 MHz): δ −75.39. HCl preparative HPLC method Mobile phase A: water with 0.05% HCl; Mobile phase B: CH₃CN. Flow rate: 80 mL/min Detection: UV 220 nm/254 nm Column: Phenomenex Gemini C18 250*50 mm*Sum. Column temperature: 30° C. Time in min: % A:% B; 0.00:70:30; 8.00:45:55; 8.20:0:100; 10.00:0:100.

Example 3

Crystalline mesylate of (S)-7-ethyl-N—((R)-1-(4-(ethylsulfonyl)phenyl)-2-hydroxyethyl)-6-((trans-4-(trifluoromethyl)cyclohexyl)methyl)-6,7-dihydro-5H-pyrrolo[3,4-b]pyridine-3-carboxamide, compound (41) as crystalline mono mesylate (S)-7-ethyl-N—((R)-1-(4-(ethylsulfonyl)phenyl)-2-hydroxyethyl)-6-((trans-4-(trifluoromethyl)cyclohexyl)methyl)-6,7-dihydro-5H-pyrrolo[3,4-b]pyridine-3-carboxamide HCl salt (993.2 mg, 1.64 mmol) was dissolved in CH$_2$Cl$_2$ (60 mL), and washed with 1 N NaOH (40 mL). The aqueous layer was then back-extracted with CH$_2$Cl$_2$ (4×5 mL). The combined CH$_2$Cl$_2$ layers were dried over Na$_2$SO$_4$, filtered, and concentrated under reduced pressure. The free amine (915.1 mg, 1.61 mmol) was redissolved in EtOH (10 mL) and cooled to 0° C. Methanesulfonic acid (Aldrich, 99.5%, 171.3 mg, 1.1 equiv) was added with stirring to obtain a light yellow solution. Several crystal seeds were added to the solution, which was then stirred at rt overnight (white solid came out within 5 min) Crystals were collected by filtration, yielding 985.3 mg (92%) of white solid after pumping under high vacuum for 4 h to afford (S)-7-ethyl-N—((R)-1-(4-(ethylsulfonyl)phenyl)-2-hydroxyethyl)-6-((trans-4-(trifluoromethyl)cyclohexyl)methyl)-6,7-dihydro-5H-pyrrolo[3,4-b]pyridine-3-carboxamide mono mesylate. LC-MS (2 min method): t$_R$=0.93 min $^1$H NMR (CD$_3$OD, 400 MHz): δ 9.06 (d, J=7.2 Hz, 1H), 9.01 (s, 1H), 8.19 (s, 1H), 7.83 (d, J=8.4 Hz, 2H), 7.62 (d, J=8.4 Hz, 2H), 5.22 (dd, J=7.2, 6.0 Hz, 1H), 5.99 (d, J=14.8 Hz, 1H), 4.94 (m, 1H), 4.61 (d, J=14.8 Hz, 1H), 3.84 (d, J=6.0 Hz, 1H), 3.41 (m, 2H), 3.12 (q, J=7.2 Hz, 2H), 2.61 (s, 3H), 2.20-1.80 (m, 8H), 1.44-1.32 (m, 2H), 1.26 (t, J=7.2 Hz, 3H), 1.20 (m, 2H), 1.14 (t, J=7.2 Hz, 3H). $^{19}$F NMR (CD$_3$OD, 400 MHz): δ -75.50 (d, J=94 Hz).

Crystal seeds were obtained in the following manner to a solution of (S)-7-ethyl-N—((R)-1-(4-(ethylsulfonyl)phenyl)-2-hydroxyethyl)-6-((trans-4-(trifluoromethyl)cyclohexyl)methyl)-6,7-dihydro-5H-pyrrolo[3,4-b]pyridine-3-carboxamide (59.7 mg, 0.11 mmol) in ethyl acetate (0.5 mL) was added methanesulfonic acid (19.8 mg, 1.95 eq) dropwise. The salt oiled out. After decanting the top layer of ethyl acetate, the residue was dried over vacuum to remove any residual ethyl acetate. The residue was then redissolved in EtOH (~5 mL) by warming the solution up to give a clear solution. Crystals crashed out after standing at rt overnight (17.5 mg, 25%).

The following compounds in Table 1 were prepared according to the methods described herein. Where designated, an "*" indicates that although a single diastereomer was isolated, the absolute configuration about these positions was not fully characterized, however the relative stereochemistry at one of the designated positions to the other designated position is as shown. Accordingly, groups (pairs) of compounds exist (e.g., compounds 1 and 4; 2 and 5; 3 and 6; 10 and 11; 14 and 15; 18 and 21; 29 and 30; 34 and 42; and 39 and 42) where a single diastereomer was isolated and tested, but where the absolute stereochemistry about the "*" is arbitrarily defined. For example in compound 1, the trifluoromethyl group is trans relative to its connection to the dihydropyrrolopyridine core.

TABLE 1

| Cpd. No. | Structure | LC/MS (tR, method, m/z) | $^1$H NMR (CD$_3$OD) | $^{19}$F NMR (CD$_3$OD) | Intermediate Components |
|---|---|---|---|---|---|
| 1 | [structure] | 0.731 (1.5 min) 585.1 [M + H]$^+$ | 9.13 (s, 1H), 9.04 (d, J = 2.0 Hz, 1H), 8.34 (d, J = 2.0 Hz, 1H), 8.33 (d, J = 8.0 Hz, 1H), 7.79 (d, J = 8.0 Hz, 1H), 5.40 (t, J = 6.0 Hz, 1H), 5.18-5.12 (m, 1H), 4.76-4.65 (m, 2H), 4.29 (d, J = 10.0 Hz, 1H), 4.09-4.04 (m, 2H), 3.91-3.85 (m, 1H), 3.41-3.35 (m, 3H), 3.30 (q, J = 7.2 Hz, 2H), 2.62-2.53 (m, 1H), 2.32-2.18 (m, 2H), 1.94-1.89 (m, 1H), 1.73-1.63 (m, 1H), 1.52-1.41 (m, 1H), 1.33 (d, J = 6.8 Hz, 3H), 1.26 (t, J = 7.2 Hz, 3H), 1.09 (broad s, 3H). | | A1, B5, C2 |

TABLE 1-continued

| Cpd. No. | Structure | LC/MS (tR, method, m/z) | ¹H NMR (CD₃OD) | ¹⁹F NMR (CD₃OD) | Intermediate Components |
|---|---|---|---|---|---|
| 2 | 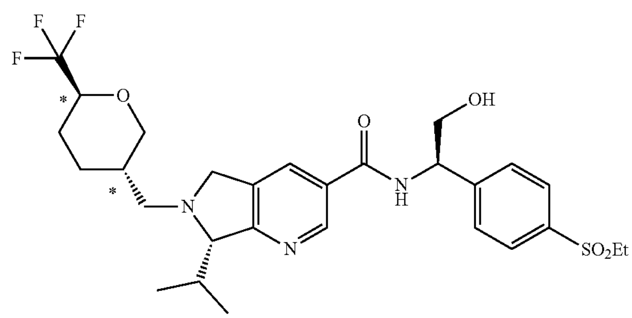 | 0.629 (1.5 min) 584.1 [M + H]⁺ | 9.12 (s, 1H), 8.28 (s, 1H), 7.90 (d, J = 8.0 Hz, 2H), 7.70 (d, J = 8.0 Hz, 2H), 5.30 (t, J = 6.4 Hz, 1H), 5.15-5.06 (m, 1H), 4.80-4.68 (m, 2H), 4.26 (d, J = 10.0 Hz, 1H), 3.92 (d, J = 6.4 Hz, 2H), 3.89 (m, 1H), 3.41-3.32 (m, 3H), 3.20 (q, J = 7.2 Hz, 2H), 2.66-2.52 (m, 1H), 2.38-2.17 (m, 2H), 1.92 (d, J = 12.4 Hz, 1H), 1.76-1.67 (m, 1H), 1.52-1.44 (m, 1H), 1.32 (d, J = 6.8 Hz, 3H), 1.21 (t, J = 7.2 Hz, 3H), 1.08 (broad s, 3H). | | A1, B1, C2 |
| 3 | 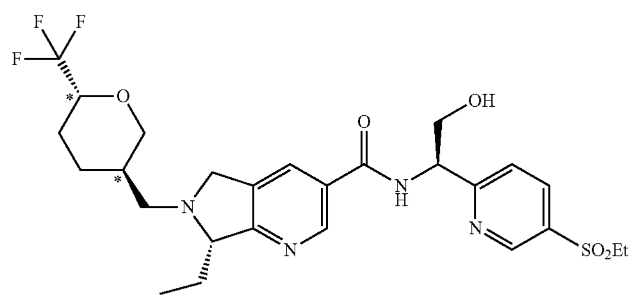 | 0.627 (1.5 min) 571.2 [M + H]⁺ | 9.12 (s, 1H), 9.06 (s, 1H), 8.35 (s, 1H), 8.34 (d, J = 8.0 Hz, 1H), 7.81 (d, J = 8.4 Hz, 1H), 5.41 (t, J = 6.0 Hz, 1H), 5.16-5.06 (m, 1H), 4.86-4.74 (m, 2H), 4.34-4.29 (m, 1H), 4.09-4.04 (m, 2H), 3.94-3.86 (m, 1H), 3.53-3.40 (m, 2H), 3.32 (q, J = 7.2 Hz, 2H), 2.38-2.18 (m, 4H), 1.96 (d, J = 12.8 Hz, 1H), 1.76-1.69 (m, 1H), 1.58-1.49 (m, 1H), 1.33 (broad s, 3H), 1.28 (t, J = 7.2 Hz, 3H). | −80.56 | A2, B5, C2 |
| 4 | 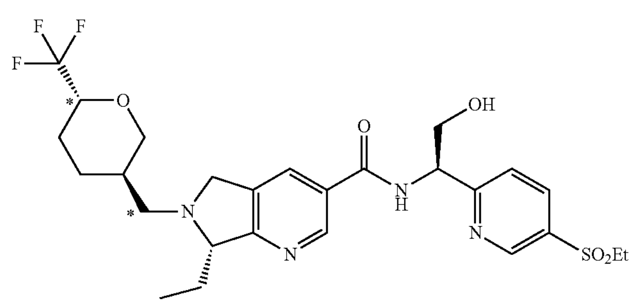 | 0.741 (1.5 min) 585.1 [M + H]⁺ | 9.13 (s, 1H), 9.04 (d, J = 2.0 Hz, 1H), 8.34 (d, J = 2.4 Hz, 1H), 8.33 (d, J = 8.4 Hz, 1H), 7.79 (d, J = 8.4 Hz, 1H), 5.40 (t, J = 6.0 Hz, 1H), 5.20-5.09 (m, 1H), 4.81-4.72 (m, 2H), 4.27 (d, J = 11.2 Hz, 1H), 4.07-4.03 (m, 2H), 3.92-3.85 (m, 1H), 3.41-3.35 (m, 3H), 3.29 (q, J = 7.2 Hz, 2H), 2.60-2.52 (m, 1H), 2.34-2.19 (m, 2H), 1.93 (d, J = 12.8 Hz, 1H), 1.72-1.64 (m, 1H), 1.58-1.46 (m, 1H), 1.32 (d, J = 7.2 Hz, 3H), 1.26 (t, J = 7.2 Hz, 3H), 1.07 (broad s, 3H). | | A1, B5, C2 |
| 5 | 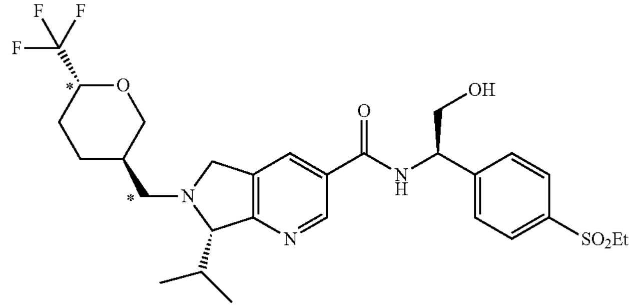 | 0.637 (1.5 min) 584.1 [M + H]⁺ | 9.12 (s, 1H), 8.29 (s, 1H), 7.90 (d, J = 8.4 Hz, 2H), 7.70 (d, J = 8.4 Hz, 2H), 5.30 (t, J = 6.0 Hz, 1H), 5.16-5.05 (m, 1H), 4.83-4.70 (m, 2H), 4.26 (d, J = 14.8 Hz, 1H), 3.92 (d, J = 6.4 Hz, 2H), 3.91-3.86 (m, 1H), 3.40-3.32 (m, 3H), 3.20 (q, J = 7.2 Hz, 2H), 2.58-2.47 (m, 1H), 2.33-2.16 (m, 2H), 1.93 (d, J = 12.8 Hz, 1H), 1.73-1.62 (m, 1H), 1.58-1.47 (m, 1H), 1.32 (d, J = 6.8 Hz, 3H), 1.21 (t, J = 7.2 Hz, 3H), 1.06 (broad s, 3H). | | A1, B1, C2 |

TABLE 1-continued

| Cpd. No. | Structure | LC/MS (tR, method, m/z) | ¹H NMR (CD₃OD) | ¹⁹F NMR (CD₃OD) | Intermediate Components |
|---|---|---|---|---|---|
| 6 | 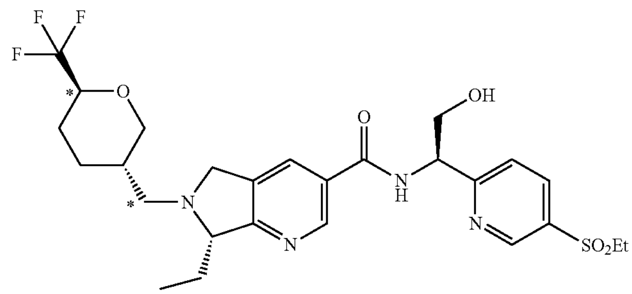 | 0.780 (2.0 min) 571.2 [M + H]⁺ | 9.12 (d, J = 2.0 Hz, 1H), 9.06 (d, J = 2.4 Hz, 1H), 8.34 (dd, J = 2.0 Hz, 8.4 Hz, 2H), 7.81 (d, J = 8.4 Hz, 1H), 5.41 (t, J = 6.4 Hz, 1H), 5.15-5.04 (m, 1H), 4.83-4.72 (m, 2H), 4.24 (d, J = 10.4 Hz, 1H), 4.09-4.05 (m, 2H), 3.96-3.89 (m, 1H), 3.44-3.36 (m, 2H), 3.32 (q, J = 7.2 Hz, 2H), 2.36-2.24 (m, 4H), 1.95 (d, J = 10.4 Hz, 1H), 1.76-1.69 (m, 1H), 1.54-1.46 (m, 1H), 1.35 (broad s, 3H), 1.28 (t, J = 7.2 Hz, 3H). | −80.57 | A2, B5, C2 |
| 7 | 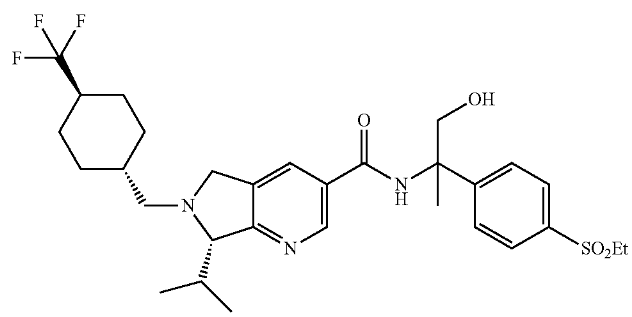 | 1.06 (2.0 min) 596.6 [M + H]⁺ | 9.11 (s, 1H), 8.73 (s, 1H), 8.26 (s, 1H), 7.91 (d, J = 8.4 Hz, 2H), 7.74 (d, J = 8.8 Hz, 2H), 5.01 (m, 1H), 3.90 (m, 2H), 3.23 (q, J = 7.2 Hz, 2H), 2.57 (m, 1H), 2.21 (m, 1H), 2.13-1.94 (m, 6H), 1.87 (s, 3H), 1.83 (m, 1H), 1.47 (m, 2H), 1.35 (d, J = 7.2 Hz, 3H), 1.26 (t, J = 7.2 Hz, 3H), 1.09 (s, 3H). | −75.4 | A1, B4, C1 Amide coupling of A1 and B4 was performed prior to treatment with oxone. |
| 8 | 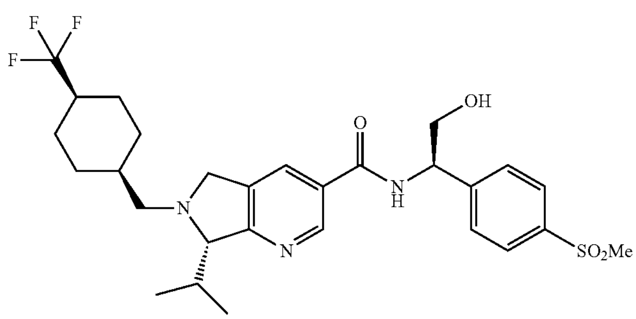 [SMILES: CC(C)[C@H]1c2ncc(C(=O)N[C@@H](CO)c3ccc(S(C)(=O)=O)cc3)cc2CN1C[C@H]1CC[C@@H](C(F)(F)F)CC1] | 0.634 (1.5 min) 568.1 [M + H]⁺ | 9.13 (s, 1H), 8.28 (s, 1H), 7.96 (d, J = 8.4 Hz, 2H), 7.71 (d, J = 8.4 Hz, 2H), 5.31 (t, J = 6.4 Hz, 1H), 5.16-5.07 (m, 1H), 4.85-4.74 (m, 2H), 3.93 (d, J = 7.2 Hz, 2H), 3.58-3.48 (m, 3H), 3.13 (s, 3H), 2.58-2.44 (m, 1H), 2.36-2.24 (m, 2H), 1.87-1.66 (m, 9H), 1.31 (broad s, 3H), 1.08 (broad s, 3H). | | A1, B6, C1 |
| 9 | 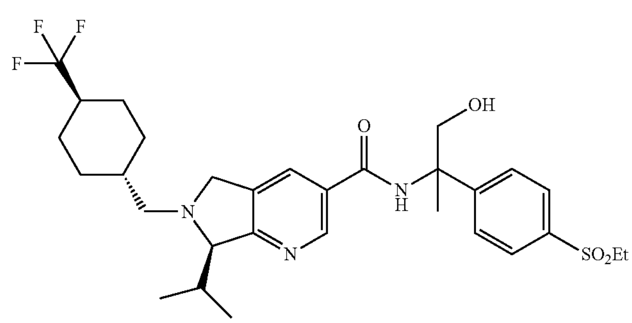 | 1.04 (2.0 min) 596.6 [M + H]⁺ | 9.05 (s, 1H), 8.66 (s, 1H), 8.20 (s, 1H), 7.86 (d, J = 8.4 Hz, 2H), 7.69 (d, J = 8.8 Hz, 2H), 3.92 (m, 2H), 3.17 (q, J = 7.6 Hz, 2H), 2.16 (m, 1H), 2.03 (m, 4H), 1.83 (s, 3H), 1.42 (m, 2H), 1.28 (d, J = 7.2 Hz, 3H), 1.22 (t, J = 7.6 Hz, 3H), 1.04 (m, 3H). | −75.4 | A1, B4, C1 Amide coupling of A1 and B4 was performed prior to treatment with oxone. |

TABLE 1-continued

| Cpd. No. | Structure | LC/MS (tR, method, m/z) | ¹H NMR (CD₃OD) | ¹⁹F NMR (CD₃OD) | Intermediate Components |
|---|---|---|---|---|---|
| 10 | 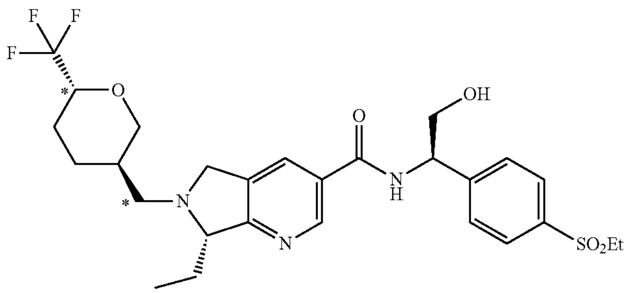 | 0.641 (1.5 min) 570.2 [M + H]⁺ | 9.10 (d, J = 1.6 Hz, 1H), 8.31 (s, 1H), 7.92 (d, J = 8.4 Hz, 2H), 7.72 (d, J = 8.4 Hz, 2H), 5.31 (t, J = 6.4 Hz, 1H), 5.20-5.10 (m, 1H), 4.83-4.73 (m, 2H), 4.34 (d, J = 10.0 Hz, 1H), 3.94 (d, J = 6.4 Hz, 2H), 3.93 (m, 1H), 3.51 (broad s, 1H), 3.40-3.33 (m, 2H), 3.21 (q, J = 7.2 Hz, 2H), 2.34-2.17 (m, 4H), 1.96 (d, J = 13.2 Hz, 1H), 1.77-1.66 (m, 1H), 1.63-1.47 (m, 1H), 1.34 (broad s, 3H), 1.23 (t, J = 7.2 Hz, 3H). | −80.56 | A2, B1, C2 |
| 11 | 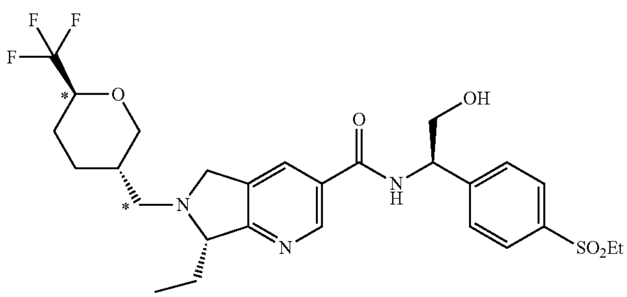 | 0.638 (1.5 min) 570.2 [M + H]⁺ | 9.10 (s, 1H), 8.31 (s, 1H), 7.92 (d, J = 8.4 Hz, 2H), 7.72 (d, J = 8.4 Hz, 2H), 5.31 (t, J = 6.4 Hz, 1H), 5.14-5.04 (m, 1H), 4.84-4.73 (m, 2H), 4.25-4.18 (m, 1H), 3.94 (d, J = 6.4 Hz, 2H), 3.91 (m, 1H), 3.46-3.34 (m, 3H), 3.21 (q, J = 7.6 Hz, 2H), 2.39-2.19 (m, 4H), 1.96 (d, J = 12.8 Hz, 1H), 1.78-1.67 (m, 1H), 1.56-1.46 (m, 1H), 1.35 (broad s, 3H), 1.23 (t, J = 7.6 Hz, 3H) | −80.57 | A2, B1, C2 |
| 12 | 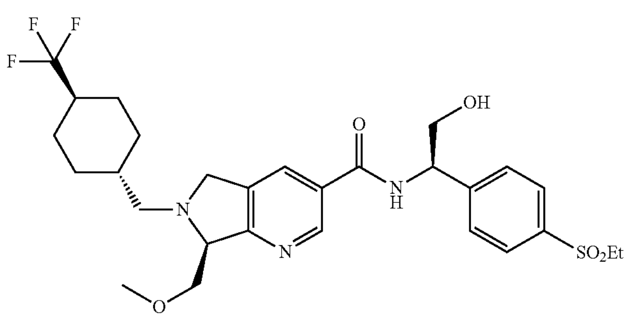 | 0.883 (2.0 min) 584.3 [M + H]⁺ | 9.11 (s, 1H), 8.30 (s, 1H), 7.92 (dd, J = 2.0 Hz, 8.4 Hz, 2H), 7.71 (d, J = 8.4 Hz, 2H), 5.31 (t, J = 6.4 Hz, 1H), 5.20-5.08 (m, 2H), 4.79-4.69 (m, 1H), 4.25-4.08 (m, 2H), 3.94 (d, J = 7.2 Hz, 2H), 3.60-3.38 (m, 4H), 3.22 (q, J = 7.6 Hz, 2H), 2.37-1.93 (m, 6H), 1.53-1.42 (m, 2H), 1.32-1.25 (m, 2H), 1.23 (t, J = 7.6 Hz, 3H). | −75.40 | A8, B1, C1 |
| 13 | 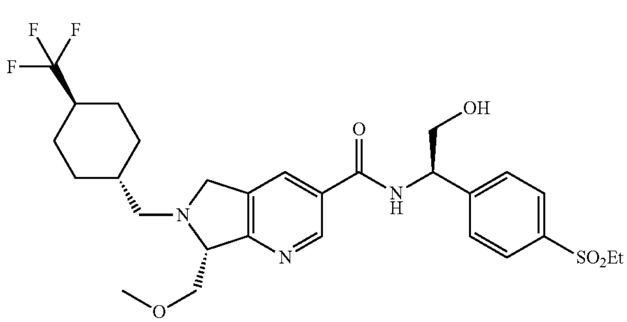 | 0.883 (2.0 min) 584.3 [M + H]⁺ | 9.12 (d, J = 2.0 Hz, 1H), 8.30 (s, 1H), 7.93 (dd, J = 2.0 Hz, 8.4 Hz, 2H), 7.71 (d, J = 8.4 Hz, 2H), 5.31 (t, J = 6.4 Hz, 1H), 5.21-5.11 (m, 2H), 4.81-4.71 (m, 1H), 4.24-4.06 (m, 2H), 3.94 (d, J = 7.2 Hz, 2H), 3.60-3.38 (m, 4H), 3.22 (q, J = 7.2 Hz, 2H), 2.29-1.93 (m, 6H), 1.55-1.41 (m, 2H), 1.32-1.24 (m, 2H), 1.23 (t, J = 7.2 Hz, 3H). | −75.40 | A8, B1, C1 |

TABLE 1-continued

| Cpd. No. | Structure | LC/MS (tR, method, m/z) | ¹H NMR (CD₃OD) | ¹⁹F NMR (CD₃OD) | Intermediate Components |
|---|---|---|---|---|---|
| 14 | (structure) | 0.664 (1.5 min) 584.1 [M + H]⁺ | 9.08 (s, 1H), 8.24 (s, 1H), 7.92 (d, J = 8.4 Hz, 2H), 7.71 (d, J = 8.4 Hz, 2H), 5.31 (t, J = 6.4 Hz, 1H), 5.11-5.04 (m, 1H), 4.86-4.76 (m, 2H), 4.21 (d, J = 8.8 Hz, 1H), 3.94 (d, J = 7.2 Hz, 2H), 3.83-3.75 (m, 1H), 3.53-3.46 (m, 3H), 3.22 (q, J = 7.2 Hz, 2H), 2.62-2.44 (m, 3H), 2.19-2.11 (m, 1H), 1.88-1.72 (m, 2H), 1.53-1.44 (m, 2H), 1.34-1.25 (m, 1H), 1.23 (t, J = 7.2 Hz, 3H), 1.13-1.04 (m, 3H). | −73.36 | A1, B1, C3 |
| 15 | (structure) | 0.655 (1.5 min) 584.0 [M + H]⁺ | 9.13 (s, 1H), 8.30 (s, 1H), 7.92 (d, J = 8.4 Hz, 2H), 7.72 (d, J = 8.4 Hz, 2H), 5.32 (t, J = 6.4 Hz, 1H), 5.15-5.08 (m, 1H), 4.84-4.74 (m, 2H), 4.30-4.21 (m, 1H), 3.98-3.90 (m, 3H), 3.59-3.41 (m, 3H), 3.22 (q, J = 7.2 Hz, 2H), 2.63-2.44 (m, 2H), 2.18-2.11 (m, 1H), 1.87-1.59 (m, 2H), 1.48-1.38 (m, 3H), 1.23 (t, J = 7.2 Hz, 3H), 1.18-1.05 (m, 3H). | −73.33 | A1, B1, C3 |
| 16 | (structure) | 0.641 (1.5 min) 555.0 [M + H]⁺ | 9.10 (s, 1H), 9.08 (d, J = 2.4 Hz, 1H), 8.33 (dd, J = 2.0 Hz, 8.4 Hz, 1H), 8.29 (s, 1H), 7.74 (d, J = 8.4 Hz, 1H), 5.38 (t, J = 6.0 Hz, 1H), 5.08 (d, J = 14.8 Hz, 1H), 4.83-4.71 (m, 2H), 4.07-4.03 (m, 2H), 3.49-3.33 (m, 2H), 3.20 (s, 3H), 2.24-1.93 (m, 8H), 1.48-1.38 (m, 2H), 1.36-1.18 (m, 5H). | −75.39 | A2, B7, C1 |
| 17 | (structure) | 0.811 (2.0 min) 570.2 [M + H]⁺ | 9.12 (s, 1H), 8.30 (s, 1H), 7.92 (d, J = 8.4 Hz, 2H), 7.71 (d, J = 8.4 Hz, 2H), 5.31 (t, J = 6.4 Hz, 1H), 5.16-5.05 (m, 2H), 4.81-4.71 (m, 1H), 4.38-4.28 (m, 2H), 3.94 (d, J = 7.2 Hz, 2H), 3.70-3.38 (m, 2H), 3.22 (q, J = 7.2 Hz, 2H), 2.29-1.96 (m, 6H), 1.53-1.38 (m, 2H), 1.31-1.25 (m, 2H), 1.23 (t, J = 7.2 Hz, 3H). | −75.40 | A7, B1, C1 Removal of the TBS group was performed in the same step as Boc deprotection |

TABLE 1-continued

| Cpd. No. | Structure | LC/MS (tR, method, m/z) | $^1$H NMR (CD$_3$OD) | $^{19}$F NMR (CD$_3$OD) | Intermediate Components |
|---|---|---|---|---|---|
| 18 | 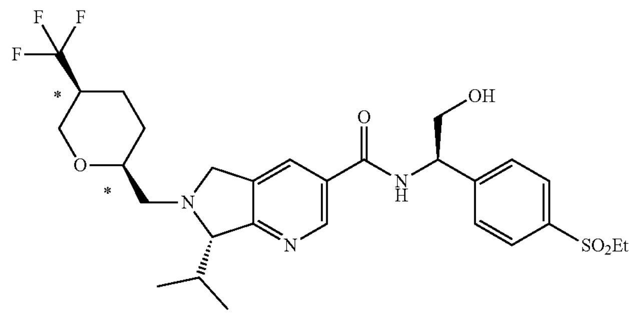 | 0.655 (1.5 min) 584.0 [M + H]$^+$ | 9.10 (s, 1H), 8.27 (s, 1H), 7.90 (d, J = 8.4 Hz, 2H), 7.70 (d, J = 8.4 Hz, 2H), 5.29 (t, J = 6.4 Hz, 1H), 5.14-4.95 (m, 2H), 4.85-4.74 (m, 1H), 4.26 (d, J = 14.0 Hz, 2H), 3.96 (broad s, 1H), 3.92 (d, J = 6.4 Hz, 2H), 3.74-3.53 (m, 3H), 3.20 (q, J = 7.2 Hz, 2H), 2.55-2.36 (m, 2H), 2.20-1.95 (m, 2H), 1.62 (broad s, 2H), 1.30 (d, J = 6.8 Hz, 3H), 1.21 (t, J = 7.2 Hz, 3H), 1.11 (broad s, 3H). | −68.553 | A1, B1, C3 |
| 19 | 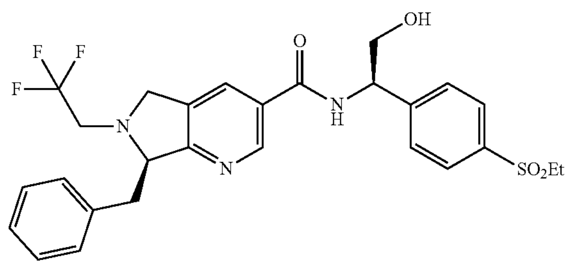 | 0.787 (1.5 min) 548.0 [M + H]$^+$ | 9.01 (s, 1H), 8.22 (s, 1H), 7.92 (d, J = 8.4 Hz, 2H), 7.70 (d, J = 8.4 Hz, 2H), 5.29 (t, J = 6.4 Hz, 1H), 4.74 (broad s, 1H), 4.36 (d, J = 14.4 Hz, 1H), 4.06 (d, J = 14.4 Hz, 1H), 3.91 (d, J = 6.0 Hz, 2H), 3.54-3.39 (m, 3H), 3.22 (q, J = 7.2 Hz, 2H), 3.20 (m, 1H), 1.23 (t, J = 7.2 Hz). | −71.60 | A5, B1 |
| 20 | 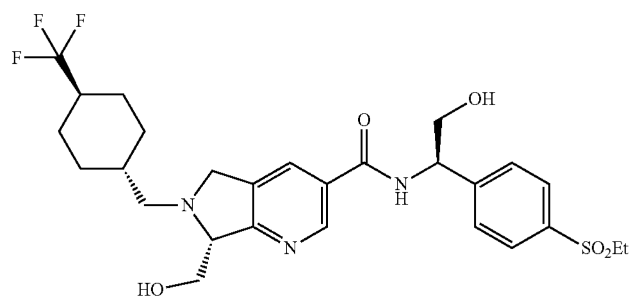 | 0.809 (2.0 min) 570.2 [M + H]$^+$ | 9.12 (s, 1H), 8.30 (s, 1H), 7.92 (d, J = 8.4 Hz, 2H), 7.72 (d, J = 8.4 Hz, 2H), 5.32 (t, J = 6.4 Hz, 1H), 5.18-5.05 (m, 2H), 4.85-4.81 (m, 1H), 4.38-4.28 (m, 2H), 3.94 (d, J = 6.4 Hz, 2H), 3.64-3.35 (m, 2H), 3.22 (q, J = 7.2 Hz, 2H), 2.27-1.94 (m, 6H), 1.52-1.42 (m, 2H), 1.31-1.25 (m, 2H), 1.23 (t, J = 7.2 Hz, 3H). | −75.40 | A7, B1, C1 Removal of the TBS group was performed in the same step as Boc deprotection |
| 21 | 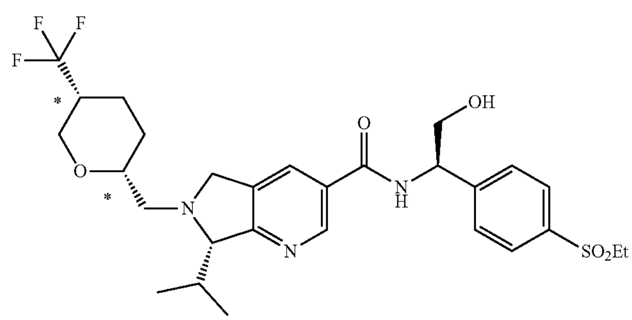 | 0.641 (1.5 min) 584.0 [M + H]$^+$ | 9.12 (s, 1H), 8.32 (s, 1H), 7.92 (d, J = 8.4 Hz, 2H), 7.72 (d, J = 8.4 Hz, 2H), 5.31 (t, J = 6.4 Hz, 1H), 5.13-4.94 (m, 2H), 4.85-4.76 (m, 1H), 4.29 (d, J = 12.0 Hz, 2H), 4.01 (broad s, 1H), 3.94 (d, J = 6.0 Hz, 2H), 3.73-3.44 (m, 3H), 3.22 (q, J = 7.6 Hz, 2H), 2.55-2.40 (m, 2H), 2.23-1.94 (m, 2H), 1.98 (broad s, 2H), 1.31-1.25 (m, 3H), 1.23 (t, J = 7.6 Hz, 3H), 1.08 (broad s, 3H). | −68.515 | A1, B1, C3 |
| 22 | 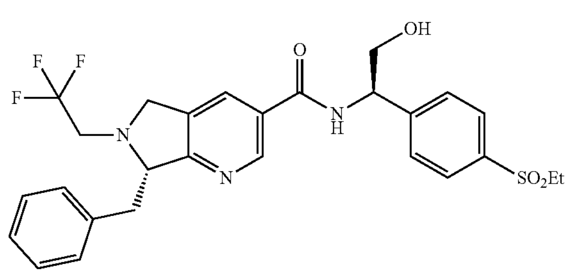 | 0.787 (1.5 min) 548.0 [M + H]$^+$ | 9.01 (s, 1H), 8.22 (s, 1H), 7.92 (d, J = 8.4 Hz, 2H), 7.70 (d, J = 8.4 Hz, 2H), 5.29 (t, J = 6.4 Hz, 1H), 4.74 (broad s, 1H), 4.36 (d, J = 14.4 Hz, 1H), 4.06 (d, J = 14.4 Hz, 1H), 3.91 (d, J = 6.8 Hz, 2H), 3.54-3.42 (m, 3H), 3.22 (q, J = 7.2 Hz, 2H), 3.20 (m, 1H), 1.23 (t, J = 7.2 Hz). | −71.593 | A5, B1 |

TABLE 1-continued

| Cpd. No. | Structure | LC/MS (tR, method, m/z) | ¹H NMR (CD₃OD) | ¹⁹F NMR (CD₃OD) | Intermediate Components |
|---|---|---|---|---|---|
| 23 | (structure) | 1.116 (2.0 min) 608.2 [M + H]⁺ | 8.97 (d, J = 5.2 Hz, 1H), 8.21 (s, 1H), 7.92 (d, J = 8.4 Hz, 2H), 7.71 (d, J = 8.4 Hz, 2H), 5.31 (t, J = 6.4 Hz, 1H), 4.75-4.70 (m, 1H), 4.55 (d, J = 14.4 Hz, 1H), 3.95 (s, 1H), 3.93 (d, J = 6.4 Hz, 2H), 3.22 (q, J = 7.6 Hz, 2H), 2.84 (d, J = 7.6 Hz, 2H), 2.26-1.94 (m, 5H), 1.68-1.57 (m, 1H), 1.42-1.34 (m, 2H), 1.23 (t, J = 7.6 Hz, 3H), 1.11-0.94 (m, 2H). | −75.309, −75.491 | A9, B1, C1 |
| 24 | (structure) | 0.608 (1.5 min) 554.1 [M + H]⁺ | 9.18 (d, J = 7.2 Hz, 1H), 9.09 (s, 1H), 8.28 (s, 1H), 7.95 (d, J = 8.4 Hz, 2H), 7.69 (d, J = 8.4 Hz, 2H), 5.32-5.27 (m, 1H), 5.09 (d, J = 14.4 Hz, 1H), 4.83-4.65 (m, 2H), 3.92 (d, J = 6.8 Hz, 2H), 3.47-3.39 (m, 2H), 3.11 (s, 3H), 2.23-1.98 (m, 10H), 1.48-1.32 (m, 5H). | −75.39 | A2, B6, C1 |
| 25 | (structure) | 0.643 (1.5 min) 568.0 [M + H]⁺ | 9.10 (s, 1H), 8.26 (s, 1H), 7.95 (d, J = 8.8 Hz, 2H), 7.69 (d, J = 8.4 Hz, 2H), 5.29 (t, J = 6.4 Hz, 1H), 5.15-5.10 (m, 1H), 4.72-4.65 (m, 1H), 3.92 (d, J = 6.4 Hz, 2H), 3.35-3.30 (m, 3H), 3.11 (s, 3H), 2.55-2.45 (m, 1H), 2.19-1.95 (m, 6H), 1.48-1.08 (m, 11H). | | A1, B6, C1 |
| 26 | (structure) | 0.832 (2.0 min) 554.1 [M + H]⁺ | 9.06-9.14 (m, 1H), 8.27-8.35 (m, 1H), 7.86-7.96 (m, 2H), 7.67-7.76 (m, 2H), 5.27-5.35 (m, 1H), 5.04-5.15 (m, 2H), 4.65-4.77 (m, 1H), 3.90-3.98 (m, 2H), 3.48-3.60 (m, 1H), 3.38-3.46 (m, 1H), 3.14-3.27 (m, 2H), 1.95-2.28 (m, 7H), 1.83-1.92 (m, 2H), 1.41-1.56 (m, 2H), 1.17-1.33 (m, 5H). | −75.36 | A6, B1, C1 |

TABLE 1-continued

| Cpd. No. | Structure | LC/MS (tR, method, m/z) | ¹H NMR (CD₃OD) | ¹⁹F NMR (CD₃OD) | Intermediate Components |
|---|---|---|---|---|---|
| 27 | 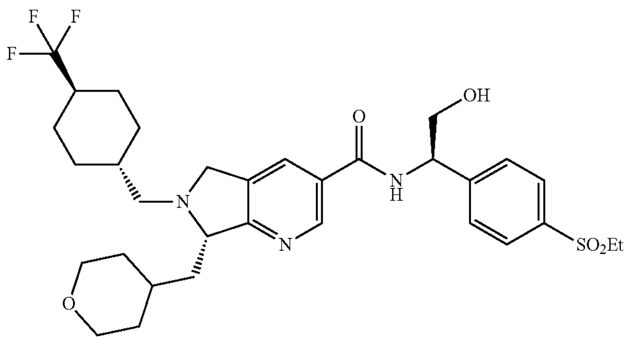 | 0.869 (2.0 min) 638.3 [M + H]⁺ | 9.16-9.18 (d, J = 7.2 Hz, 1H), 9.07 (s, 1H), 8.25 (s, 1H), 7.87-7.89 (d, J = 8.0 Hz, 2H), 7.66-7.68 (d, J = 8.4 Hz, 2H), 5.27-5.29 (m, 1H), 4.97-5.07 (m, 4H), 3.90-3.98 (m, 2H), 3.88-3.89 (m, 2H), 3.43-3.49 (m, 4H), 3.17-3.21 (d, J = 7.6 Hz, 2H), 1.71-2.13 (m, 13H), 0.96-1.45 (m, 9H). | −75.39 | A4, B1, C1 |
| 28 | 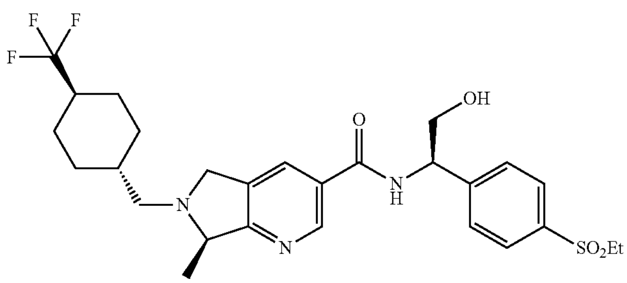 | 0.834 (2.0 min) 554.1 [M + H]⁺ | 9.09-9.12 (m, 1H), 8.29-8.33 (m, 1H), 7.89-7.95 (m, 2H), 7.68-7.75 (m, 2H), 5.28-5.35 (m, 1H), 5.06-5.14 (m, 2H), 4.66-4.75 (m, 1H), 3.92-3.96 (d, J = 6.4 Hz, 2H), 3.51-3.60 (m, 1H), 3.38-3.45 (m, 1H), 3.18-3.25 (m, 2H), 1.94-2.30 (m, 7H), 1.85-1.91 (m, 2H), 1.41-1.56 (m, 2H), 1.16-1.30 (m, 5H). | −75.38 | A6, B1, C1 |
| 29 | 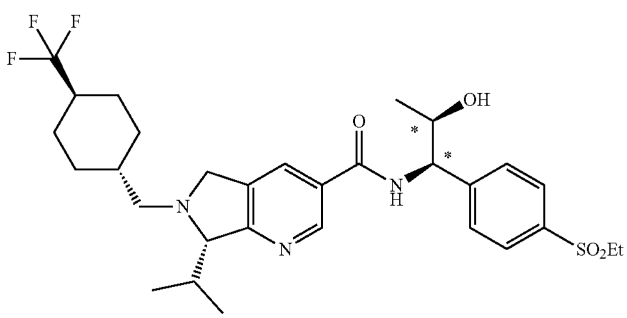 | 0.644 (1.5 min) 596.1 [M + H]⁺ | 8.86 (s, 1H), 8.61 (d, J = 8.4 Hz, 1H), 8.07 (s, 1H), 7.84 (d, J = 8.4 Hz, 2H), 7.70 (d, J = 8.4 Hz, 2H), 5.20-5.00 (m, 3H), 4.75-4.60 (m, 1H), 4.36 (q, J = 6.4 Hz, 1H), 3.50-3.35 (m, 2H), 3.17 (q, J = 7.2 Hz, 2H), 2.55-2.40 (m, 1H), 2.25-1.85 (m, 7H), 1.50-1.35 (m, 3H), 1.35-1.00 (m, 12H). | | A1, B3, C1 |
| 30 | 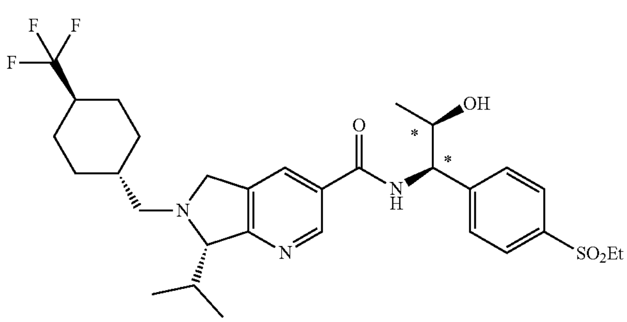 | 0.644 (1.5 min) 596.2 [M + H]⁺ | 8.87 (s, 1H), 8.65-8.58 (m, 1H), 8.06 (s, 1H), 7.86 (d, J = 8.4 Hz, 2H), 7.71 (d, J = 8.4 Hz, 2H), 5.25-4.95 (m, 3H), 4.75-4.60 (m, 1H), 4.37 (q, J = 6.4 Hz, 1H), 3.50-3.35 (m, 2H), 3.18 (q, J = 7.2 Hz, 2H), 2.55-2.43 (m, 1H), 2.25-1.90 (m, 7H), 1.50-1.35 (m, 3H), 1.35-1.00 (m, 12H). | | A1, B3, C1 |

TABLE 1-continued

| Cpd. No. | Structure | LC/MS (tR, method, m/z) | ¹H NMR (CD₃OD) | ¹⁹F NMR (CD₃OD) | Intermediate Components |
|---|---|---|---|---|---|
| 31 | 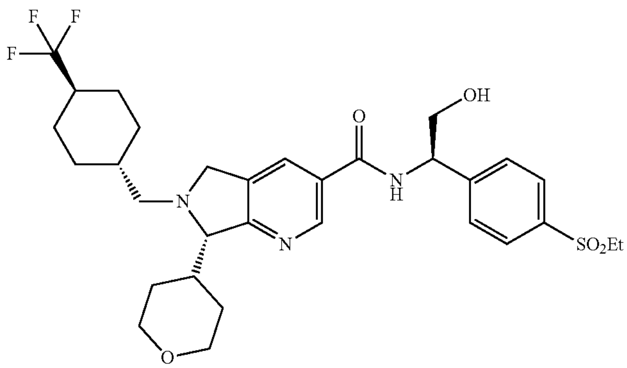 | 0.609 (1.5 min) 624.1 [M + H]⁺ | 9.14-9.15 (d, J = 1.6 Hz, 1H), 8.30 (s, 1H), 7.91-7.95 (d, J = 6.4 Hz, 2H), 7.71-7.73 (d, J = 8.0 Hz, 2H), 5.05-5.35 (m, 2H), 4.73-4.77 (m, 2H), 3.91-4.08 (m, 4H), 3.42-3.50 (m, 2H), 3.21-3.23 (d, J = 7.2 Hz, 2H), 1.69-2.23 (m, 11H), 1.17-1.49 (m, 9H). | −75.407 | A3, B1, C1 |
| 32 | 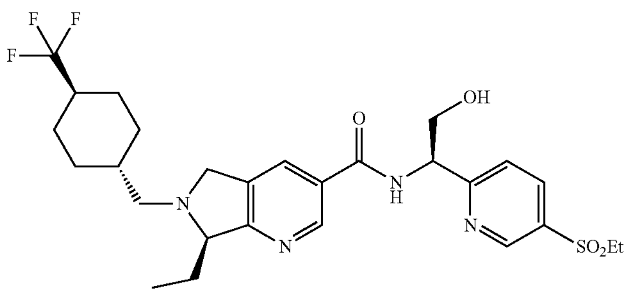 | 0.748 (1.5 min) 569.2 [M + H]⁺ | 9.11-9.12 (d, J = 1.2 Hz 1H), 9.06-9.07 (d, J = 2.4 Hz, 1H), 8.36-8.39 (m, 1H), 8.33 (s, 1H), 7.82-7.86 (d, J = 8.4 Hz, 1H), 5.40-5.43 (t, J = 5.6 Hz, 1H), 5.11-5.15 (d, J = 14.4 Hz, 1H), 4.75-4.90 (m, 2H), 4.07-4.11 (m, 2H), 3.35-3.44 (m, 4H), 2.01-2.28 (m, 8H), 1.19-1.50 (m, 10H). | −75.39 | A2, B5, C1 |
| 33 | 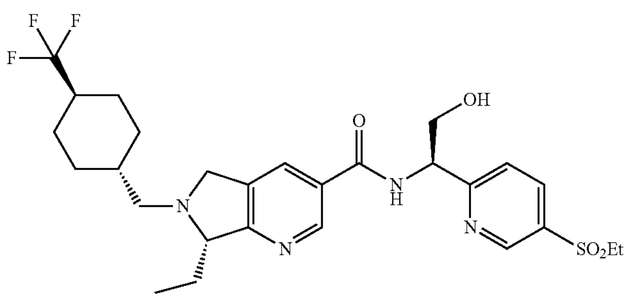 | 0.647 (1.5 min) 569.1 [M + H]⁺ | 9.12 (s, 1H), 9.08-9.09 (d, J = 1.2 Hz, 1H), 8.40-8.42 (d, J = 8.0 Hz, 1H), 8.34 (s, 1H), 7.86-7.89 (d, J = 8.4 Hz, 1H), 5.40-5.43 (t, J = 5.6 Hz, 1H), 5.12-5.16 (d, J = 14.8 Hz, 1H), 4.84-4.90 (m, 2H), 4.08-4.10 (m, 2H), 3.35-3.44 (m, 4H), 2.05-2.28 (m, 8H), 1.19-1.50 (m, 10H). | −75.38 | A2, B5, C1 |
| 34 | 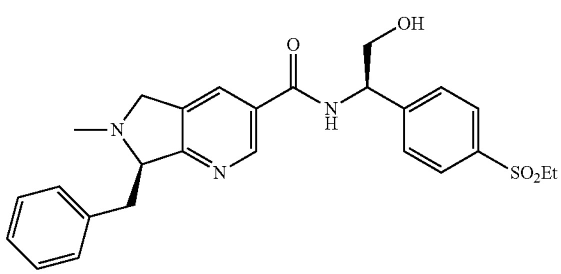 | 0.574 (1.5 min) 480.0 [M + H]⁺ | 9.14 (s, 1H), 8.30 (s, 1H), 7.93-7.91 (d, J = 8.4 Hz, 2H), 7.73-7.71 (d, J = 8.4 Hz, 2H), 7.47-7.36 (m, 5H), 5.51-5.23 (m, 2H), 4.93-4.91 (m, 2H), 4.62-4.58 (m, 1H), 3.95-3.93 (d, J = 8.4 Hz, 2H), 3.92-3.89 (m, 1H), 3.33-3.32 (m, 1H), 3.25-3.19 (q, J = 7.6 Hz, 2H), 2.87 (s, 3H), 1.25-1.21 (t, J = 7.2 Hz, 3H). | | A5, B1 |
| 35 | 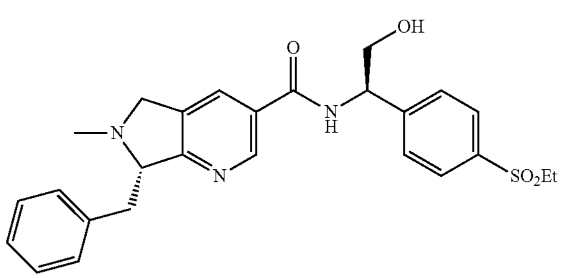 | 0.578 (1.5 min) 480.0 [M + H]⁺ | 9.14 (s, 1H), 8.30 (s, 1H), 7.93-7.91 (d, J = 8.4 Hz, 2H), 7.73-7.71 (d, J = 8.4 Hz, 2H), 7.47-7.36 (m, 5H), 5.33-5.23 (m, 2H), 4.97-4.92 (m, 2H), 4.62-4.59 (m, 1H), 3.95-3.93 (d, J = 8.4 Hz, 2H), 3.92-3.89 (m, 1H), 3.33-3.32 (m, 1H), 3.25-3.19 (q, J = 7.6 Hz, 2H), 2.87 (s, 3H), 1.25-1.21 (t, J = 7.2 Hz, 3H). | | A5, B1 |

TABLE 1-continued

| Cpd. No. | Structure | LC/MS (tR, method, m/z) | ¹H NMR (CD₃OD) | ¹⁹F NMR (CD₃OD) | Intermediate Components |
|---|---|---|---|---|---|
| 36 | 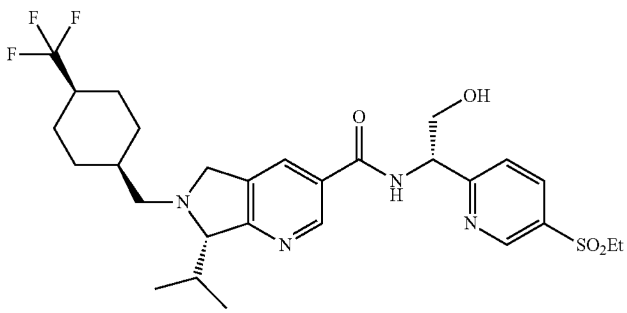 | 0.617 (1.5 min) 583.1 [M + H]⁺ | 9.11 (s, 1H), 9.02 (s, 1H), 8.35-8.26 (m, 2H), 7.74 (d, J = 8.4 Hz, 1H), 5.38 (t, J = 6.0 Hz, 1H), 5.18-5.08 (m, 1H), 5.05-4.94 (m, 1H), 4.80-4.67 (m, 1H), 4.08-4.01 (m, 2H), 3.55-3.45 (m, 2H), 3.27 (q, J = 7.6 Hz, 2H), 2.56-2.47 (m, 1H), 2.37-2.23 (m, 2H), 2.07-2.00 (m, 1H), 1.95-1.60 (m, 7H), 1.30 (d, J = 6.8 Hz, 3H), 1.24 (t, J = 7.6 Hz, 3H), 1.07 (d, J = 6.8 Hz, 3H). | | A1, B5, C1 |
| 37 | 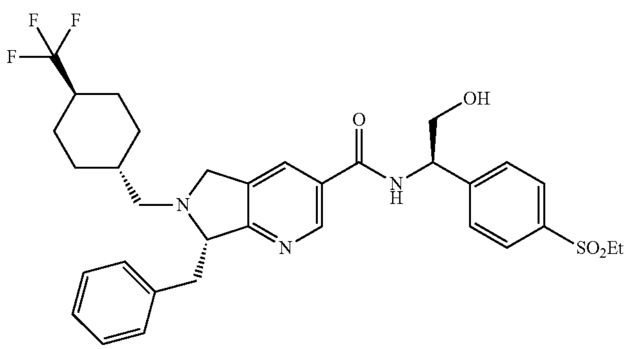 | 0.660 (1.5 min) 630.1 [M + H]⁺ | 9.15 (s, 1H), 8.32 (s, 1H), 7.94-7.92 (d, J = 8.4 Hz, 2H), 7.73-7.71 (d, J = 8.4 Hz, 2H), 7.54-7.41 (m, 5H), 5.34-5.28 (m, 2H), 5.22-5.18 (d, J = 14.4 Hz, 1H), 4.71-4.67 (d, J = 14.4 Hz, 1H), 3.98-3.93 (m, 3H), 3.25-3.19 (m, 4H), 2.66-2.64 (m, 1H), 2.05-1.90 (m, 4H), 1.71-1.68 (m, 2H), 1.36-1.29 (m, 2H), 1.25-121 (t, J = 7.2 Hz, 3H), 0.88-0.82 (m, 2H). | −75.445 | A5, B1, C1 |
| 38 | 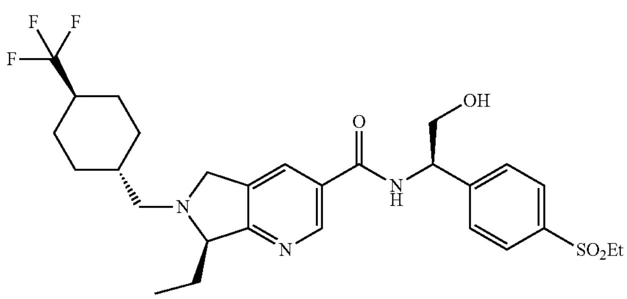 | 0.745 (1.5 min) 568.3 [M + H]⁺ | 9.11 (s, 1H), 8.29 (s, 1H), 7.90-7.94 (d, J = 8.4 Hz, 2H), 7.72 (d, J = 8.0 Hz, 2H), 5.28-5.35 (t, J = 6.4, Hz, 2H), 5.04-5.15 (m, 1H), 4.68-4.83 (m, 2H), 3.91-3.96 (m, 2H), 3.37-3.53 (m, 2H), 3.20-3.24 (d, J = 7.2 Hz, 2H), 1.96-2.28 (m, 8H), 1.20-1.50 (m, 10H). | −75.407 | A2, B1, C1 |
| 39 | 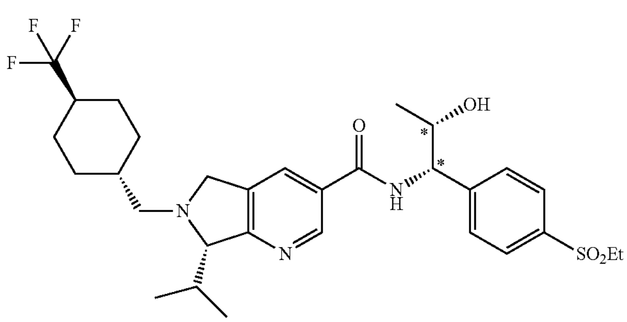 | 0.631 (1.5 min) 596.1 [M + H]⁺ | 9.10 (s, 1H), 9.04 (d, J = 8.0 Hz, 1H), 8.26 (s, 1H), 7.89 (d, J = 8.0 Hz, 2H), 7.70 (d, J = 8.4 Hz, 2H), 5.20-5.00 (m, 3H), 4.75-4.65 (m, 1H), 4.18 (t, J = 6.4 Hz, 1H), 3.50-3.35 (m, 2H), 3.20 (q, J = 7.6 Hz, 2H), 2.60-2.45 (m, 1H), 2.25-1.90 (m, 7H), 1.55-1.35 (m, 3H), 1.35-1.00 (m, 12H). | | A1, B2, C1 |

TABLE 1-continued

| Cpd. No. | Structure | LC/MS (tR, method, m/z) | ¹H NMR (CD₃OD) | ¹⁹F NMR (CD₃OD) | Intermediate Components |
|---|---|---|---|---|---|
| 40 | 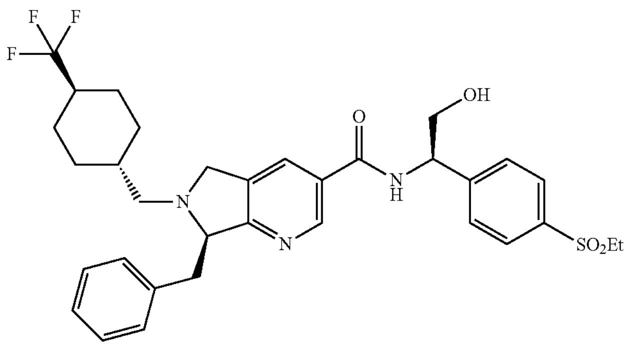 | 0.651 (1.5 min) 630.1 [M + H]⁺ | 9.15 (s, 1H), 8.32 (s, 1H), 7.93-7.91 (d, J = 8.4 Hz, 2H), 7.73-7.71 (d, J = 8.4 Hz, 2H), 7.55-7.41 (m, 5H), 5.34-5.28 (m, 2H), 5.22-5.18 (d, J = 14.8 Hz, 1H), 4.89-4.86 (d, J = 14.8 Hz, 1H), 3.98-3.93 (m, 3H), 3.25-3.19 (m, 4H), 2.66-2.60 (m, 1H), 2.05-1.90 (m, 4H), 1.71-1.68 (m, 2H), 1.36-1.29 (m, 2H), 1.25-121 (t, J = 7.2 Hz, 3H), 0.88-0.82 (m, 2H). | −75.445 | A5, B1, C1 |
| 42 | 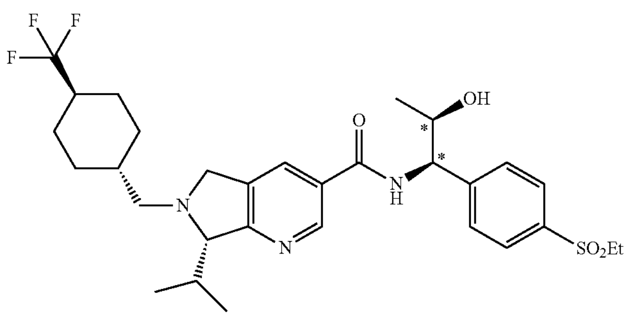 | 0.775 (1.5 min) 596.3 [M + H]⁺ | 9.07 (s, 1H), 8.28 (s, 1H), 7.89 (d, J = 8.4 Hz, 2H), 7.71 (d, J = 8.0 Hz, 2H), 5.25-5.07 (m, 3H), 4.75-4.65 (m, 1H), 4.19 (t, J = 6.0 Hz, 1H), 3.45-3.35 (m, 2H), 3.19 (q, J = 7.2 Hz, 2H), 2.60-2.50 (m, 1H), 2.25-1.90 (m, 7H), 1.55-1.35 (m, 3H), 1.35-1.00 (m, 12H). | | A1, B2, C1 |
| 43 | 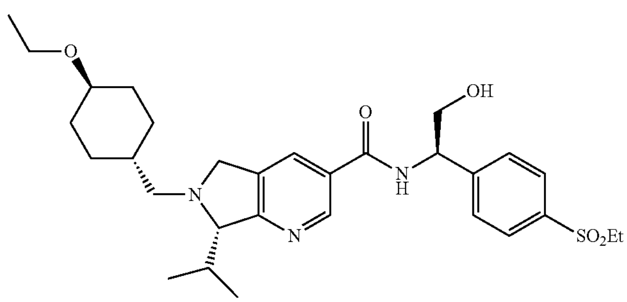 | 0.718 (1.5 min) 558.4 [M + H]⁺ | 9.20-9.14 (m, 1H), 9.10 (s, 1H), 8.25 (s, 1H), 7.89 (d, J = 8.4 Hz, 2H), 7.68 (d, J = 8.0 Hz, 2H), 5.35-5.25 (m, 1H), 5.11-5.04 (m, 1H), 4.75-4.64 (m, 2H), 3.95-3.85 (m, 2H), 3.54 (q, J = 7.2 Hz, 2H), 3.42-3.30 (m, 3H), 3.19 (q, J = 7.6 Hz, 2H), 2.55-2.43 (m, 1H), 2.18-2.07 (m, 2H), 2.01-1.86 (m, 3H), 1.29 (d, J = 6.8 Hz, 3H), 1.28-1.20 (m, 3H), 1.20 (t, J = 7.6 Hz, 3H), 1.17 (t, J = 7.2 Hz, 3H), 1.07 (d, J = 6.8 Hz, 3H). | | A1, B1 |
| 44 | 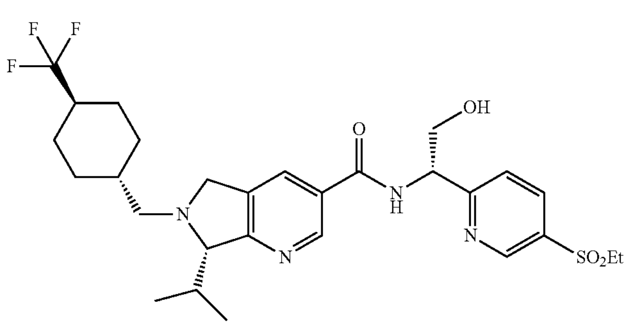 | 0.620 (1.5 min) 583.1 [M + H]⁺ | 9.11 (s, 1H), 9.01 (s, 1H), 8.31-8.24 (m, 2H), 7.73 (d, J = 8.4 Hz, 1H), 5.38 (t, J = 6.0 Hz, 1H), 5.13-5.06 (m, 1H), 4.85-4.75 (m, 2H), 4.75-4.67 (m, 1H), 4.10-4.03 (m, 2H), 3.45-3.36 (m, 1H), 3.30 (q, J = 7.6 Hz, 2H), 2.56-2.47 (m, 1H), 2.25-1.92 (m, 7H), 1.52-1.37 (m, 2H), 1.30 (d, J = 6.8 Hz, 3H), 1.24 (t, J = 7.6 Hz, 3H), 1.22-1.15 (m, 1H), 1.08 (d, J = 6.8 Hz, 3H). | | A1, B5, C1 |

| Cpd. No. | Structure | LC/MS (tR, method, m/z) | $^1$H NMR (CD$_3$OD) | $^{19}$F NMR (CD$_3$OD) | Intermediate Components |
|---|---|---|---|---|---|
| 45 | (structure with difluorocyclohexyl, pyrrolopyridine, isopropyl, pyridyl-SO$_2$Et, hydroxymethyl amide) | 0.625 (1.5 min) 583.1 [M + H]$^+$ | 9.11 (s, 1H), 9.03 (s, 1H), 8.35-8.25 (m, 2H), 7.78 (d, J = 8.4 Hz, 1H), 5.39 (t, J = 6.0 Hz, 1H), 5.18-5.09 (m, 1H), 4.88-4.81 (m, 2H), 4.75-4.65 (m, 1H), 4.10-4.03 (m, 2H), 3.45-3.36 (m, 1H), 3.32 (q, J = 7.6 Hz, 2H), 2.56-2.47 (m, 1H), 2.25-1.92 (m, 7H), 1.52-1.37 (m, 2H), 1.30 (d, J = 6.8 Hz, 3H), 1.24 (t, J = 7.6 Hz, 3H), 1.22-1.15 (m, 1H), 1.08 (d, J = 6.8 Hz, 3H). | | A1, B5, C1 |
| 47 | (structure with difluorocyclohexyl, pyrrolopyridine, isopropyl, phenyl-SO$_2$Et, hydroxymethyl amide) | 0.761 (1.5 min) 582.3 [M + H]$^+$ | 9.19-9.21 (d, J = 6.8 Hz, 1H), 9.12-9.13 (d, J = 2.0 Hz, 1H), 8.30-8.31 (d, J = 2.0 Hz, 1H), 7.90-7.95 (m, 2H), 7.71-7.73 (d, J = 8.0 Hz, 2H), 5.27-5.35 (m, 1H), 5.14-5.18 (d, J = 15.6 Hz, 1H), 4.71-4.75 (d, J = 15.2 Hz, 1H), 3.91-3.96 (m, 2H), 3.34-3.47 (m, 2H), 3.20-3.25 (q, J = 7.2 Hz, 1H), 2.54-2.56 (m, 1H), 2.07 (m, 6H), 1.08-1.52 (m, 14H). | | A1, B1, C1 |

Biological Assays

Radio-Ligand RORγ Binding Assay (Assay 1)

Compounds of the present invention were tested for ability to bind to RORγ in a cell-free competition assay with commercially available radio-ligand (RL), 25-hydroxy[26, 27-$^3$H]-cholesterol (PerkinElmer, Cat. # NET674250UC), for a ligand binding site on a recombinant RORγ Ligand Binding Domain (LBD) protein expressed as a 6xHis-Glutathione-S-Transferase (GST) fusion. The assay was performed in 96-well SPA plates (PerkinElmer, Cat. #1450-401) in 50 mM HEPES buffer, pH 7.4, containing 150 mM NaCl, 5 mM MgCl$_2$, 10% (v/v) glycerol, 2 mM CHAPS, 0.5 mM β-octylglucopyranoside and 5 mM DTT. Tested compounds were dissolved in DMSO, and semi-log (3.162x) serial dilutions of the compounds were prepared in the same solvent. Two μL of the DMSO solutions were mixed with 28 μL of 8.6 nM 25-hydroxy[26,27-$^3$H]-cholesterol and 50 μL of 24 nM RORγ LBD. The plate was shaken at 700 rpm for 20 min and incubated for 10 min at rt, after which 40 μL of poly-Lys YSi SPA beads (PerkinElmer, Cat. # RPNQ0010) were added to achieve 50 μg of the beads per well. The plate was incubated on an orbital shaker for 20 min and then for 10 min without agitation at rt. SPA signal for tritium beta radiation was registered on PerkinElmer Microbeta plate reader. Percent inhibition values were calculated based on the high signal obtained with DMSO control and the low signal observed with 10 μM standard RORγ inverse agonist T0901317 (SigmaAldrich, Cat. # T2320). The percent inhibition vs. concentration data were fit into a four-parameter model, and IC50 values were calculated from the fit as the concentrations corresponding to the inflection points on the dose-response curves Inhibitory constants (Ki) were calculated using the following equation, where [RL] is the concentration in the assay and K$_D$ is a dissociation constant of 25-hydroxy[26,27-$^3$H]-cholesterol:

$$K_i = \frac{IC_{50}}{\left(1 + \frac{[RL]}{K_D}\right)}$$

RORγ t 5xRORE Assay in Jurkat Cells (Assay 2)

Compounds of the present invention were tested for RORγ inverse agonist activity in a cell-based, transcriptional activity assay. Secreted Nanoluc® luciferase was used as a reporter for transcriptional activity of the full-length RORγ t in Jurkat cells (ATCC, Cat. # TIB-152). A reporter plasmid was constructed by inserting 5 repeats of the ROR Response Element (RORE) AAAGTAGGTCA (SEQ ID NO:1) into a commercially available promoterless plasmid pNL1.3 [secNluc] (Promega, Cat. # N1021) using KpnI and HindIII restriction sites. The expression plasmid for RORγ t was purchased (GeneCopoeia, Cat. # EX-T6988-MO2). Jurkat cells (30 million cells) were transfected with 11 μg of EX-T6988-MO2 and 26 μg of the reporter plasmid in OptiMEM® media using Lipofectamine® LTX and Plus™ reagents (Life Technologies, Cat. #15338-100). After 5-6 hr incubation at 37° C./5% CO$_2$, the cells were collected, resuspended in phenol-red free RPMI media containing 10% (v/v) dilapidated FBS (Hyclone, Cat. # SH30855.03) and dispensed into 96-well clear bottom tissue culture plates (CoStar, Cat. #3603), at 80,000 cells per well. Tested compounds were added to the cells in the same media (final concentration of DMSO was 0.1% (v/v)), and the plates were incubated at 37° C./5% CO$_2$ for 16-18 hr. Luciferase activity in the conditioned supernatants was determined with NanoGlo® assay reagents (Promega, Cat.# N1130). Percent inhibition values were calculated based on the fully inhibited and non-inhibited (DMSO) controls, and the values were regressed against concentrations of the tested compounds to derive IC50 values using a four-parameter non-linear fitting model.

Human Whole Blood Assay (Assay 3)

Compounds of the invention were tested in the human whole blood assay to measure their effects on IL-17A production as determined by cytokine secretion into 50% blood/media supernatant. Mixtures of sodium heparinized whole blood (isolated from healthy human donors) and the T cell activator CytoStim, in the presence or absence of compound, were plated in sterilized, tissue culture-treated 24-well plates. Specifically, the mixtures in each well were as follows: (1) 500 µL of whole blood, (2) 250 µL of compound diluted into RPMI-1640 media containing 10% HyClone™ FCS (Thermo Fisher Scientific, Waltham, Mass.), Gibco® Pen/Strep and Gibco® NEAA (Life Technologies, Grand Island, N.Y.), and (3) 250 µL of CytoStim (Miltenyi Biotech, Germany) diluted to a final concentration of 10 µL/mL in complete cell culture medium.

Mixtures were incubated at 37° C./5% $CO_2$ for 48 h, after which, 200 µL of clean supernatant (i.e., no red blood cells) from each well was transferred to a well in a 96-well plate. IL-17A cytokine expression was determined using 25 µL of the transferred supernatant diluted with 25 µL of Diluent 43 from the Human IL-17A V-PLEX™ kit (cat. # K151RFD-4, Meso Scale Discovery, Rockville, Md.). The assay was performed according to the manufacturer's instructions using included reagents. The IL-17A V-PLEX™ plates were read using the Meso Scale Discovery Imager (Model 1200). The levels of IL-17A were extrapolated from a standard curve using a four-parameter non-linear fitting model and expressed as pg/mL. These values were regressed against concentrations of the tested compounds to derive $IC_{50}$ values using a four-parameter non-linear fitting model.

hERG Assay (Assay 4)

Compounds of the invention were tested in vitro against the hERG (human ether-à-go-go-related gene) potassium ion channel (a surrogate for IKr, the rapidly activating delayed rectifier cardiac potassium ion channel).

The buffer was HEPES-buffered physiological saline (HB-PS) solution composed of: 137 mM NaCl, 4.0 mM KCl, 1.8 mM $CaCl_2$, 1 mM $MgCl_2$, 10 mM HEPES, 10 mM glucose, pH adjusted to 7.4 with NaOH, and 0.3% DMSO. Chemicals used in solution preparation were purchased from Sigma-Aldrich (St. Louis, Mo.), unless otherwise noted, and were of ACS reagent grade purity or higher.

HEK (human embryonic kidney) 293 cells were stably transfected with hERG cDNA.

For the patch clamp experiment, onset and steady state inhibition of hERG potassium current was measured using a pulse pattern with fixed amplitudes (depolarization: +20 mV for 2 s; repolarization: −50 mV for 2 s) repeated at 10 s intervals from a holding potential of −80 mV. Peak tail current was measured during the 2 s step to −50 mV. A steady state was maintained for at least 30 seconds before applying compound or positive control (cisapride). Peak tail currents were measured until a new steady state was achieved.

Data acquisition and analyses were performed using the suite of pCLAMP® (ver. 8.2) programs (MDS Analytical Technologies, Sunnyvale, Calif.). Steady state was defined by the limiting constant rate of change with time (linear time dependence). The steady state before and after each compound application was used to calculate the percentage of current inhibited at each concentration.

Concentration-response data were fit to an equation of the following form:

% Inhibition={1−1/[1+([Test]/IC50)N]}*100 where [Test] was the compound concentration, IC50 was the compound concentration at half-maximal inhibition, N was the Hill coefficient, and % Inhibition was the percentage of current inhibited at each compound concentration. Non-linear least squares fits were solved with the Solver add-in for Excel 2003 (Microsoft, WA) and the IC50 was calculated.

The results of assays 1 and 2 are shown in Table 2.

TABLE 2

| Compound # | RORγ Binding Ki Range* (nM) (Assay 1) | RORγt5X IC50 Range* (nM) (Assay 2) |
|---|---|---|
| 1 | +++ | +++ |
| 2 | +++ | +++ |
| 3 | +++ | |
| 4 | +++ | +++ |
| 5 | +++ | +++ |
| 6 | ++ | |
| 7 | +++ | ++ |
| 8 | +++ | + |
| 9 | ++ | |
| 10 | +++ | +++ |
| 11 | +++ | +++ |
| 12 | ++ | |
| 13 | +++ | +++ |
| 14 | +++ | +++ |
| 15 | +++ | +++ |
| 16 | ++ | |
| 17 | + | |
| 18 | +++ | + |
| 19 | +++ | ++ |
| 20 | ++ | |
| 21 | +++ | + |
| 22 | +++ | +++ |
| 23 | +++ | +++ |
| 24 | +++ | +++ |
| 25 | +++ | +++ |
| 26 | +++ | ++ |
| 27 | +++ | +++ |
| 28 | + | |
| 29 | ++ | |
| 30 | ++ | |
| 31 | +++ | +++ |
| 32 | ++ | |
| 33 | +++ | +++ |
| 34 | ++ | |
| 35 | ++ | |
| 36 | +++ | + |
| 37 | +++ | +++ |
| 38 | ++ | |
| 39 | +++ | +++ |
| 40 | ++ | |
| 41 | +++ | +++ |
| 42 | +++ | +++ |
| 43 | +++ | +++ |
| 44 | +++ | +++ |

TABLE 2-continued

| Compound # | RORγ Binding Ki Range* (nM) (Assay 1) | RORγt5X IC50 Range* (nM) (Assay 2) |
|---|---|---|
| 45 | +++ | +++ |
| 46 | +++ | +++ |
| 47 | +++ | +++ |

*+ means > 1000 nM; ++ means 100 nM – 1000 nM; +++ means < 100 nM.

TABLE 3-continued

| Compound Number | 50% Human Whole Blood Assay IC50, nM* (Assay 3) | hERG Assay (Compound at 3μM) % Inhibition (Assay 4) |
|---|---|---|
| 41 | +++ | 7.7 |
| 42 | + | 63.9 |
| 44 | + | 28.6 |
| 45 | + | |
| 46 | +++ | 44.3 |
| 47 | + | |

*+ means > 200 nM; ++ means 100 nM – 200 nM; +++ means < 100 nM.

The results of assays 1 to 4 with comparator compounds are shown in Table 4.

TABLE 4

| Comparator Compound | RORγ Binding Ki Range$^A$ (nM) (Assay 1) | RORγt5X IC50 Range$^A$ (nM) (Assay 2) | 50% Human Whole Blood Assay IC50, nM$^B$ (Assay 3) | hERG Assay (Compound at 3 μM) % Inhibition (Assay 4) |
|---|---|---|---|---|
| 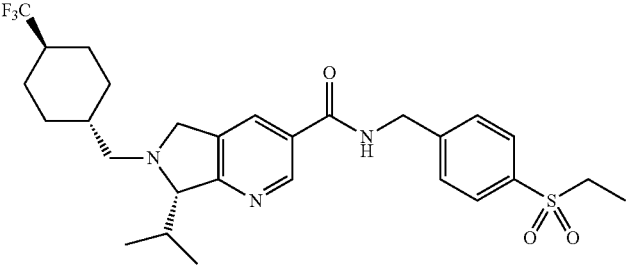 | +++ | +++ | | 57.0 |
| 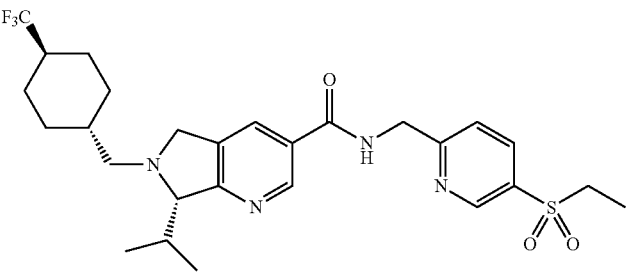 [SMILES: CCS(=O)(=O)c1ccc(CNC(=O)c2cnc3c(c2)CN(C[C@H]2CC[C@H](C(F)(F)F)CC2)[C@H]3C(C)C)nc1] | +++ | +++ | + | 45.4 |

$^A$+ means >1000 nM; ++ means 100 nM-1000 nM; +++ means <100 nM.
$^B$+ means >200 nM; ++ means 100 nM-200 nM; +++ means <100 nM.

The results of assays 3 and 4 are shown in Table 3.

TABLE 3

| Compound Number | 50% Human Whole Blood Assay IC50, nM* (Assay 3) | hERG Assay (Compound at 3μM) % Inhibition (Assay 4) |
|---|---|---|
| 1 | +++ | |
| 2 | +++ | |
| 4 | +++ | |
| 5 | +++ | |
| 10 | +++ | |
| 14 | +++ | |
| 25 | ++ | 3.2 |
| 33 | +++ | 29.1 |
| 39 | ++ | 32.7 |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:
1. A compound of the formula:

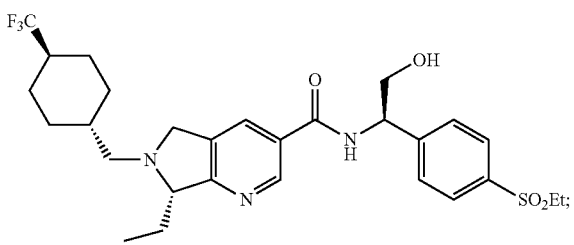

or a pharmaceutically acceptable salt thereof.

2. A pharmaceutical composition comprising a compound of the formula:

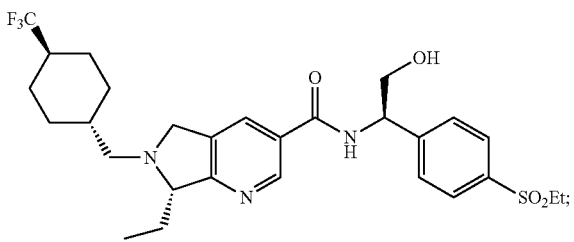

or a pharmaceutically acceptable salt thereof, and a pharmaceutically acceptable carrier.

3. A method of treating a disease or disorder selected from psoriasis, psoriatic arthritis (PsA), inflammatory bowel disease (IBD), rheumatoid arthritis, juvenile rheumatoid arthritis, systemic lupus erythematosus (SLE), multiple sclerosis, ankylosing spondylitis, and asthma in a subject, comprising administering to the subject a therapeutically effective amount of a compound having the formula:

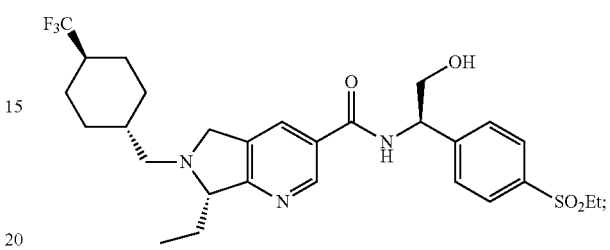

or a pharmaceutically acceptable salt thereof.

4. The method of claim 3, wherein the disease or disorder is psoriatic arthritis (PsA).

5. The method of claim 3, wherein the disease or disorder is ankylosing spondylitis.

6. The method of claim 3, wherein the disease or disorder is psoriasis.

* * * * *